United States Patent
Biro et al.

(10) Patent No.: US 11,154,515 B2
(45) Date of Patent: Oct. 26, 2021

(54) PHARMACEUTICAL COMPOSITIONS COMPRISING CANNABIDIOL AND BETA-CARYOPHYLLENE AND METHODS FOR THEIR USE

(71) Applicant: Phytecs, Inc., Los Angeles, CA (US)

(72) Inventors: Tamas Biro, Debrecen (HU); Ethan B. Russo, Vashon, WA (US)

(73) Assignee: Phytecs, Inc., Los Angeles, CA (US)

( * ) Notice: Subject to any disclaimer, the term of this patent is extended or adjusted under 35 U.S.C. 154(b) by 0 days.

(21) Appl. No.: 16/698,070

(22) Filed: Nov. 27, 2019

(65) Prior Publication Data

US 2020/0093755 A1 Mar. 26, 2020

Related U.S. Application Data

(63) Continuation of application No. PCT/US2018/035474, filed on May 31, 2018.

(60) Provisional application No. 62/513,336, filed on May 31, 2017, provisional application No. 62/513,335, filed on May 31, 2017, provisional application No. 62/513,334, filed on May 31, 2017.

(51) Int. Cl.
| | |
|---|---|
| A61K 31/05 | (2006.01) |
| A61P 29/00 | (2006.01) |
| A61K 9/00 | (2006.01) |
| A61K 31/015 | (2006.01) |

(52) U.S. Cl.
CPC .............. *A61K 31/05* (2013.01); *A61K 9/006* (2013.01); *A61K 31/015* (2013.01); *A61P 29/00* (2018.01)

(58) Field of Classification Search
CPC .. A61K 2300/00; A61K 31/05; A61K 31/015; A61K 36/185; A61K 31/09; A61K 31/222; A61K 9/006; A61P 17/00; A61P 29/00
See application file for complete search history.

(56) References Cited

U.S. PATENT DOCUMENTS

| | | |
|---|---|---|
| 9,095,555 B2 | 8/2015 | Winnicki |
| 9,447,019 B2 | 9/2016 | Mechoulam et al. |
| 2016/0143972 A1 | 5/2016 | Stebbins et al. |
| 2016/0243177 A1 | 8/2016 | Franklin et al. |
| 2016/0250270 A1* | 9/2016 | Wendschuh ............ A61K 31/05 514/454 |
| 2016/0324776 A1 | 11/2016 | Glatzel |

FOREIGN PATENT DOCUMENTS

| | | | |
|---|---|---|---|
| WO | WO 2015/074137 | 5/2015 | |
| WO | WO-2015065544 A1 * | 5/2015 | ............... A01H 5/00 |
| WO | WO 2016/064987 | 4/2016 | |
| WO | WO 2016/103254 | 6/2016 | |

OTHER PUBLICATIONS

Al Mansouri, et al. "The cannabinoid receptor 2 agonist, β-caryophyllene, reduced voluntary alcohol intake and attenuated ethanol-induced place preference and sensitivity in mice," Pharmacol Biochem Behav. (2014), 124:260-8. doi: 10.1016/j.pbb.2014.06.025.

Bahi, et al. "β-Caryophyllene, a CB2 receptor agonist produces multiple behavioral changes relevant to anxiety and depression in mice," Physiol Behav. (2014), 135:119-24. doi: 10.1016/j.physbeh.2014.06.003.

Bergamaschi, et al. "Cannabidiol reduces the anxiety induced by simulated public speaking in treatment-naïve social phobia patients," Neuropsychopharmacology. (2011), 36(6):1219-26. doi: 10.1038/npp.2011.6.

Bolczkei, et al. "Investigation of the role of TRPV1 receptors in acute and chronic nociceptive processes using gene-deficient mice," Pain. (2005),117(3):368-76.

Carrier, et al. "Inhibition of an equilibrative nucleoside transporter by cannabidiol: a mechanism of cannabinoid immunosuppression," Proc Natl Acad Sci U S A. (2006), 103(20): 7895-900.

ClinicalTrials.gov Identifier: NCT02397863 "Epidiolex and Drug Resistant Epilepsy in Children (CBD)." (2015), 5 pages.

Consroe, et al. "Open label evaluation of cannabidiol in dystonic movement disorders," Int J Neurosci. (1986), 30(4): 277-82.

Costa, et al. "The non-psychoactive cannabis constituent cannabidiol is an orally effective therapeutic agent in rat chronic inflammatory and neuropathic pain," Eur J Pharmacol. (2007), 556 (1-3):75-83.

Crippa, et al. "Effects of cannabidiol (CBD) on regional cerebral blood flow," Neuropsychopharmacology. (2004), 29(2): 417-26.

De Zeeuw, et al. "Cannabinoids with a propyl side chain in cannabis: occurrence and chromatographic behavior," Science. (1972), 175(4023): 778-9.

El-Alfy, et al. "Antidepressant-like effect of Δ9-tetrahydrocannabinol and other cannabinoids isolated from *Cannabis sativa* L," Pharmacol Biochem Behav. (2010), 95(4): 434-42. doi: 10.1016/j.pbb.2010.03.004.

Elphick, MR. and Egertova, M. "The neurobiology and evolution of cannabinoid signaling," Philos Trans R Soc Lond B Biol Sci. (2001), 356(1407): 381-408.

Eubanks, et al. "A molecular link between the active component of marijuana and Alzheimer's disease pathology," Mol Pharm. (2006), 3(6): 773-7.

Flores-Sanchez et al. "PKS activities and biosynthesis of cannabinoids and flavonoids in *Cannabis sativa* L. plants," Plant Cell Physiol. (2008), 49(12): 1767-82. doi: 10.1093/pcp/pcn150.

Gertsch, J. "Anti-inflammatory cannabinoids in diet: Towards a better understanding of CB(2) receptor action?" Commun Integr Biol. 2008, 1(1): 26-8.

(Continued)

*Primary Examiner* — Jean P Cornet
(74) *Attorney, Agent, or Firm* — Cooley LLP

(57) ABSTRACT

The disclosure describes compositions comprising beta-caryophyllene (BCP) and cannabidiol (CBD). The disclosure also describes compositions which further introduce low levels of THC. The disclosure further describes methods of making and using said compositions, including for the treatment of chronic pain, neurological disorders including epilepsy, addiction and inflammatory skin conditions. The disclosure further describes the use of fluorinated-CBD derivatives for treating inflammatory skin conditions.

21 Claims, 30 Drawing Sheets

(56) References Cited

OTHER PUBLICATIONS

Gertsch, et al. "Beta-caryophyllene is a dietary cannabinoid." Proc Natl Acad Sci U S A. (2008), 105(26): 9099-104. doi: 10.1073/pnas.0803601105.
"Guidance for Industry Botanical Drug Products" (Draft Guidance). U.S. Department of Health and Human Services, Food and Drug Administration, Center for Drug Evaluation and Research (CDER). (2000). 43 pages.
Hoaken, PN and Stewart, SH. "Drugs of abuse and the elicitation of human aggressive behavior," Addict Behav. (2003), 28(9):1533-54.
Holley, et al. "Constituents of *Cannabis sativa* L. XI: Cannabidiol and cannabichromene in samples of known geographical origin," J Pharm Sci. (1975), 64(5): 892-4.
Horvath, et al. "Analgesic effects of the novel semicarbazide-sensitive amine oxidase inhibitor SZV 1287 in mouse pain models with neuropathic mechanisms: Involvement of transient receptor potential vanilloid 1 and ankyrin 1 receptors," Pharmacol Res. (2018), 131:231-243. doi: 10.1016/j.phrs.2018.02.006.
Jayaprakasha, et al. "Volatile constituents from *Cinnamomum zeylanicum* fruit stalks and their antioxidant activities," J Agric Food Chem. (2003), 51(15):4344-8.
Klauke, et al. "The cannabinoid $CB_2$ receptor-selective phytocannabinoid beta-caryophyllene exerts analgesic effects in mouse models of inflammatory and neuropathic pain," Eur Neuropsychopharmacol. (2014), (4):608-20. doi: 10.1016/j.euroneuro.2013.10.008.
Legault J. and Pichette A. "Potentiating effect of beta-caryophyllene on anticancer activity of alpha-humulene, isocaryophyllene and paclitaxel," J Pharm Pharmacol. (2007), 59(12):1643-7.
Malone, et al. "Cannabidiol reverses the reduction in social interaction produced by low dose Δ9-tetrahydrocannabinol in rats," Pharmacol Biochem Behav. (2009), 93(2):91-6. doi: 10.1016/j.pbb.2009.04.010.
McAllister, et al. "Cannabidiol as a novel inhibitor of Id-1 gene expression in aggressive breast cancer cells," Mol Cancer Ther. (2007), 6(11): 2921-7.
Mechoulam, et al. "Cannabidiol—recent advances," Chem Biodivers. (2007), (8):1678-92.
Mockute, et al. "The essential oil of *Origanum vulgare* L. ssp. *vulgare* growing wild in vilnius district (Lithuania)," Phytochemistry. (2001), 57(1): 65-9.
Orav, et al. "Effect of storage on the essential oil composition of *Piper nigrum* L. fruits of different ripening states," J Agric Food Chem. (2004), 52(9): 2582-6.
Pertwee, RG. "The diverse CB1 and CB2 receptor pharmacology of three plant cannabinoids: delta9-tetrahydrocannabinol, cannabidiol and delta9-tetrahydrocannabivarin," Br J Pharmacol. (2008), 153(2):199-215.
Pertwee, RG. "The pharmacology of cannabinoid receptors and their ligands: an overview," Intl J of Obesity. (2006) 30: S13-S18.
Russo E. and Guy GW. "A tale of two cannabinoids: the therapeutic rationale for combining tetrahydrocannabinol and cannabidiol," Med Hypotheses. (2005), 66(2): 234-46.
Showalter, et al. "Evaluation of binding in a transfected cell line expressing a peripheral cannabinoid receptor (CB2): identification of cannabinoid receptor subtype selective ligands," J Pharmacol Exp Ther. (1996), 278(3): 989-99.
Skold, et al. "The fragrance chemical beta-caryophyllene-air oxidation and skin sensitization," Food Chem Toxicol. (2006), 44(4):538-45.
Snider, et al. "Beneficial and Adverse Effects of Cannabidol in a Parkinson Patient with Sinemet-Induced Dystonic Dyskinesia," Neurology, (1985), 35(4): 2 pages.
Zaneleti, et al. "Antidepressant-like effects of cannabidiol in mice: possible involvement of 5-HT1A receptors," Br J Pharmacol. (2010), 159(1):122-8. doi: 10.1111/j.1476-5381.2009.00521.x.
Zuardi, et al. "Cannabidiol, a Cannabis sativa constituent, as an antipsychotic drug," Braz J Med Biol Res. (2006), 39(4):421-9.
Extended European Search Report dated Mar. 4, 2021, for European Application No. EP18809477.5, 9 pages.
Liu et al., "Evaluation of drug combination effect using a Bliss independence dose-response surface model," Stat Biopharm Res. 2018; 10(2): 112-122.

\* cited by examiner

Fig. 16

| CBD (µM) | BCP (µM) | | | | | | | | | | | |
|---|---|---|---|---|---|---|---|---|---|---|---|---|
| | 0.0001 | 0.001 | 0.01 | 0.013 | 0.1 | 0.13 | 0.3 | 1.0 | 3.0 | 10.0 | 30.0 | 100.0 | 300.0 |
| 0.00001 | 1:10 | 1:100 | 1:1000 | 1:1300 | 1:10000 | 1:13000 | 1:30000 | 1:1x10⁵ | 1:3x10⁵ | 1:1x10⁶ | 1:3x10⁶ | 1:1x10⁷ | 1:3x10⁷ |
| 0.0001 | 1:1 | 1:10 | 1:100 | 1:130 | 1:1000 | 1:1300 | 1:3000 | 1:10000 | 1:30000 | 1:1x10⁵ | 1:3x10⁵ | 1:1x10⁶ | 1:3x10⁶ |
| 0.001 | 10:1 | 1:1 | 1:10 | 1:13 | 1:100 | 1:130 | 1:300 | 1:1000 | 1:3000 | 1:10000 | 1:30000 | 1:1x10⁵ | 1:3x10⁵ |
| 0.01 | 100:1 | 10:1 | 1:1 | 1:1.3 | 1:10 | 1:1.3 | 1:30 | 1:100 | 1:300 | 1:1000 | 1:3000 | 1:10000 | 1:30000 |
| 0.1 | 1000:1 | 100:1 | 10:1 | 7.69:1 | 1:1 | 1:1.3 | 1:3 | 1:10 | 1:30 | 1:100 | 1:300 | 1:1000 | 1:3000 |
| 0.3 | 3000:1 | 300:1 | 30:1 | 23.1:1 | 3:1 | 2.31:1 | 1:1 | 1:3.33 | 1:10 | 1:33.3 | 1:100 | 1:333 | 1:1000 |
| 1.0 | 10000:1 | 1000:1 | 100:1 | 76.9:1 | 10:1 | 7.69:1 | 3.33:1 | 1:1 | 1:3 | 1:10 | 1:30 | 1:100 | 1:300 |
| 3.0 | 30000:1 | 3000:1 | 300:1 | 231:1 | 30:1 | 23.1:1 | 10:1 | 3:1 | 1:1 | 1:3.33 | 1:10 | 1:33.3 | 1:100 |
| 10.0 | 1x10⁵:1 | 10000:1 | 1000:1 | 769:1 | 100:1 | 76.9:1 | 33.3:1 | 10:1 | 3.33:1 | 1:1 | 1:3 | 1:10 | 1:30 |
| 30.0 | 3x10⁵:1 | 30000:1 | 3000:1 | 2307:1 | 300:1 | 231:1 | 100:1 | 30:1 | 10:1 | 3:1 | 1:1 | 1:3.33 | 1:10 |

Fig. 18A

| Model | Read-out | CBD Conc. | | | HUF101 Conc. | | | HUF103 Conc. | | | HU559a Conc. | | |
|---|---|---|---|---|---|---|---|---|---|---|---|---|---|
| | | 0.01 µM | 0.1 µM | 1 µM | 0.01 µM | 0.1 µM | 1 µM | 0.01 µM | 0.1 µM | 1 µM | 0.01 µM | 0.1 µM | 1 µM |
| 1 (SDS) | IL6 | 69% | 67% | 61% | 114% | 10% | 114% | 76% | 19% | 146% | 543% | 76% | 47% |
| | IL8 | 30% | 39% | 57% | 26% | 5% | 84% | 7% | 6% | 101% | 251% | 31% | 26% |
| 2 (Ni) | IL6 | 39% | 24% | 57% | 22% | 64% | 30% | 1% | 24% | 3% | 1% | 27% | 16% |
| | IL8 | 34% | 15% | 73% | 10% | 10% | 15% | 1% | 84% | 1% | 1% | 23% | 32% |
| | IL1α | 150% | 119% | 151% | 100% | 100% | 113% | 7% | 108% | 2% | 2% | 111% | 159% |
| | TNFα | 50% | 95% | 156% | 104% | 130% | 117% | 43% | 108% | 770% | 2% | 107% | 116% |
| 3 (Cary) | IL6 | 106% | 98% | 123% | 56% | 97% | 147% | 5% | 100% | 1% | 4% | 100% | 181% |
| | IL8 | 187% | 161% | 219% | 144% | 355% | 677% | 11% | 161% | 1% | 5% | 160% | 280% |

Fig. 18B

| Model | Read-out | CBD Conc. | | | HUF101 Conc. | | | HUF103 Conc. | | | HU559a Conc. | | |
|---|---|---|---|---|---|---|---|---|---|---|---|---|---|
| | | 0.01 µM | 0.1 µM | 1 µM | 0.01 µM | 0.1 µM | 1 µM | 0.01 µM | 0.1 µM | 1 µM | 0.01 µM | 0.1 µM | 1 µM |
| 4 (SLIGRL) | IL6 | 131% | 157% | 173% | 121% | 362% | 144% | 0% | 335% | 16% | 5% | 141% | 115% |
| | IL8 | 137% | 76% | 124% | 85% | 218% | 68% | 0% | 214% | 14% | 3% | 108% | 83% |
| | IL1α | 110% | 222% | 145% | 102% | 77% | 157% | 6% | 85% | 3% | 4% | 109% | 191% |
| | IL1β | 109% | 149% | 141% | 44% | 62% | 128% | 5% | 53% | 26% | 2% | 123% | 238% |
| 5 (UVB) | IL6 | 89% | 88% | 75% | 71% | 92% | 119% | 7% | 46% | 2% | 2% | 60% | 224% |
| | IL8 | 85% | 104% | 85% | 50% | 75% | 136% | 4% | 67% | 1% | 2% | 48% | 97% |
| | IL1α | 37% | 77% | 43% | 29% | 44% | 16% | 462% | 15% | 37% | 465% | 15% | 44% |
| | IL1β | 86% | 162% | 413% | 185% | 210% | 288% | 10189% | 142% | 1001% | 9126% | 192% | 445% |
| 6 (pIC) | IL6 | 208% | 110% | 47% | 27% | 31% | 31% | 720% | 13% | 309% | 748% | 25% | 111% |
| | IL8 | 133% | 90% | 43% | 24% | 20% | 34% | 427% | 17% | 192% | 644% | 23% | 60% |
| | IL1A | 139% | 134% | 208% | 77% | 137% | 258% | 4% | 68% | 1% | 13% | 58% | 67% |
| 7 (SEB-TSLP) | IL6 | 71% | 68% | 95% | 66% | 88% | 41% | 3% | 22% | 2% | 4% | 25% | 24% |
| | IL8 | 60% | 40% | 22% | 62% | 76% | 23% | 3% | 33% | 1% | 9% | 42% | 25% |

PHARMACEUTICAL COMPOSITIONS COMPRISING CANNABIDIOL AND BETA-CARYOPHYLLENE AND METHODS FOR THEIR USE

CROSS-REFERENCE TO RELATED APPLICATIONS

This application is a Continuation U.S. Utility Application under 35 U.S.C. § 111, claiming the benefit of priority to International Application No. PCT/US2018/035474, filed on May 31, 2018, which itself claims priority to U.S. Provisional Application Nos. 62/513,334, filed May 31, 2017; 62/513,335, filed May 31, 2017; and 62/513,336, filed May 31, 2017, the contents of each of which are incorporated herein by reference in their entireties.

FIELD

The present disclosure generally relates to compositions and methods for producing and using pharmaceuticals comprising cannabidiol and beta-caryophyllene, methods of making the compositions, and methods for using the compositions for the treatment of a variety of symptoms and diseases. The disclosure further relates to the use of fluorinated-CBD derivatives for treating inflammatory skin conditions.

BACKGROUND

Unrelieved chronic pain is a critical health problem in the US and worldwide. A report by the Institute of Medicine estimated that 116 million Americans suffer from pain that persists for weeks to years, with resulting annual costs exceeding $560 million. There are no adequate long-term therapies for chronic pain sufferers, leading to significant costs for both society and the individual. Pain often results in disability and, even when not disabling, it has a profound effect on the quality of life. Pain treatment frequently fails even when the circumstances of care delivery are optimal, such as attentive, well-trained physicians; ready access to opioids; use of adjuvant analgesics; availability of patient-controlled analgesia; and evidence-based use of procedures like nerve blocks and IT pumps.

The most commonly used therapy for chronic pain is the application of opioid analgesics and nonsteroidal anti-inflammatory drugs, but these drugs can lead to addiction and may cause side effects, such as drug dependence, tolerance, respiratory depression, sedation, cognitive failure, hallucinations, and other systemic side effects. Despite the wide usage of pharmaceuticals, there is a strikingly low success rate for its effectiveness in pain relief. A large randomized study with various medications found only one out of every two or three patients achieving at least 50% pain relief (Finnerup et al., Pain, 118(3):289-305, 2005). A follow-up study using the most developed pharmacological treatments found the same results, indicating that there was no improvement in the efficacy of medications for pain (Finnerup et al., Pain, 150(3):573-81, 2010).

Alcohol and drug dependence is a serious medical, social, and economic problem in terms of morbidity, mortality and disability worldwide. In 2014, the National Survey on Drug Use and Health estimated that approximately 9.7% of Americans over the age of 12 were struggling with addiction associated with an illicit drug, with higher percentages of Americans admitting to alcohol and prescription drug abuse.

The costs of addiction on families and States are staggering. The National Institute on Drug Abuse estimates that the health care cost associated with alcohol and illicit drug use is $25 billion and $11 billion, respectively. Several medications, including methadone, buprenorphine, and naltrexone have been developed to assist patients undergoing rehabilitation programs. Even with the aid of these medications, the average success rate of addiction treatment is alarmingly low, with average recovery rates around 50% of individuals that complete a program. Success rates that account for individuals who fail to complete the rehab program are even lower.

Thus, there is an urgent need for improved compositions and treatments for addiction and pain with improved success rates, and improved cooperation rates from patients. The present invention addresses many of the shortcomings of current technology, and provides patients with a new aid in their fight against addiction and relief from pain.

SUMMARY OF THE DISCLOSURE

In some embodiments, the present disclosure provides pharmaceutical compositions containing cannabidiol (CBD) and E-beta-caryophyllene ((E)-BCP). In other embodiments, the present disclosure provides pharmaceutical compositions containing tetrahydrocannabinol (THC), CBD, and (E)-BCP.

In some embodiments, the pharmaceutical compositions of the present disclosure provide analgesic benefits in a well-tolerated treatment (e.g., reduced side effects compared to THC treatment alone). Thus, in some embodiments, the pharmaceutical compositions of the present disclosure provide improved pain control for subjects. In some embodiments, the improved pain control is achieved with a pharmaceutical composition that is substantially THC-free.

In some embodiments, the pharmaceutical compositions of the present disclosure are opioid sparing. That is, in some embodiments, the pharmaceutical compositions of the present disclosure can be used in conjunction with one or more traditional pain treatments (e.g., opioids), thereby reducing the frequency or amount of traditional pain killers administered to the subject (e.g., reducing opioid treatment of cancer patients).

In other embodiments, the pharmaceutical compositions of the present disclosure are opioid replacements. That is in some embodiments, the pharmaceutical compositions of the present disclosure can be used in place of other pain treatments. In some embodiments of the present disclosure, the pharmaceutical compositions comprising CBD, (E)-BCP, and (in selected embodiments) THC provide an alternative to traditional pain treatments, and further provide a low adverse event profile and very low drug abuse liability.

In some embodiments, the pharmaceutical compositions of the present disclosure provide additional benefits to the subject beyond pain control. In some embodiments, the pharmaceutical compositions comprising CBD, (E)-BCP, and (in selected embodiments) THC, provide subjects with improved sleep and quality of life.

In other embodiments, the pharmaceutical compositions of the present disclosure provide benefits beyond those obtained through concomitant administration with pain killers. For example, in some embodiments, the present disclosure provides methods of treating patients recuperating from one or more kinds of substance addiction.

In some embodiments, the pharmaceutical compositions of the present disclosure effectively treat opioid addiction in a subject in need thereof.

In some embodiments, the pharmaceutical compositions of the present disclosure effectively treat cocaine addiction in a subject in need thereof.

In some embodiments, the pharmaceutical compositions of the present disclosure effectively treat alcohol addiction in a subject in need thereof.

In some embodiments, the pharmaceutical compositions of the present disclosure effectively treat nicotine addiction in a subject in need thereof.

In some embodiments, the present disclosure provides a pharmaceutical composition containing one or more active ingredients, wherein said active ingredients comprise a therapeutically effective amount of CBD and (E)-BCP.

In some embodiments, the present disclosure provides a pharmaceutical composition containing one or more active ingredients, wherein the active ingredients consist essentially of a therapeutically effective amount of CBD and (E)-BCP.

In some embodiments, the present disclosure provides a pharmaceutical composition containing one or more active ingredients, wherein the active ingredients consist of a therapeutically effective amount of CBD and (E)-BCP.

In some embodiments, the present disclosure provides a pharmaceutical composition containing the active ingredients CBD and (E)-BCP, wherein the ratio of CBD to (E)-BCP is from about 1:10 to about 1:30. In some embodiments, the present disclosure provides a pharmaceutical composition containing the active ingredients CBD and (E)-BCP, wherein the ratio of CBD to (E)-BCP is from about 30:1 to about 10:1.

In some embodiments, the present disclosure provides a pharmaceutical composition containing the active ingredients CBD and (E)-BCP, wherein the ratio of CBD to (E)-BCP is about 1-3000 parts CBD and 20-4000 parts (E)-BCP. In some embodiments, the present disclosure provides a pharmaceutical composition containing the active ingredients CBD and (E)-BCP, wherein the ratio of CBD to (E)-BCP is about 20-4000 parts CBD and 1-3000 parts (E)-BCP.

In some embodiments, the present disclosure provides a pharmaceutical composition containing the active ingredients CBD and (E)-BCP, wherein the active ingredient portion contains about 1-10% CBD and about 90-99% (E)-BCP by weight. In some embodiments, the present disclosure provides a pharmaceutical composition containing the active ingredients CBD and (E)-BCP, wherein the active ingredient portion contains about 90-99% CBD and about 1-10% (E)-BCP by weight.

In some embodiments, the present disclosure provides a pharmaceutical composition containing one or more active ingredients, wherein said active ingredients comprise a therapeutically effective amount of CBD, (E)-BCP and THC.

In some embodiments, the present disclosure provides a pharmaceutical composition containing one or more active ingredients, wherein the active ingredients consist essentially of a therapeutically effective amount of CBD, (E)-BCP, and THC.

In some embodiments, the present disclosure provides a pharmaceutical composition containing one or more active ingredients, wherein the active ingredients consist of a therapeutically effective amount of CBD, (E)-BCP, and THC.

In some embodiments, the present disclosure provides a pharmaceutical composition containing the active ingredients CBD and THC, wherein the ratio of CBD to THC is from about 1:10 to about 1:3000 or about 3000:1 to about 10:1.

In some embodiments, the present disclosure provides a pharmaceutical composition containing the active ingredients BCP and THC, wherein the ratio of BCP to THC is from about 1:30 to about 1:1 or about 1:1 to about 3000:1.

In some embodiments, the present disclosure provides a pharmaceutical composition containing the active ingredients THC, CBD and (E)-BCP, wherein the ratio of THC:CBD:(E)-BCP is about 1-10 parts THC: 20-4000 parts CBD: and 1-3000 parts (E)-BCP. In some embodiments, the present disclosure provides a pharmaceutical composition containing the active ingredients THC, CBD and (E)-BCP, wherein the ratio of THC to CBD to (E)-BCP is about 1-10 parts THC: 1-3000 parts CBD: and 20-40000 parts (E)-BCP.

In some embodiments, the present disclosure provides a pharmaceutical composition containing the active ingredients THC, CBD and (E)-BCP, wherein the active ingredient portion contains about 1-10% THC, about 80-90% CBD, and about 1-10% (E)-BCP by weight. In some embodiments, the present disclosure provides a pharmaceutical composition containing the active ingredients THC, CBD and (E)-BCP, wherein the active ingredient portion contains about 1-10% THC, about 1-10% CBD, and about 80-90% (E)-BCP by weight.

In some embodiments, the present disclosure provides a pharmaceutical composition, wherein at least one of the active ingredients is an enriched active ingredient.

In some embodiments, the present disclosure provides a pharmaceutical composition, wherein all of the active ingredients are enriched active ingredients.

In some embodiments, the present disclosure provides a pharmaceutical composition, wherein at least one of the active ingredients is a substantially pure active ingredient.

In some embodiments, the present disclosure provides a pharmaceutical composition, wherein all of the active ingredients are substantially pure active ingredients.

In some embodiments, the present disclosure provides a pharmaceutical composition wherein a single dose of the composition comprises an active ingredient portion of 300-500 milligrams.

In some embodiments, the present disclosure provides a pharmaceutical composition wherein the pharmaceutical composition comprises from about 300 mg to about 1000 mg of CBD.

In some embodiments, the present disclosure provides a pharmaceutical composition wherein the pharmaceutical composition comprises from about 10 mg to about 100 mg of (E)-BCP.

In some embodiments, the present disclosure provides a pharmaceutical composition wherein the pharmaceutical composition comprises from about 1 mg to about 20 mg of THC.

In some embodiments, the present disclosure provides a pharmaceutical composition wherein the composition is formulated as an oral dosage form.

In some embodiments, the present disclosure provides a pharmaceutical composition wherein the composition is formulated as a parenteral dosage form.

In some embodiments, the present disclosure provides a pharmaceutical composition wherein the composition is formulated as a transdermal patch, cream or ointment.

In some embodiments, the present disclosure provides a pharmaceutical composition wherein the composition is formulated as an oral mucosal absorption spray.

In some embodiments, the pharmaceutical formulations of the present disclosure effectively reduce inflammation in a subject in need thereof.

In some embodiments, the present disclosure provides a method of reducing inflammation in a subject in need thereof, comprising administering to the subject a composition containing one or more active ingredients, said active ingredients comprising a therapeutically effective amount of CBD and (E)-BCP.

In some embodiments, the present disclosure provides a method of reducing inflammation in a subject in need thereof, comprising administering to the subject a composition containing one or more active ingredients, said active ingredients comprising a therapeutically effective amount of CBD, (E)-BCP, and THC.

In some embodiments, the present disclosure provides a method of treating substance addiction, comprising administering to a subject in need thereof a composition containing one or more active ingredients, said active ingredients comprising a therapeutically effective amount of CBD and (E)-BCP.

In some embodiments, the present disclosure provides a method of treating substance addiction, said method comprising administering to a patient in need thereof a composition containing one or more active ingredients, said active ingredients comprising a therapeutically effective amount of THC, CBD, and (E)-BCP.

In some embodiments, the present disclosure provides a method of treating pain, said method comprising administering to a subject in need thereof a composition containing one or more active ingredients, said active ingredients comprising a therapeutically effective amount of CBD and (E)-BCP.

In some embodiments, the present disclosure provides a method of treating pain, said method comprising administering to a subject in need thereof a composition containing one or more active ingredients, said active ingredients comprising a therapeutically effective amount of THC, CBD, and (E)-BCP.

In some embodiments, the present disclosure provides a method of treating a neurological disease or disorder, said method comprising administering to a subject in need thereof a composition containing one or more active ingredients, said active ingredients comprising a therapeutically effective amount of CBD and (E)-BCP.

In some embodiments, the present disclosure provides a method of treating a neurological disease or disorder, said method comprising administering to a subject in need thereof a composition containing one or more active ingredients, said active ingredients comprising a therapeutically effective amount of THC, CBD, and (E)-BCP.

In one aspect, the present disclosure provides a method of treating an inflammatory skin disease or disorder, said method comprising administering to a subject in need thereof a composition containing one or more active ingredients, said active ingredients comprising a therapeutically effective amount of a fluorinated CBD as described herein.

BRIEF DESCRIPTION OF THE FIGURES

FIG. 1A shows CBD inhibition of IL-1α gene expression. FIG. 1B shows CBD inhibition of IL-1β gene expression.

FIG. 2A shows BCP inhibition of IL-1α gene expression. FIG. 2B shows BCP inhibition of IL-1β gene expression.

FIG. 3A shows CBD+BCP combination inhibition of IL-1α gene expression. FIG. 3B shows CBD+BCP combination inhibition of IL-1β gene expression.

FIG. 4A shows the baseline effects of CBD and BCP on ipsilateral paw swelling in the absence of an inflammatory stimuli. FIG. 4B shows the effects of CBD and BCP pretreatment on carrageenan-induced ipsilateral paw swelling.

FIG. 6A shows the baseline effects of CBD and BCP on mechanonociceptive thresholds in the absence of an inflammatory stimuli. FIG. 6B shows the effects of CBD and BCP pretreatment on carrageenan-induced changes in mechanonociceptive thresholds.

FIG. 8A shows the baseline effects of CBD+BCP combination treatment on ipsilateral paw swelling in the absence of an inflammatory stimuli. FIG. 8B shows the effects of CBD+BCP combination pretreatment on carrageenan-induced ipsilateral paw swelling.

FIG. 10A shows the baseline effects of CBD+BCP on mechanonociceptive thresholds in the absence of an inflammatory stimuli. FIG. 10B shows the effects of CBD and BCP pretreatment on carrageenan-induced changes in mechanonociceptive thresholds.

FIG. 12A shows the baseline effects of CBD+BCP combination treatment on ipsilateral paw swelling in the absence of an inflammatory stimuli. FIG. 12B shows the effects of CBD+BCP combination pretreatment on carrageenan-induced ipsilateral paw swelling.

FIG. 14A shows the baseline effects of drug treatment on mechanonociceptive thresholds in the absence of an inflammatory stimuli. FIG. 14B shows the effects of CBD+BCP combination pretreatment on carrageenan-induced changes in mechanonociceptive thresholds.

FIG. 16 shows the molar ratios of CBD:BCP used in RAW-Blue™ in vitro experiments.

FIG. 18A-FIG. 18B provide tables summarizing the effects of CBD and F-CBDs on cytokine gene expression in seven in vitro models of skin inflammation.

FIG. 19A shows the effects in a non-specific inflammation/irritation model. FIG. 19B shows the effects in a contact allergic inflammation/irritation model.

FIG. 21A shows the effects in a PAR2-receptor activation inflammation/irritation model. FIG. 21B shows the effects in a UVB-induced inflammation/irritation model.

DETAILED DESCRIPTION

I. Definitions

Figure 1A:
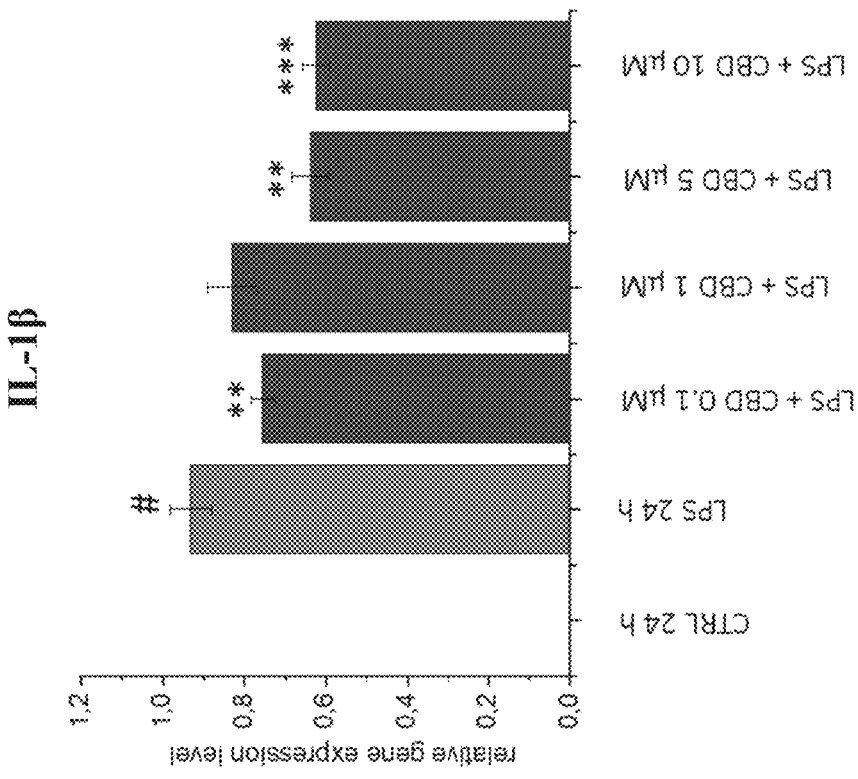
FIG. 1A and FIG. 1B show CBD inhibition of inflammatory cytokine gene expression in LPS-stimulated murine macrophages (RAW 264.7).

While the following terms are believed to be well understood by one of ordinary skill in the art, the following definitions are set forth to facilitate explanation of the presently disclosed subject matter.

The term "a" or "an" refers to one or more of that entity, i.e., can refer to a plural referent. As such, the terms "a" or "an", "one or more" and "at least one" are used interchangeably herein. In addition, reference to "an element" by the indefinite article "a" or "an" does not exclude the possibility that more than one of the elements is present, unless the context clearly requires that there is one and only one of the elements.

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

Throughout this application, the term "about" is used to indicate that a value includes the inherent variation of error for the device or the method being employed to determine the value, or the variation that exists among the samples being measured. In some embodiments, the term "about" means within 5% of the reported numerical value. When used in conjunction with a range or series of values, the term "about" applies to the endpoints of the range or each of the values enumerated in the series, unless otherwise indicated.

As used herein, the verb "comprise" as is used in this description and in the claims and its conjugations are used in its non-limiting sense to mean that items following the word are included, but items not specifically mentioned are not excluded.

The terms "composition" and "pharmaceutical composition" are used interchangeably herein. In some embodiments, the compositions described herein comprise the active ingredients of cannabidiol (CBD) and (E)-beta-caryophyllene ((E)-BCP) and are referred to herein as "CBD-BCP compositions" or "Carydiol™ compositions", used interchangeably herein. In some embodiments, the active ingredients of a CBD-BCP composition further comprises tetrahydrocannabinol (THC). Therefore, in some embodiments, the compositions described herein (e.g., CBD-BCP compositions) comprise the active ingredients of CBD, E-BCP, and THC.

A "subject" is a living animal, particularly a mammal, which can be treated with a pharmaceutical composition described herein. In some embodiments, the subject is a human. In some embodiments, the human subject is a human child, a human teenager, or a human adult. In some embodiments, the subject or patient is a non-human animal, including research animals such as a mouse, a rat, a pig, a dog, a rabbit, a monkey or other non-human primate, or a goat.

The term "fluorinated CBD" (or "F-CBD") as used herein refers to CBD where at least one of the hydrogen atoms of CBD is replaced with a fluorine atom. In some embodiments of the present disclosure, the F-CBD is a compound of formula (I):

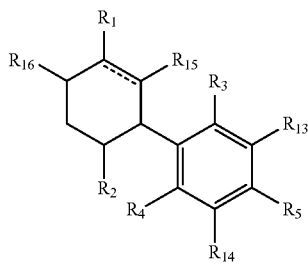

(I)

wherein

══ is a single or double bond;

$R_1$ is selected from straight or branched $C_1$-$C_8$ alkyl, straight or branched $C_2$-$C_{10}$ alkenyl, straight or branched $C_2$-$C_{10}$ alkynyl, —C(═O)$R_8$, —C(═O)O$R_9$ each optionally substituted by at least one F;

$R_2$ is selected from straight or branched $C_1$-$C_8$ alkyl, straight or branched $C_2$-$C_{10}$ alkenyl, straight or branched $C_2$-$C_{10}$ alkynyl, each optionally substituted by at least one F;

$R_3$ and $R_4$ are each independently selected from H, straight or branched $C_1$-$C_5$ alkyl, —O$R_{10}$, —C(═O)$R_{11}$, —OC(═O)$R_{12}$; provided that at least one of $R_3$ and $R_4$ is different than H;

$R_5$ is selected from a straight or branched $C_5$-$C_{12}$ alkyl, a straight or branched $C_5$-$C_9$ alkoxy, a straight or branched $C_1$-$C_7$ ether, each being optionally substituted by at least one substituent selected from —OH, —NH$_3$, straight or branched $C_1$-$C_5$ amine, halogen, phenyl, aryl, heteroaryl, cycloalkyl and heterocycloalkyl;

$R_8$, and $R_9$ are independently selected from H, OH, straight or branched $C_1$-$C_5$ alkyl, straight or branched $C_1$-$C_5$alkoxy, —NH$_3$, straight or branched $C_1$-$C_5$ amine;

$R_{10}$ is selected from H, a straight or branched $C_1$-$C_5$ alkyl; and $R_{11}$ and $R_{12}$ are independently selected from H, OH, straight or branched $C_1$-$C_5$ alkyl, straight or branched $C_1$-$C_5$ alkoxy, —NH$_3$, straight or branched $C_1$-$C_5$ amine;

$R_{13}$, $R_{14}$, $R_{15}$ and $R_{16}$ are each optionally selected from H and F;

provided that at least one of $R_{13}$, $R_{14}$, $R_{15}$ and $R_{16}$ is F or at least one of $R_1$ and $R_2$ is substituted with F.

In another aspect of the present disclosure, the F-CBD is a compound having the general formula (Ia):

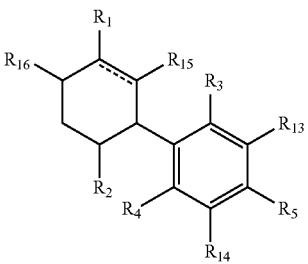

(Ia)

wherein

══ is a single or double bond;

$R_1$ is selected from straight or branched $C_1$-$C_8$ alkyl, straight or branched $C_2$-$C_{10}$ alkenyl, straight or branched $C_2$-$C_{10}$ alkynyl, —C(═O)$R_8$, —C(═O)O$R_9$ each optionally substituted by at least one F;

$R_2$ is selected from straight or branched $C_1$-$C_8$ alkyl, straight or branched $C_2$-$C_{10}$ alkenyl, straight or branched $C_2$-$C_{10}$ alkynyl, each optionally substituted by at least one F;

$R_3$ and $R_4$ are each independently selected from H, straight or branched $C_1$-$C_5$ alkyl, —O$R_{10}$, —C(═O)$R_{11}$, —OC(═O)$R_{12}$; provided that at least one of $R_3$ and $R_4$ is different than H;

$R_5$ is selected from a straight or branched $C_5$ alkyl, each being optionally substituted by at least one substituent selected from —OH, —NH$_3$, straight or branched $C_1$-$C_5$ amine, halogen, phenyl, aryl, heteroaryl, cycloalkyl and heterocycloalkyl;

$R_8$, and $R_9$ are independently selected from H, OH, straight or branched $C_1$-$C_5$ alkyl, straight or branched $C_1$-$C_5$alkoxy, —NH$_3$, straight or branched $C_1$-$C_5$ amine;

$R_{10}$ is selected from H, a straight or branched $C_1$-$C_5$ alkyl; and $R_{11}$ and $R_{12}$ are independently selected from H, OH, straight or branched $C_1$-$C_5$ alkyl, straight or branched $C_1$-$C_5$ alkoxy, —NH$_3$, straight or branched $C_1$-$C_5$ amine;

$R_{13}$, $R_{14}$, $R_{15}$ and $R_{16}$ are each optionally selected from H and F;

provided that at least one of $R_{13}$, $R_{14}$, $R_{15}$ and $R_{16}$ is F or at least one of $R_1$ and $R_2$ is substituted with F.

In another aspect of the present disclosure, the F-CBD is a compound having the general formula (II):

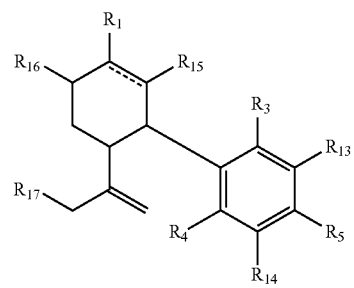

(II)

wherein

══ is a single or double bond;

$R_1$ is selected from straight or branched $C_1$-$C_8$ alkyl, straight or branched $C_2$-$C_{10}$ alkenyl, straight or branched $C_2$-$C_{10}$ alkynyl, —C(═O)$R_8$, —C(═O)O$R_9$ each optionally substituted by at least one F;

$R_3$ and $R_4$ are each independently selected from H, straight or branched $C_1$-$C_5$ alkyl, —O$R_{10}$, —C(═O)$R_{11}$, —OC(═O)$R_{12}$; provided that at least one of $R_3$ and $R_4$ is different than H;

$R_5$ is selected from a straight or branched $C_5$-$C_{12}$ alkyl, a straight or branched $C_5$-$C_9$ alkoxy, a straight or branched $C_1$-$C_7$ ether, each being optionally substituted by at least one substituent selected from —OH, —NH$_3$, straight or branched $C_1$-$C_5$ amine, halogen, phenyl, aryl, heteroaryl, cycloalkyl and heterocycloalkyl;

$R_8$, and $R_9$ are independently selected from H, OH, straight or branched $C_1$-$C_5$ alkyl, straight or branched $C_1$-$C_5$alkoxy, —NH$_3$, straight or branched $C_1$-$C_5$ amine;

$R_{10}$ is selected from H, a straight or branched $C_1$-$C_5$ alkyl; and $R_{11}$ and $R_{12}$ are independently selected from H, OH, straight or branched $C_1$-$C_5$ alkyl, straight or branched $C_1$-$C_5$ alkoxy, —NH$_3$, straight or branched $C_1$-$C_5$ amine;

$R_{13}$, $R_{14}$, $R_{15}$, $R_{16}$ and $R_{17}$ are each optionally selected from H and F;

provided that at least one of $R_{13}$, $R_{14}$, $R_{15}$ and $R_{16}$ is F or $R_1$ is substituted with F.

In another aspect of the present disclosure, the F-CBD is a compound having the general formula (IIa):

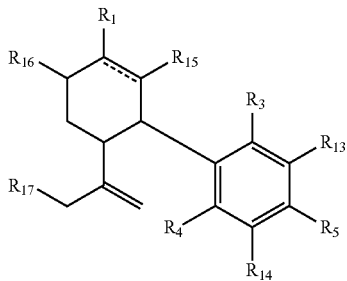

(IIa)

wherein

═══ is a single or double bond;

$R_1$ is selected from straight or branched $C_1$-$C_8$ alkyl, straight or branched $C_2$-$C_{10}$ alkenyl, straight or branched $C_2$-$C_{10}$ alkynyl, —C(═O)$R_8$, —C(═O)O$R_9$ each optionally substituted by at least one F;

$R_3$ and $R_4$ are each independently selected from H, straight or branched $C_1$-$C_5$ alkyl, —O$R_{10}$, —C(═O)$R_{11}$, —OC(═O)$R_{12}$; provided that at least one of $R_3$ and $R_4$ is different than H;

$R_5$ is selected from a straight or branched $C_5$ alkyl, each being optionally substituted by at least one substituent selected from —OH, —NH$_3$, straight or branched $C_1$-$C_5$ amine, halogen, phenyl, aryl, heteroaryl, cycloalkyl and heterocycloalkyl;

$R_8$, and $R_9$ are independently selected from H, OH, straight or branched $C_1$-$C_5$ alkyl, straight or branched $C_1$-$C_5$alkoxy, —NH$_3$, straight or branched $C_1$-$C_5$ amine;

$R_{10}$ is selected from H, a straight or branched $C_1$-$C_5$ alkyl; and $R_{11}$ and $R_{12}$ are independently selected from H, OH, straight or branched $C_1$-$C_5$ alkyl, straight or branched $C_1$-$C_5$ alkoxy, —NH$_3$, straight or branched $C_1$-$C_5$ amine;

$R_{13}$, $R_{14}$, $R_{15}$, $R_{16}$ and $R_{17}$ are each optionally selected from H and F;

provided that at least one of $R_{13}$, $R_{14}$, $R_{15}$ and $R_{16}$ is F or $R_1$ is substituted with F.

In another aspect of the present disclosure, the F-CBD is a compound having the general formula (III):

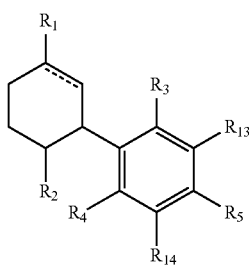

(III)

wherein

═══ is a single or double bond;

$R_1$ is selected from straight or branched $C_1$-$C_8$ alkyl, straight or branched $C_2$-$C_{10}$ alkenyl, straight or branched $C_2$-$C_{10}$ alkynyl, —C(═O)$R_8$, —C(═O)O$R_9$;

$R_2$ is selected from straight or branched C1-C8 alkyl, straight or branched C2-C10 alkenyl, straight or branched C2-C10 alkynyl;

R3 and R4 are each independently selected from H, straight or branched C1-C5 alkyl, —OR10, —C(═O)R11, —OC(═O)R12; provided that at least one of R3 and R4 is different than H;

R5 is selected from a straight or branched C5-C12 alkyl, a straight or branched C5-C9 alkoxy, a straight or branched C1-C7 ether, each being optionally substituted by at least one substituent selected from —OH, —NH3, straight or branched C1-C5 amine, halogen, phenyl, aryl, heteroaryl, cycloalkyl and heterocycloalkyl;

R8, and R9 are independently selected from H, OH, straight or branched C1-C5 alkyl, straight or branched C1-C5 alkoxy, —NH3, straight or branched C1-C5 amine;

R10 is selected from H, a straight or branched C1-C5 alkyl; and

R11 and R12 are independently selected from H, OH, straight or branched C1-C5 alkyl, straight or branched C1-C5 alkoxy, —NH3, straight or branched C1-C5 amine;

R13 and R14 are each optionally selected from H and F; provided that at least one of R13 and R14 are F.

In another aspect of the present disclosure, the F-CBD is a compound having the general formula (IIIa):

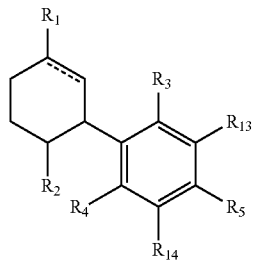

(IIIa)

wherein

═══ is a single or double bond;

$R_1$ is selected from straight or branched $C_1$-$C_8$ alkyl, straight or branched $C_2$-$C_{10}$ alkenyl, straight or branched $C_2$-$C_{10}$ alkynyl, —C(═O)$R_8$, —C(═O)O$R_9$;

$R_2$ is selected from straight or branched $C_1$-$C_8$ alkyl, straight or branched $C_2$-$C_{10}$ alkenyl, straight or branched $C_2$-$C_{10}$ alkynyl;

$R_3$ and $R_4$ are each independently selected from H, straight or branched $C_1$-$C_5$ alkyl, —O$R_{10}$, —C(═O)$R_{11}$, —OC(═O)$R_{12}$; provided that at least one of $R_3$ and $R_4$ is different than H;

$R_5$ is selected from a straight or branched $C_5$ alkyl, each being optionally substituted by at least one substituent selected from —OH, —NH$_3$, straight or branched $C_1$-$C_5$ amine, halogen, phenyl, aryl, heteroaryl, cycloalkyl and heterocycloalkyl;

$R_8$, and $R_9$ are independently selected from H, OH, straight or branched $C_1$-$C_5$ alkyl, straight or branched $C_1$-$C_5$alkoxy, —NH$_3$, straight or branched $C_1$-$C_5$ amine;

$R_{10}$ is selected from H, a straight or branched $C_1$-$C_5$ alkyl; and $R_{11}$ and $R_{12}$ are independently selected from H, OH, straight or branched $C_1$-$C_5$ alkyl, straight or branched $C_1$-$C_5$ alkoxy, —NH$_3$, straight or branched $C_1$-$C_5$ amine;

$R_{13}$ and $R_{14}$ are each optionally selected from H and F; provided that at least one of $R_{13}$ and $R_{14}$ are F.

In another aspect of the present disclosure, the F-CBD is a compound having the general formula (IV)

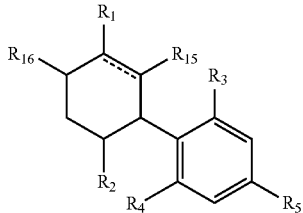

(IV)

wherein

═══ is a single or double bond;

$R_1$ is selected from straight or branched $C_1$-$C_8$ alkyl, straight or branched $C_2$-$C_{10}$ alkenyl, straight or branched $C_2$-$C_{10}$ alkynyl, —C(═O)$R_8$, —C(═O)O$R_9$ each optionally substituted by at least one F;

$R_2$ is selected from straight or branched $C_1$-$C_8$ alkyl, straight or branched $C_2$-$C_{10}$ alkenyl, straight or branched $C_2$-$C_{10}$ alkynyl, each optionally substituted by at least one F;

$R_3$ and $R_4$ are each independently selected from H, straight or branched $C_1$-$C_5$ alkyl, —O$R_{10}$, —C(═O)$R_{11}$, —OC(═O)$R_{12}$; provided that at least one of $R_3$ and $R_4$ is different than H;

$R_5$ is selected from a straight or branched $C_5$-$C_{12}$ alkyl, a straight or branched $C_5$-$C_9$ alkoxy, a straight or branched $C_1$-$C_7$ ether, each being optionally substituted by at least one substituent selected from —OH, —NH$_3$, straight or branched $C_1$-$C_5$ amine, halogen, phenyl, aryl, heteroaryl, cycloalkyl and heterocycloalkyl;

$R_8$, and $R_9$ are independently selected from H, OH, straight or branched $C_1$-$C_5$ alkyl, straight or branched $C_1$-$C_5$alkoxy, —NH$_3$, straight or branched $C_1$-$C_5$ amine;

$R_{10}$ is selected from H, a straight or branched $C_1$-$C_5$ alkyl; and $R_{11}$ and $R_{12}$ are independently selected from H, OH, straight or branched $C_1$-$C_5$ alkyl, straight or branched $C_1$-$C_5$ alkoxy, —NH$_3$, straight or branched $C_1$-$C_5$ amine;

$R_{15}$ and $R_{16}$ are each optionally selected from H and F;

provided that at least one of $R_{15}$ and $R_{16}$ is F or at least one of $R_1$ and $R_2$ is substituted with F.

In another aspect of the present disclosure, the F-CBD is a compound having the general formula (IVa)

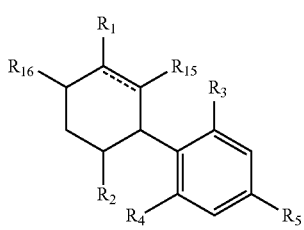

(IVa)

wherein

═══ is a single or double bond;

$R_1$ is selected from straight or branched $C_1$-$C_8$ alkyl, straight or branched $C_2$-$C_{10}$ alkenyl, straight or branched $C_2$-$C_{10}$ alkynyl, —C(═O)$R_8$, —C(═O)O$R_9$ each optionally substituted by at least one F;

$R_2$ is selected from straight or branched $C_1$-$C_8$ alkyl, straight or branched $C_2$-$C_{10}$ alkenyl, straight or branched $C_2$-$C_{10}$ alkynyl, each optionally substituted by at least one F;

$R_3$ and $R_4$ are each independently selected from H, straight or branched $C_1$-$C_5$ alkyl, —O$R_{10}$, —C(═O)$R_{11}$, —OC(═O)$R_{12}$; provided that at least one of $R_3$ and $R_4$ is different than H;

$R_5$ is selected from a straight or branched $C_5$ alkyl, each being optionally substituted by at least one substituent selected from —OH, —NH$_3$, straight or branched $C_1$-$C_5$ amine, halogen, phenyl, aryl, heteroaryl, cycloalkyl and heterocycloalkyl;

$R_8$, and $R_9$ are independently selected from H, OH, straight or branched $C_1$-$C_5$ alkyl, straight or branched $C_1$-$C_5$alkoxy, —NH$_3$, straight or branched $C_1$-$C_5$ amine;

$R_{10}$ is selected from H, a straight or branched $C_1$-$C_5$ alkyl; and $R_{11}$ and $R_{12}$ are independently selected from H, OH, straight or branched $C_1$-$C_5$ alkyl, straight or branched $C_1$-$C_5$ alkoxy, —NH$_3$, straight or branched $C_1$-$C_5$ amine;

$R_{15}$ and $R_{16}$ are each optionally selected from H and F;

provided that at least one of $R_{15}$ and $R_{16}$ is F or at least one of $R_1$ and $R_2$ is substituted with F.

In some embodiments ═══ is a double bond.

In some other embodiments $R_1$ straight or branched $C_1$-$C_8$ alkyl; $R_3$ and $R_4$ are each independently —O$R_{10}$; $R_{10}$ is selected from H, a straight or branched $C_1$-$C_5$ alkyl.

In further embodiments $R_1$ is straight or branched $C_1$-$C_8$ alkyl, and $R_3$ and $R_4$ are OH.

In other embodiments, $R_3$ and $R_4$ are each independently selected from H, —O$R_{10}$, and —OC(═O)$R_{12}$; $R_{10}$ is selected from H, a straight or branched $C_1$-$C_5$ alkyl; and $R_{12}$ is selected from H, OH, straight or branched $C_1$-$C_5$ alkyl, —NH$_3$, straight or branched $C_1$-$C_5$ amine.

In some embodiments, $R_5$ is a straight or branched $C_5$-$C_{12}$ alkyl.

In some embodiments, $R_5$ is a straight or branched $C_5$ alkyl.

In further embodiments, the F-CBD is a compound wherein at least one of $R_{13}$, $R_{14}$, $R_{15}$ and $R_{16}$ is F.

In other embodiments, the F-CBD is a compound wherein at least one of $R_{13}$ and $R_{14}$ is F.

In further embodiments, the F-CBD is a compound wherein at least one of $R_{15}$ and $R_{16}$ is F.

In other embodiments, the F-CBD is a compound wherein at least one of $R_1$ and $R_2$ is substituted with F.

In yet further embodiments, the F-CBD is a compound wherein $R_1$ is selected from straight or branched $C_1$-$C_8$ alkyl, straight or branched $C_2$-$C_{10}$ alkenyl, straight or branched $C_2$-$C_{10}$ alkynyl, each being substituted by F.

In further embodiments, the F-CBD is a compound wherein $R_2$ is selected from straight or branched $C_1$-$C_8$ alkyl, straight or branched $C_2$-$C_{10}$ alkenyl, straight or branched $C_2$-$C_{10}$ alkynyl, each substituted by F.

In further embodiments, the F-CBD is a compound of the general formula (V):

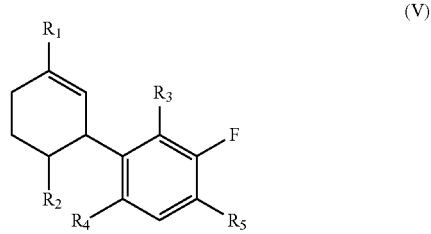

(V)

wherein $R_1$, $R_2$, $R_3$, $R_4$ and $R_5$ are as defined therein.

In one embodiment, $R_5$ is a straight or branched $C_5$-$C_{12}$ alkyl in formula (V).

In another embodiment, $R_5$ is a straight or branched $C_5$ alkyl in formula (V).

In other embodiments, the F-CBD is a compound of the general formula (VI):

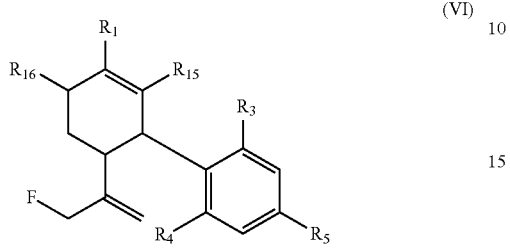

(VI)

wherein $R_1$, $R_3$, $R_4$, $R_5$, $R_{15}$ and $R_{16}$ are as defined therein.

In one embodiment, $R_5$ is a straight or branched $C_5$-$C_{12}$ alkyl in formula (VI).

In another embodiment, $R_5$ is a straight or branched $C_5$ alkyl in formula (VI).

In other embodiments, the F-CBD is a compound having the general formula (I):

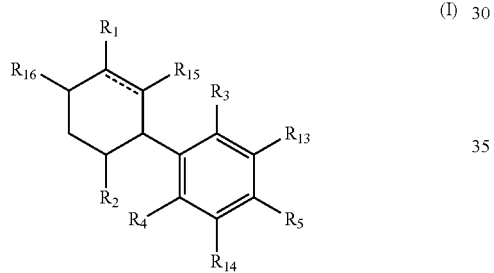

(I)

wherein

═ is a double bond;

$R_1$ is a straight or branched $C_1$-$C_8$ alkyl optionally substituted by at least one F;

$R_2$ is a straight or branched $C_2$-$C_{10}$ alkenyl optionally substituted by at least one F;

$R_3$ and $R_4$ are each independently selected from H, —$OR_{10}$, —OC(═O)$R_{12}$; provided that at least one of $R_3$ and $R_4$ is different than H;

$R_5$ is a straight or branched $C_5$-$C_{12}$ alkyl optionally substituted by at least one substituent selected from —OH, —$NH_3$, straight or branched $C_1$-$C_5$ amine, halogen, phenyl, aryl, heteroaryl, cycloalkyl and heterocycloalkyl;

$R_{10}$ is selected from H, a straight or branched $C_1$-$C_5$ alkyl; and $R_{12}$ is selected from H, OH, straight or branched $C_1$-$C_5$ alkyl, straight or branched $C_1$-$C_5$ alkoxy, —$NH_3$, straight or branched $C_1$-$C_5$ amine;

$R_{13}$, $R_{14}$, $R_{15}$ and $R_{16}$ are each optionally selected from H and F;

provided that at least one of $R_{13}$, $R_{14}$, $R_{15}$ and $R_{16}$ is F or at least one of $R_1$ and $R_2$ is substituted with F.

In other embodiments, the F-CBD is a compound having the general formula (Ia):

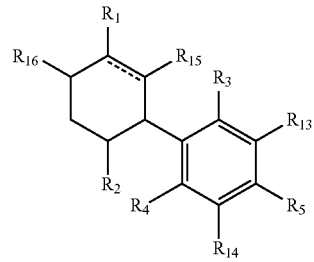

(Ia)

wherein

═ is a double bond;

$R_1$ is a straight or branched $C_1$-$C_8$ alkyl optionally substituted by at least one F;

$R_2$ is a straight or branched $C_2$-$C_{10}$ alkenyl optionally substituted by at least one F;

$R_3$ and $R_4$ are each independently selected from H, —$OR_{10}$, —OC(═O)$R_{12}$; provided that at least one of $R_3$ and $R_4$ is different than H;

$R_5$ is a straight or branched $C_5$ alkyl optionally substituted by at least one substituent selected from —OH, —$NH_3$, straight or branched $C_1$-$C_5$ amine, halogen, phenyl, aryl, heteroaryl, cycloalkyl and heterocycloalkyl;

$R_{10}$ is selected from H, a straight or branched $C_1$-$C_5$ alkyl; and $R_{12}$ is selected from H, OH, straight or branched $C_1$-$C_5$ alkyl, straight or branched $C_1$-$C_5$ alkoxy, —$NH_3$, straight or branched $C_1$-$C_5$ amine;

$R_{13}$, $R_{14}$, $R_{15}$ and $R_{16}$ are each optionally selected from H and F;

provided that at least one of $R_{13}$, $R_{14}$, $R_{15}$ and $R_{16}$ is F or at least one of $R_1$ and $R_2$ is substituted with F.

The disclosure provides embodiments where the F-CBD is a compound having the formula:

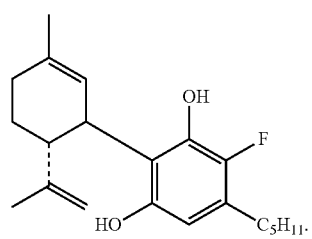

The disclosure provides embodiments where the F-CBD is a compound having the formula:

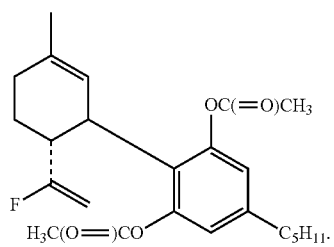

The disclosure further provides embodiments where the F-CBD is a compound having the formula:

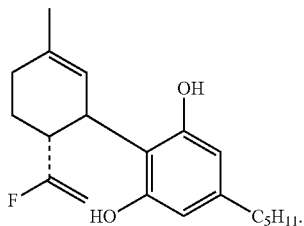

The disclosure further provides embodiments where the F-CBD is a compound having the formula:

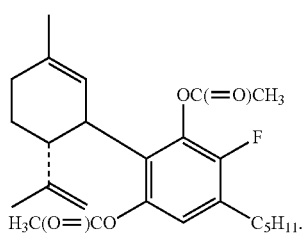

The disclosure provides embodiments where the F-CBD is a compound having the formula:

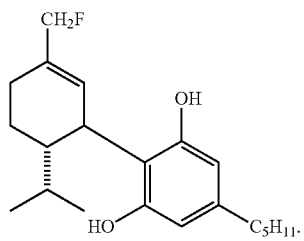

The disclosure provides embodiments where the F-CBD is a compound having the formula:

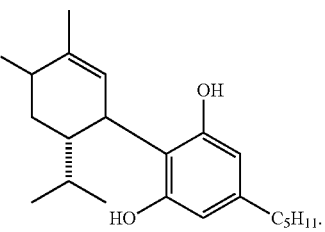

The disclosure provides embodiments where the F-CBD is a compound having the formula:

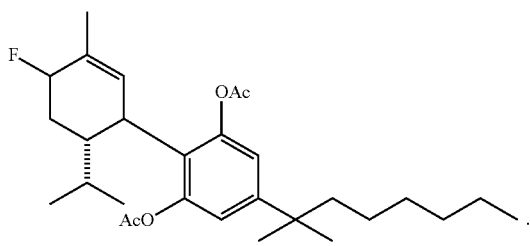 [SMILES: CCCCCCC(C)(C)c1cc(OC(C)=O)c(C2C=C(C)C(F)C[C@H]2C(C)C)c(OC(C)=O)c1]

The disclosure provides embodiments where the F-CBD is a compound having the formula:

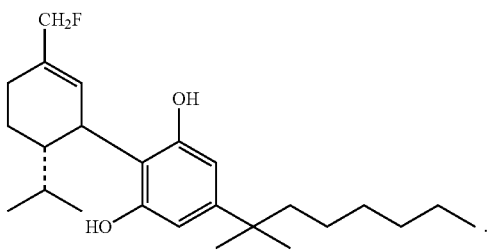

The disclosure provides embodiments where the F-CBD is a compound having the formula:

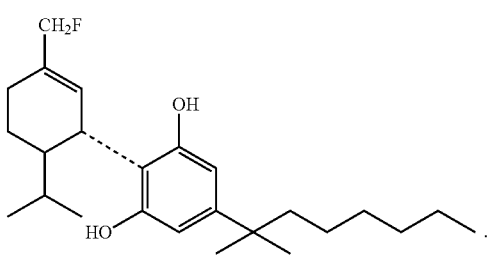

The disclosure provides embodiments where the F-CBD is a compound having the formula:

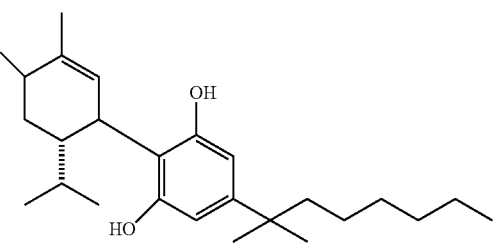

The term "active ingredient" as used herein refers to a botanical drug substance derived from a cannabis plant that produces a desired biological effect. For example, active ingredients of the pharmaceutical compositions described herein include, but are not limited to, cannabinoids, phytocannabinoids (including THC and CBD), cannabinoic acids, terpenes (including BCP), terpenoids, cannabinoid receptor agonists (including CB1 and CB2 agonists). Furthermore, active ingredients of the pharmaceutical compositions described herein include prodrugs and semi-synthetic fluorinated derivatives (such as F-CBDs).

The term "substantially pure" or "substantially pure active ingredient(s)" means preparations of any one of the active ingredients having a chromatographic purity (of the active ingredient) of greater than about 95%. In some embodiments, the chromatographic purity is greater than 96%. In some embodiments, the chromatographic purity is greater than about 97%. In some embodiments, the chromatographic purity is greater than about 98%. In some embodiments, the chromatographic purity is greater than about 99%. In some embodiments, the chromatographic purity is greater than about 99.5%. In some embodiments the purity is determined by area normalization of an HPLC or GC-FID profile. Thus, in some embodiments, the present disclosure provides "substantially pure THC," "substantially pure CBD," and/or "substantially pure (E)-BCP", as well as mixtures these substantially pure active ingredients.

The term "enriched" or "enriched active ingredient(s)" means preparations of any one of the active ingredients having a chromatographic purity (of the active ingredient) of greater than about 80%. In some embodiments, the chromatographic purity is greater than 85%. In some embodiments, the chromatographic purity is greater than about 90%. An enriched preparation of a active ingredient(s) will generally contain a greater proportion of impurities and/or other cannabinoids than a substantially pure preparation of the same active ingredient(s), as described above. In some embodiments, the term is used to refer to the combination of all active ingredients. In other embodiments, the term is used to refer to one or more enriched active ingredients, either generally, or specifically by reciting the name of the ingredient. Thus, in some embodiments, the present disclosure provides "enriched THC," "enriched CBD," and/or "enriched (E)-BCP."

The purity of different active ingredients (e.g. cannabinoids or cannabinoid acids, such as THC and CBD, or terepenes such as (E)-BCP) may be enhanced by selection of appropriate starting plant material. By way of example, if it is desired to prepare substantially pure 49 THC or 49 THCA, then "high THC" cannabis plants can be selected as the starting material. Similarly, if it is desired to prepare substantially pure CBD or CBDA then "high CBD" cannabis plants can be selected as the starting material. However, it is to be understood that the process of the invention is of general utility and is not limited to the use of particular cannabis varieties as the starting material.

The term "botanical drug substance" as used herein refers to the definition provided in the Guidance for Industry Botanical Drug Products Draft Guidance, August 2000, US Department of Health and Human Services, Food and Drug Administration Centre for Drug Evaluation and Research of: "A drug substance derived from one or more plants, algae, or macroscopic fungi. It is prepared from botanical raw materials by one or more of the following processes: pulverization, decoction, expression, aqueous extraction, ethanolic extraction, or other similar processes." Botanical drug substances derived from cannabis plants include primary extracts prepared by such processes as, for example, maceration, percolation, and solvent extraction. Solvent extraction may be carried out using essentially any solvent that dissolves cannabinoids/cannabinoid acids, such as for example C1 to C5 alcohols (e.g. ethanol, methanol), C5-C12 alkanes (e.g. hexane), Norflurane (HFA134a), HFA227 and carbon dioxide. When solvents such as those listed above are used, the resultant extract typically contains non-specific lipid-soluble material. This can be removed by a variety of processes including "winterization", which involves chilling to −20° C. followed by filtration to remove waxy ballast, extraction with liquid carbon dioxide and by distillation. General protocols for the preparation of botanical drug substances from cannabis plant material are described in U.S. Pat. No. 6,730,330.

In some embodiments, the botanical drug substance may be obtained by carbon dioxide ($CO_2$) extraction followed by a secondary extraction, e.g. an ethanolic precipitation, to remove a substantial proportion of non-cannabinoid materials, e.g. waxes, wax esters and glycerides, unsaturated fatty acid residues, terpenes, carotenes, and flavonoids and other ballast. In some embodiments, the botanical drug substance is produced by a process comprising extraction with liquid $CO_2$, under sub-critical or super-critical conditions, and then a further extraction (e.g., an ethanolic precipitation) to remove significant amounts of ballast. If it is intended to prepare free cannabinoids from the cannabis plant material, then the material is preferably heated to a defined temperature for a defined period of time in order to decarboxylate cannabinoid acids to free cannabinoids prior to extraction of the botanical drug substance.

In some embodiments, the botanical drug substance is prepared according to a process comprising the following steps: i) optional decarboxylation of the plant material, ii) extraction with liquid $CO_2$ (in some embodiments under sub-critical conditions), to produce a crude botanical drug substance, iii) precipitation with C1-C5 alcohol to reduce the proportion of non-target materials, iv) removal of the precipitate (preferably by filtration), v) optional treatment with activated charcoal, and vi) evaporation to remove C1-C5 alcohol and water, thereby producing a final botanical drug substance. Extraction techniques for cannabinoids can be found in U.S. Published Patent Application No. 2005/0266108.

The term "active ingredient portion" as used herein refers to the portion of a pharmaceutical composition that accounts for all active ingredients. In some embodiments, the active ingredient portion of the pharmaceutical compositions described herein comprises one or more active ingredients. For example, the active ingredient portion may include a substantially pure active ingredient; an enriched active ingredient or mixtures thereof. In some embodiments, the active ingredient portion comprises one or more active ingredients and one or more additional active ingredients that are not derived from a cannabis plant, such as one or more other drugs.

The term "sample" refers to a biological specimen comprising one or more cells that is subjected to analysis. Samples may comprise various forms of biological materials including tissue, fluid, and cellular suspensions. In some embodiments, a tissue sample may be derived from any tissue type including, but not limited to skin, hair (including roots), bone marrow, bone, muscle, salivary gland, esophagus, stomach, small intestine (e.g., tissue from the duodenum, jejunum, or ileum), large intestine, liver, gallbladder, pancreas, lung, kidney, bladder, uterus, ovary, vagina, placenta, testes, thyroid, adrenal gland, cardiac tissue, thymus, spleen, lymph node, spinal cord, brain, eye, ear, tongue, cartilage, white adipose tissue, or brown adipose tissue. In some embodiments, a fluid sample comprises buccal swabs, blood, plasma, oral mucous, vaginal mucous, peripheral blood, cord blood, saliva, semen, urine, ascites fluid, pleural fluid, spinal fluid, pulmonary lavage, tears, sweat, semen, seminal fluid, seminal plasma, prostatic fluid, pre-ejaculatory fluid (Cowper's fluid), excreta, cerebrospinal fluid, lymph, cell culture media comprising one or more populations of cells, buffered solutions comprising one or more populations of cells, and the like. The term sample includes "primary samples" that it are obtained directly from a subject and samples that are the result of processing of a primary sample, for example to remove certain components and/or to isolate or purify certain components of interest. For example, in some embodiments, a sample is processed to enrich or purify a particular cell type from the remainder of the sample.

The terms "therapeutically effective amount" and "therapeutically effective dose" are used interchangeably herein and refer to the minimum amount of an active ingredient portion of a pharmaceutical composition required to result in a particular physiological effect (e.g., an amount required to increase, activate, enhance, decrease, or inhibit a particular physiological effect).

A "population of cells" refers to any number of cells greater than 1, but is preferably at least $1\times10^3$ cells, at least $1\times10^4$ cells, at least at least $1\times10^5$ cells, at least $1\times10^6$ cells, at least $1\times10^7$ cells, at least $1\times10^8$ cells, at least $1\times10^9$ cells, at least $1\times10^{10}$ cells, or more cells. A population of cells can refer to an in vitro population (e.g., a population of cells in culture) or an in vivo population (e.g., a population of cells residing in a particular tissue).

"Decrease" or "reduce" refers to a decrease or a reduction in a particular value by at least 5%, for example, by at least 5, 6, 7, 8, 9, 10, 15, 20, 25, 30, 35, 40, 45, 50, 55, 60, 65, 70, 75, 80, 85, 90, 95, 99 or 100% as compared to a reference value. A decrease or reduction in a particular value may also be represented as a fold-change in the value compared to a reference value, for example, a fold decrease of at least 1, 2, 3, 4, 5, 6, 7, 8, 9, 10, 15, 20, 30, 40, 50, 60, 70, 80, 90, 100, 200, 500, 1000-fold, or more, as compared to a reference value.

"Increase" refers to an increase in a particular value of at least 5%, for example, at least 5, 6, 7, 8, 9, 10, 15, 20, 25, 30, 35, 40, 45, 50, 55, 60, 65, 70, 75, 80, 85, 90, 95, 99, 100, 200, 300, 400, 500% or more as compared to a reference value. An increase in a particular value may also be represented as a fold-change in the value compared to a reference value, for example, a fold increase of at least 1-fold, 2, 3, 4, 5, 6, 7, 8, 9, 10, 15, 20, 30, 40, 50, 60, 70, 80, 90, 100, 200, 500, 1000-fold or more, increase as compared to the level of a reference value.

The term "reference value" or "control value" refers to a value or measurement obtained from an experimental control group (e.g., vehicle treated or untreated control values) or to a baseline value obtained from a sample or subject before treatment that is then compared to a value obtained from the sample or subject after treatment.

"Treating" as used herein with regard to a patient, refers to improving at least one symptom of the patient's disorder. Treating can be curing, improving, or at least partially ameliorating a disorder.

II. Cannabinoids

In some embodiments, the present disclosure provides pharmaceutical compositions comprising one or more cannabinoids. Cannabinoids are a class of diverse chemical compounds that activate cannabinoid receptors in the human brain, peripheral nervous system, and immune system (Mackie K. 2008 "Cannabinoid receptors: where are they and what they do" J. Neuroendocrinol. May 20: 1:10-4). Cannabinoids can be broadly categorized into endocannabinoids, which are endogenously produced compounds in humans and other animals, such as 2-Arachidonoylglycerol, and phytocannabinoids, which are cannabinoid mimetic compounds produced by plants.

One of the best-known sources of phytocannabinoids is plants from the *Cannabis* genus. At least 85 different cannabinoids have been isolated from the cannabis plants (El-Alfy et al., 2010, "Antidepressant-like effect of delta-9-tetrahydrocannabinol and other cannabinoids isolated from *Cannabis sativa* L", Pharmacology Biochemistry and Behavior 95 (4): 434-42; Brenneisen, supra). Typical cannabinoids isolated from *Cannabis* plants include, but are not limited to, Tetrahydrocannabinol (THC), Cannabidiol (CBD), Cannabigerol (CBG), Cannabichromene (CBC), Cannabicyclol (CBL), Cannabivarin (CBV), Tetrahydrocannabivarin (THCV), Cannabidivarin (CBDV), Cannabichromevarin (CBCV), Cannabigerovarin (CBGV), and Cannabigerol Monomethyl Ether (CBGM). (See Holley et al., Constituents of *Cannabis sativa* L. XI Cannabidiol and cannabichromene in samples of known geographical origin, J. Pharm. Sci. 64:892-894, 1975; and De Zeeuw et al., Cannabinoids with a propyl side chain in *Cannabis*, Occurrence and chromatographic behavior, Science 175:778-779, each of which is herein incorporated by reference in its entirety for all purposes).

Phytocannabinoids are the most studied group of secondary metabolites in *cannabis*. Most exist in two forms: an acid form and a neutral (decarboxylated) form. The phytocannabinoids are synthesized in the plant as acid forms, which are designated by an "A" at the end of the acronym (i.e. CBDA or THCA). The biologically active form of phytocannabinoids suitable for human consumption is the neutral form. While some decarboxylation (e.g., neutralization) of phytocannabinoids does occur in the plant, production of the neutral forms increase significantly post-harvest with increases in temperature. (Sanchez and Verpoorte 2008 "PKS activities and biosynthesis of cannabinoids and flavonoids in *Cannabis sativa* L. plants" Plant Cell Physiol. December: 49(12)). Decarboxylation is usually achieved by thorough drying of the plant material followed by heating it, often by either combustion, vaporization, or heating or baking in an oven. Unless otherwise noted, references to cannabinoids in this disclosure refer to the "active" decarboxylated versions of the molecules (e.g., CBD or THC).

The two cannabinoids usually produced in greatest abundance are cannabidiol (CBD) and/or $\Delta^9$-tetrahydrocannabinol (THC). THC is a psychoactive compound and produces the "high" associated with marijuana consumption. CBD has no known recreational "high" effects, but has recently been associated with many medical benefits. See, ElSohly, ed. "Marijuana and the Cannabinoids," Humana Press Inc., 321 papers, 2007, which is incorporated herein by reference in its entirety, for a detailed description and literature review on the cannabinoids found in *cannabis*.

A. Cannabidiol

Formula I

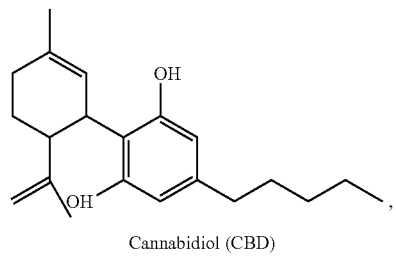

Cannabidiol (CBD)

In some embodiments, the present disclosure provides pharmaceutical compositions comprising one or more cannabinoids, wherein the one or more cannabinoids comprises cannabidiol (CBD).

CBD is an antagonist of the putative new cannabinoid receptor, GPR55, and has also been shown to act as a 5-HT1A receptor agonist, an action which may result in CBD's antidepressant, anxiolytic, and neuroprotective effects. Cannabidiol is also an allosteric modulator at the Mu and Delta opioid receptor sites. Further, CBD has been shown to interact with $CB_2$ receptors located in the periphery of the nervous system and in lymphoid tissues (Showalter V M et al., 1996 "Evaluation of binding in a transfected cell line expressing a peripheral cannabinoid receptor (CB2): identification of cannabinoid receptor subtype selective ligands." J Pharmacol Exp Ther 278(3):989-999; and RG Pertwee 2008 "The diverse CB1 and CB2 receptor pharmacology of three plant cannabinoids: delta9-tetrahydrocannabinol, cannabidiol and delta9 tetrahydrocannabivarin" Br. J Pharmacol 153(2)). Thus in some embodiments, CBD is a weak $CB_2$ agonist, with binding affinities lower than THC. In other embodiments, CBD is a $CB_2$ inverse agonist. That is, in some embodiments, CBD may inhibit or modulate the binding of other agonists to their target cannabinoid receptors.

Cannabis produces CBD-carboxylic acid (CBDA) through the same metabolic pathway as THC, until the last step, where CBDA synthase performs the catalysis instead of THCA synthase. See Marks et al. (2009, "Identification of candidate genes affecting Δ9-tetrahydrocannabinol biosynthesis in *Cannabis sativa*", Journal of Experimental Botany 60 (13): 3715-3726) and Meijer et al. I, II, III, and IV.

CBD has recently garnered attention for its potential as a pharmaceutical drug. CBD has been shown to relieve convulsion, inflammation, anxiety, neuropathic pain and nausea, as well as inhibit cancer cell growth (Mechoulam, et al., 2007, "Cannabidiol—recent advances". *Chemistry & Biodiversity* 4 (8): 1678-1692; Costa, et al., 2007, "The non-psychoactive cannabis constituent cannabidiol is an orally effective therapeutic agent in rat chronic inflammatory and neuropathic pain" *European J. Pharmacology*, 556, 75-83). Recent studies have shown cannabidiol to be as effective as atypical antipsychotics in treating schizophrenia (Zuardi et al., 2006, "Cannabidiol, a *Cannabis sativa* constituent, as an antipsychotic drug" Braz. *J. Med. Biol. Res.* 39 (4): 421-429.). Studies have also shown that it may relieve symptoms of dystonia (Consroe, 1986, "Open label evaluation of cannabidiol in dystonic movement disorders". *The International journal of neuroscience* 30 (4): 277-282; Snider et al., 1985, "Beneficial and Adverse Effects of Cannabidiol in a Parkinson Patient with Sinemet-Induced Dystonic Dyskinesia". *Neurology*, (Suppl 1): 201). CBD has also been shown to reduce the growth of aggressive human breast cancer cells in vitro and reduces their invasiveness (McAllister et al., 2007, "Cannabidiol as a novel inhibitor of Id-1 gene expression in aggressive breast cancer cells". *Mol. Cancer Ther.* 6 (11): 2921-7).

Cannabidiol has shown to decrease activity of the limbic system (de Souza Crippa et al., "Effects of Cannabidiol (CBD) on Regional Cerebral Blood Flow". *Neuropsychopharmacology* 29 (2): 417-426) and to decrease social isolation induced by THC (Malon et al., "Cannabidiol reverses the reduction in social interaction produced by low dose $A^9$-tetrahydrocannabinol in rats". Pharmacology Biochemistry and Behavior 93 (2): 91-96). It's also shown that cannabidiol reduces anxiety in social anxiety disorder (Bergamaschi et al., 2003, "Cannabidiol Reduces the Anxiety Induced by Simulated Public Speaking in Treatment-Naïve Social Phobia Patients". *Neuropsychopharmacology* 36 (6): 1219-1226).

Despite its impressive list of potential medical applications, as of the filing of this application, there are no FDA approved CBD-based medicines in the United States. One of the concerns of CBD-based pharmaceuticals is the high dosage required to produce an effect. In murine studies, CBD anti-depressant effects require administrations of upwards of 30 mg/kg of CBD per day (Zanelati et al., 2010 "Antidepressant-like effects of cannabidiol in mice: possible involvement of 5-HT1A receptors" Br J Pharmacol 149(1): 122-128). GW Pharmaceutical's CBD-based Epidiolex is similarly being tested up to 50 mg/kg dosages for controlling epileptic symptoms (see Clinical Trials.gov identifier NCT02397863). For a normal 200 lb adult, this level of dosing translates to roughly 4.5 gram dosing per day.

Efforts at improving the efficacy of CBD have resulted in dosing reductions through drug modifications. For example, the recent development of fluorinated CBD variants resulted in 10× dosage reductions in a variety of mouse models (see U.S. Pat. No. 9,447,019, hereby incorporated by reference in its entirety).

In some embodiments, the pharmaceutical compositions of the present disclosure comprise decarboxylated pentyl cannabidiol (i.e. the molecule of Formula I). In other embodiments, the pharmaceutical compositions of the present disclosure comprise CBD variants, including, but not limited to F-CBD, CBD monomethyl ether (Formula II), Cannabidiol-C4 (Formula III), (−)-Cannabidivarin (Formula IV), or Cannabidiorcol (Formula V). In some embodiments, the pharmaceutical compositions described herein comprise F-CBD. Non-limiting examples of CBD variants include:

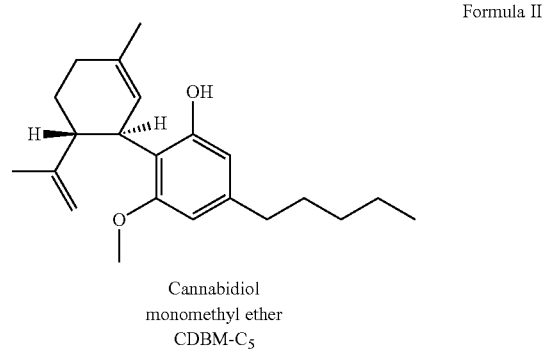

Formula II

Cannabidiol monomethyl ether
CDBM-$C_5$

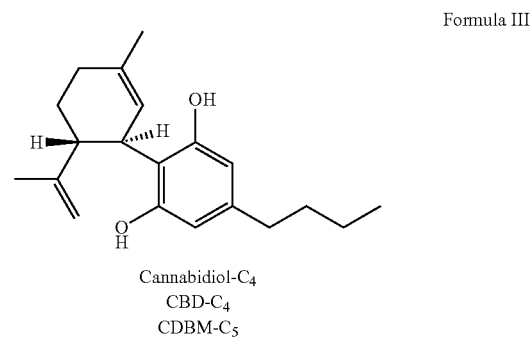

Formula III

Cannabidiol-$C_4$
CBD-$C_4$
CDBM-$C_5$

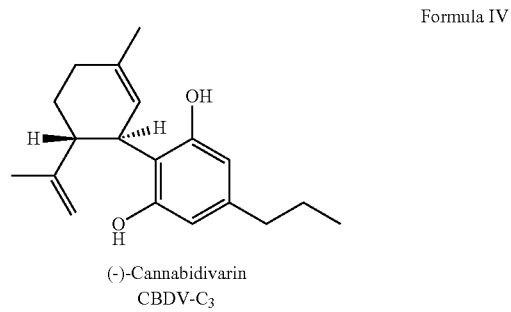

Formula IV (−)-Cannabidivarin
CBDV-$C_3$

Formula V

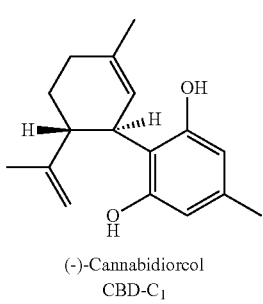

(-)-Cannabidiorcol
CBD-C$_1$

Formula VI

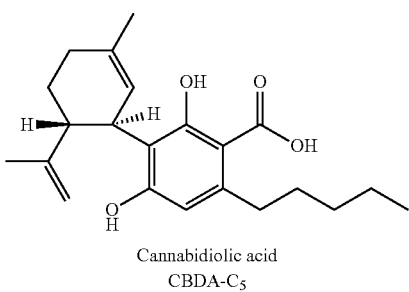

Cannabidiolic acid
CBDA-C$_5$

Formula VII

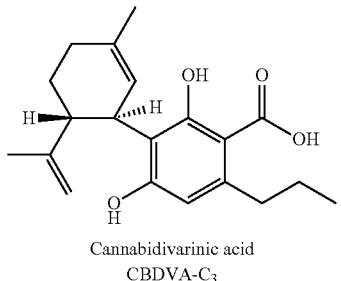

Cannabidivarinic acid
CBDVA-C$_3$

B. Tetrahydrocannabinol

Formula II

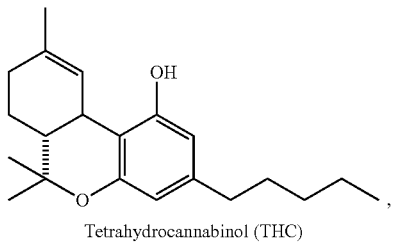

Tetrahydrocannabinol (THC)

In some embodiments, the present disclosure provides pharmaceutical compositions comprising one or more cannabinoids, wherein the one or more cannabinoids comprises tetrahydrocannabinol (THC, also known as delta-9-tetrahydrocannabinol (Δ9-THC), shown in Formula II).

THC is the principal psychoactive constituent of the cannabis plant and is initially synthesized and accumulates in the plant as tetrahydrocannabinolic acid (THCA, 2-COOH-THC). Geranyl pyrophosphate and olivetolic acid react, catalyzed by an enzyme to produce cannabigerolic acid, which is cyclized by the enzyme THC acid synthase to give THCA. Over time, or when heated, THCA is decarboxylated producing THC. The pathway for THCA biosynthesis is similar to that which produces the bitter acid humulone in hops. See Fellermeier et al., (1998, "Prenylation of olivetolate by a hemp transferase yields cannabigerolic acid, the precursor of tetrahydrocannabinol". *FEBS Letters* 427 (2): 283-5); de Meijer et al. I, II, III, and IV (I: 2003, Genetics, 163:335-346; II: 2005, *Euphytica*, 145:189-198; III: 2009, *Euphytica*, 165:293-311; and IV: 2009, *Euphytica*, 168:95-112). In some embodiments, the compositions of the present disclosure utilize the acidic tetrahydrocannabinol molecule (THCA). In some embodiments, the compositions of the present disclosure utilize the neutral (decarboxylated) tetrahydrocannabinol molecule (THC).

THC has mild to moderate analgesic effects, and can be used to treat pain by altering transmitter release on dorsal root ganglion of the spinal cord and in the periaqueductal gray. Other effects include relaxation, alteration of visual, auditory, and olfactory senses, fatigue, and appetite stimulation. THC has marked antiemetic properties, and may also reduce aggression in certain subjects (Hoaken (2003), "Drugs of abuse and the elicitation of human aggressive behavior." *Addictive Behaviors* 28: 1533-1554).

The pharmacological actions of THC result from its partial agonist activity at the cannabinoid receptors CB$_1$ and CB$_2$, G-protein coupled receptors expressed mainly by cells of the central nervous system and cells of the immune system, respectively (Pertwee, 2006, "The pharmacology of cannabinoid receptors and their ligands: An overview." *International Journal of Obesity* 30: S13-S18). The psychoactive effects of THC are primarily mediated by its activation of CB$_1$, which result in a decrease in the concentration of the second messenger molecule cAMP through inhibition of adenylate cyclase (Elphick et al., 2001, "The neurobiology and evolution of cannabinoid signaling." *Philosophical Transactions of the Royal Society B: Biological Sciences* 356 (1407): 381-408.) It is also suggested that THC has an anticholinesterase action which may implicate it as a potential treatment for Alzheimer's and Myasthenia (Eubanks et al., 2006, "A Molecular Link between the Active Component of Marijuana and Alzheimer's Disease Pathology." Molecular Pharmaceutics 3 (6): 773-7).

Both doctors and patients have been slow to adopt THC as a formal medical treatment. As a practical matter, THC's psychoactive effects at high concentrations limit patients' ability to take the drug during active periods of the day. Moreover, many patients experience negative side effects of high THC treatments, characterizing the feeling of taking such drugs as 'dysphoric and unappealing' (Russo and Guy, 2005 "A tale of two cannabinoids: The therapeutic rationale for combining tetrahydrocannabinol and cannabidiol" Med Hypotheses 66(2):234-246). III. Terpenes In some embodiments, the present disclosure provides pharmaceutical compositions comprising one or more terpenes or terpenoids. Terpenes are a large and diverse class of organic compounds produced by a variety of plants. Terpenes are derived biosynthetically from units of isoprene, which have the molecular formula C$_5$H$_8$. The basic molecular formulae of terpenes are multiples of (C$_5$H$_8$)$_n$ where n is the number of linked isoprene units. The isoprene units may be linked together "head to tail" to form linear chains or they may be arranged to form rings. Non-limiting examples of terpenes include Hemiterpenes, Monoterpenes, Sesquiterpenes, Diterpenes, Sesterterpenes, Triterpenes, Sesquarterpenes, Tetraterpenes, Polyterpenes, and Norisoprenoids.

Terpenoids, a.k.a. isoprenoids, are a large and diverse class of naturally occurring organic chemicals similar to terpenes, derived from five-carbon isoprene units assembled and modified in thousands of ways. Most are multicyclic structures that differ from one another not only in functional groups but also in their basic carbon skeletons. Well-known terpenoids include citral, menthol, camphor, salvinorin A in the plant *Salvia divinorum*, and the cannabinoids found in Cannabis. Non-limiting examples of terpenoids include, Hemiterpenoids, 1 isoprene unit (5 carbons); Monoterpenoids, 2 isoprene units (10C); Sesquiterpenoids, 3 isoprene units (15C); Diterpenoids, 4 isoprene units (20C) (e.g. ginkgolides); Sesterterpenoids, 5 isoprene units (25C); Triterpenoids, 6 isoprene units (30C) (e.g. sterols); Tetraterpenoids, 8 isoprene units (40C) (e.g. carotenoids); and Polyterpenoid with a larger number of isoprene units. Within the context and verbiage of this document the terms 'terpenoid' and 'terpene' are used interchangeably.

Terpenoids are mainly synthesized in two metabolic pathways: mevalonic acid pathway (a.k.a. HMG-CoA reductase pathway, which takes place in the cytosol) and MEP/DOXP pathway (a.k.a. The 2-C-methyl-D-erythritol 4-phosphate/ 1-deoxy-D-xylulose 5-phosphate pathway, non-mevalonate pathway, or mevalonic acid-independent pathway, which takes place in plastids). Geranyl pyrophosphate (GPP), which is used by cannabis plants to produce cannabinoids, is formed by condensation of dimethylallyl pyrophosphate (DMAPP) and isopentenyl pyrophosphate (IPP) via the catalysis of GPP synthase. Alternatively, DMAPP and IPP are ligated by FPP synthase to produce farnesyl pyrophosphate (FPP), which can be used to produce sesquiterpenoids. Geranyl pyrophosphate (GPP) can also be converted into monoterpenoids by limonene synthase.

Plant terpenoids are used extensively for their aromatic qualities. They play a role in traditional herbal remedies and are under investigation for antibacterial, antineoplastic, and other pharmaceutical functions. The terpene Linalool for example, has been found to have anti-convulsant properties (Elisabetsky et al., Phytomedicine, May 6(2):107-13 1999).

In addition to many circulatory and muscular effects, some terpenes interact with neurological receptors. A few terpenes produced by cannabis plants also bind weakly to Cannabinoid receptors. Terpenoids are lipophilic, and can interact with lipid membranes, ion channels, a variety of different receptors (including both G-protein coupled odorant and neurotransmitter receptors), and enzymes. Some are capable of absorption through human skin and passing the blood brain barrier.

A. Beta-Caryophyllene

Formula IX

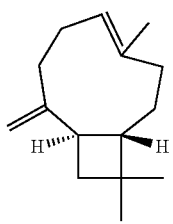

(E)-BCP

Formula X

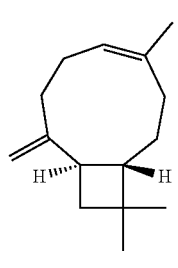

(Z)-BCP

Formula XI

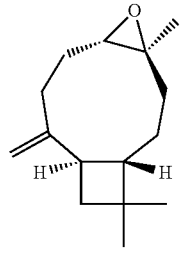

BCP oxide

Formula XII

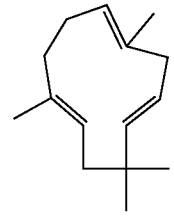

α-humulene

In some embodiments, the present disclosure provides pharmaceutical compositions comprising one or more terpenes, wherein the one or more terpenes comprise (E)-beta-caryophyllene (E-BCP). Unless otherwise stated herein, use of the term "BCP" refers to (E)-BCP.

The sesquiterpene (E)-Beta-caryophyllene ((E)-BCP, shown in Formula IX above) is a major plant volatile found in large amounts in the essential oils of many different plants, including oregano (*Origanum vulgare* L.), cinnamon (*Cinnamomum* spp.) and black pepper (*Piper nigrum* L.) (Orav et al., 2004 "Effect of storage on the essential oil composition of *Piper nigrum* L. fruits of different ripening states" J Agric Food Chem 52:2582-2586; Jayaprakasha et al., 2003 "Volatile constituents from *Cinnamomum zeylanicum* fruit stalks and their antioxidant activities" J. Agric Food Chem 51:4344-4348; Mockute et al., 2001 "The essential oil of *Origanum vulgare* L. ssp. Vulgare growing wild in Vilnius district (Lithuania)" Phytochemistry 57:65-69). (E)-BCP is often the most predominant sesquiterpenoid in *cannabis*. It is less volatile than the monoterpenoids, thus it is found in higher concentrations in material that has been processed by heat to aid in decarboxylation.

Extracts of E-BCP from plants sometimes include small quantities of (E)-BCP's isomer molecules, (Z)-Beta-caryophyllene ((Z)-BCP, shown in Formula X above) and alpha-humulene (shown in Formula XII above), or in a mixture with its oxidation product, BCP oxide (shown in Formula XI above).

Because of its taste, (E)-BCP is commercially used as a food additive and cosmetic ingredient (Skold M et al., 2006 "The fragrance chemical beta-caryophyllene-air oxidation and skin sensitization" Food Chem Toxicol 44:538-545). (E)-BCP is has been granted GRAS status (generally recognized as safe) as a flavoring by the FDA (21 CFR 172.515(b)).

(E)-BCP is also a selective full agonist at the $CB_2$ receptor, which makes it the only phytocannabinoid found outside the cannabis genus (Gertsch et al. 2008 "Beta-caryophyllene is a dietary cannabinoid" *Proc of Nat. Acad. Sci*. Vol 105(26) 9099-9104; Gertsch et al. 2008, "Anti-inflammatory cannabinoids in diet" *Communicative & Integrative Biology*, 1:1, 26-28). Recent studies have suggested BCP functionality in multiple physiological processes, including anti-inflammatory, analgesic, alcohol craving reduction, anti-cancer, anti-anxiety, and anti-depressant activities (Klauke et al. 2014 "The cannabinoid CB2 receptor-selective phytocannabinoid beta-caryophyllene exerts analgesic effects in mouse models of inflammatory and neuropathic pain" Eur Neuropsychopharmacol 24(4): 608-20; Mansouri et al., 2014 "The cannabinoid receptor 2 agonist, beta-caryophyllene, reduced voluntary alcohol intake and attenuated ethanol-induced place preference and sensitivity in mice" Pharmacol Biochem Behav. 124:260-8; Legault et al., 2007 "Potentiating effect of beta-caryophyllene on anticancer activity of alpha humulene, isocaryophyllene and paclitaxel" J Pharm Pharmacol 59(12):1643-7; Bahi et al., 2014 "Beta-caryophyllene, a CB2 receptor agonist produces multiple behavioral changes relevant to anxiety and depression in mice" Physiol Behav 135:119-24).

IV. Carydiol™ Pharmaceutical Compositions

In some embodiments, the pharmaceutical compositions described herein comprise two or more active ingredients. In some embodiments, the pharmaceutical compositions of the present invention comprise at least one cannabinoid and at least one terpene. In some embodiments, the pharmaceutical compositions of the present invention comprise at least two $CB_2$ receptor agonists. In some embodiments, the pharmaceutical compositions of the present invention comprise a $CB_2$ receptor inverse agonist and a $CB_2$ receptor agonist. In some embodiments, the pharmaceutical compositions of the present invention comprise CBD and (E)-BCP. That is, in some embodiments, the active ingredient portion of the pharmaceutical compositions described herein comprise CBD and (E)-BCP. In some embodiments, the active ingredient portion of the pharmaceutical compositions described herein consists essentially of CBD and (E)-BCP. In some embodiments, the active ingredient portion of the pharmaceutical compositions described herein consists of CBD and (E)-BCP.

In some embodiments, the pharmaceutical compositions described herein comprise three or more active ingredients. In some embodiments, the pharmaceutical compositions of the present invention comprise at least two cannabinoids and at least one terpene. In some embodiments, the pharmaceutical compositions of the present invention comprise at least two $CB_2$ receptor agonists and a $CB_1$ receptor agonist. In some embodiments, the pharmaceutical compositions of the present invention comprise a $CB_2$ receptor inverse agonist, a $CB_2$ receptor agonist, and a $CB_1$ receptor agonist. In some embodiments, the pharmaceutical compositions of the present invention comprise CBD, (E)-BCP, and THC. That is, in some embodiments, the active ingredient portion of the pharmaceutical compositions described herein comprises CBD, BCP, and THC. In some embodiments, the active ingredient portion of the pharmaceutical compositions described herein consists essentially of CBD, BCP, and THC. In some embodiments, the active ingredient portion of the pharmaceutical compositions described herein consists of CBD, BCP, and THC.

In some embodiments, the pharmaceutical compositions of the present invention (whether containing THC or not) comprises a CBD:(E)-BCP ratio of 3000:1, 769:1, 300:1, 100:1, 76.9:1, 33.3:1, 30:1, 23.1:1, 29:1, 28:1, 27:1, 26:1, 25:1, 24:1, 23:1, 22:1, 21:1, 20:1, 19:1, 18:1, 17:1, 16:1:15:1, 14:1, 13:1, 12:1, 11:1, 10:1, 9:1, 8:1, 7.69:1, 7:1, 6:1, 5:1, 4:1, 3.33:1, 3:1, 2.3:1, 2:1, 1:1, 1:1.3, 1:2, 1:3, 1:3.33, 1:4, 1:5, 1:6, 1:7, 1:8, 1:9, 1:10, 1:11, 1:12, 1:13, 1:14, 1:15, 1:16, 1:17, 1:18, 1:19, 1:20, 1:21, 1:22, 1:23, 1:24, 1:25, 1:26, 1:27, 1:28, 1:29, 1:30, 1:33.3, 1:100, 1:130, 1:300, 1:333, 1:1000, 1:1300, 1:3000 and any ranges and subranges there between.

In some embodiments, the pharmaceutical compositions of the present invention (whether containing THC or not) comprises a CBD:(E)-BCP ratio of 1:1, 1:1.3, 1:2, 1:3, 1:3.33, 1:4, 1:5, 1:6, 1:7, 1:8, 1:9, 1:10, 1:11, 1:12, 1:13, 1:14, 1:15, 1:16, 1:17, 1:18, 1:19, 1:20, 1:21, 1:22, 1:23, 1:24, 1:25, 1:26, 1:27, 1:28, 1:29, 1:30, 1:33.3, 1:100, 1:130, 1:300, 1:333, 1:1000, 1:1300, 1:3000 and any ranges and subranges there between.

In some embodiments, the pharmaceutical compositions of the present invention (whether comprising (E)-BCP or not) comprise a CBD:THC ratio of 3000:1, 769:1, 300:1, 100:1, 76.9:1, 33.3:1, 30:1, 23.1:1, 29:1, 28:1, 27:1, 26:1, 25:1, 24:1, 23:1, 22:1, 21:1, 20:1, 19:1, 18:1, 17:1, 16:1:15:1, 14:1, 13:1, 12:1, 11:1, 10:1, 9:1, 8:1, 7.69:1, 7:1, 6:1, 5:1, 4:1, 3.33:1, 3:1, 2.3:1, 2:1, 1:1, 1:1.3, 1:2, 1:3, 1:3.33, 1:4, 1:5, 1:6, 1:7, 1:8, 1:9, 1:10, 1:11, 1:12, 1:13, 1:14, 1:15, 1:16, 1:17, 1:18, 1:19, 1:20, 1:21, 1:22, 1:23, 1:24, 1:25, 1:26, 1:27, 1:28, 1:29, 1:30, 1:33.3, 1:100, 1:130, 1:300, 1:333, 1:1000, 1:1300, 1:3000, and any ranges and subranges there between.

In some embodiments, the pharmaceutical compositions of the present invention (whether comprising (E)-BCP or not) comprise a CBD:THC ratio of 1:1, 1:1.3, 1:2, 1:3, 1:3.33, 1:4, 1:5, 1:6, 1:7, 1:8, 1:9, 1:10, 1:11, 1:12, 1:13, 1:14, 1:15, 1:16, 1:17, 1:18, 1:19, 1:20, 1:21, 1:22, 1:23, 1:24, 1:25, 1:26, 1:27, 1:28, 1:29, 1:30, 1:33.3, 1:100, 1:130, 1:300, 1:333, 1:1000, 1:1300, 1:3000, and any ranges and subranges there between.

In some embodiments, the pharmaceutical compositions the present invention comprise a THC:(E)-BCP ratio of 1:1, 10:13, 1:2, 1:3, 3:10, 1:4, 1:5, 1:6, 1:7, 1:8, 1:9, 1:10, 1:11, 1:12, 1:13, 1:14, 1:15, 1:16, 1:17, 1:18, 1:19, 1:20, 1:21, 1:22, 1:23, 1:24, 1:25, 1:26, 1:27, 1:28, 1:29, 1:30, 3:100, 1:100, 1:130, 1:300, 3:1000, 1:1000, 1:1300, 1:3000, and any ranges and subranges there between.

Herein, reference to a ratio of two or more compounds encompasses both molar ratios and mass ratios.

That is, in some embodiments, the formulations of the present disclosure comprise a THC:CBD:(E)-BCP ratio of [1-30]:[1-3000]:[1-3000], wherein [1-30] or [1-3000] indicates a possible range of ratio values from 1-30 (or 1-3000) for each component. For example, in some embodiments, the pharmaceutical formulations of the present disclosure comprise a 1:30:4 ratio of THC:CBD:(E)-BCP.

Thus, in some embodiments, the active ingredient portion of the disclosed pharmaceutical comprises 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, or 50% THC, and any ranges and subranges there between. In some embodiments, the active ingredient portion of the disclosed pharmaceutical comprise low amounts of THC. In some embodiments, a "low amount of THC" refers to an amount of THC in a composition that is less than 10%. For example, in some embodiments, the active ingredient portion of the disclosed pharmaceutical comprises less than 10%, less than 9%, less than 8%, less than 7%, less than 6%, less than 5%, less than 4%, less than 3%, less than 2%, or less than 1% THC. In some embodiments, the active ingredient portion of the disclosed pharmaceutical comprise low amounts of THC, such as about 1%, 2%, 3%, 4%, 5%, 6%, 7%, 8%, 9%, or 10% THC.

Thus, in some embodiments, the active ingredient portion of the disclosed pharmaceutical comprises 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% CBD, and any ranges and subranges there between.

In some embodiments, the active ingredient portion of the disclosed pharmaceutical comprises 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% (E)-BCP, and any ranges and subranges there between.

Thus, in some embodiments, the active ingredient portion of the disclosed pharmaceutical comprises any one of the following combinations of CBD and (E)-BCP concentrations, including any ranges, and subranges there between: 5% CBD and 95% (E)-BCP, 10% CBD and 90% (E)-BCP, 15% CBD and 85% (E)-BCP, 20% CBD and 80% (E)-BCP, 25% CBD and 75% (E)-BCP, 30% CBD and 70% (E)-BCP, 35% CBD and 65% (E)-BCP, 40% CBD and 60% (E)-BCP, 45% CBD and 55% (E)-BCP, 50% CBD and 50% (E)-BCP, 55% CBD and 45% (E)-BCP, 60% CBD and 40% (E)-BCP, 65% CBD and 35% (E)-BCP, 70% CBD and 30% (E)-BCP, 75% CBD and 25% (E)-BCP, 80% CBD and 20% (E)-BCP, 85% CBD and 15% (E)-BCP, 90% CBD and 10% (E)-BCP, or 95% CBD and 5% (E)-BCP.

Thus, in some embodiments, the active ingredient portion of the disclosed pharmaceutical comprises any one of the following combinations of CBD and (E)-BCP concentrations, including any ranges, and subranges there between: 50% CBD and 50% (E)-BCP, 55% CBD and 45% (E)-BCP, 60% CBD and 40% (E)-BCP, 65% CBD and 35% (E)-BCP, 70% CBD and 30% (E)-BCP, 75% CBD and 25% (E)-BCP, 80% CBD and 20% (E)-BCP, 85% CBD and 15% (E)-BCP, 90% CBD and 10% (E)-BCP, or 95% CBD and 5% (E)-BCP.

In some embodiments, the active ingredient portion of the present disclosure consists of CBD and BCP. Thus in some embodiments, the active ingredient portion consists of X % CBD and Y % (E)-BCP, wherein X and Y can each be 0-100%, so long as X+Y=100%.

In some embodiments, the active ingredient portion of the present disclosure consists of CBD, BCP, and THC. Thus in some embodiments, the active ingredient portion consists of X % THC, Y % CBD, and Z % (E)-BCP, wherein X, Y, and Z can each be 0-100%, so long as X+Y+Z=100%. For example, in some embodiments, the active ingredient portion of the present disclosure consists of 2.86% THC, 85.72% CBD, and 11.42% (E)-BCP.

Thus, in some embodiments, the active ingredient portion of the disclosed pharmaceutical comprises 1 mg, 2 mg, 3 mg, 4 mg, 5 mg, 6 mg, 7 mg, 8 mg, 9 mg, 10 mg, 11 mg, 12 mg, 13 mg, 14 mg, 15 mg, 16 mg, 17 mg, 18 mg, 19 mg, 20 mg, 21 mg, 22 mg, 23 mg, 24 mg, 25 mg, 26 mg, 27 mg, 28 mg, 29 mg, 30 mg, 31 mg, 32 mg, 33 mg, 34 mg, 35 mg, 36 mg, 37 mg, 38 mg, 39 mg, 40 mg, 41 mg, 42 mg, 43 mg, 44 mg, 45 mg, 46 mg, 47 mg, 48 mg, 49 mg, 50 mg, 51 mg, 52 mg, 53 mg, 54 mg, 55 mg, 56 mg, 57 mg, 58 mg, 59 mg, 60 mg, 61 mg, 62 mg, 63 mg, 64 mg, 65 mg, 66 mg, 67 mg, 68 mg, 69 mg, 70 mg, 71 mg, 72 mg, 73 mg, 74 mg, 75 mg, 76 mg, 77 mg, 78 mg, 79 mg, 80 mg, 81 mg, 82 mg, 83 mg, 84 mg, 85 mg, 86 mg, 87 mg, 88 mg, 89 mg, 90 mg, 91 mg, 92 mg, 93 mg, 94 mg, 95 mg, 96 mg, 97 mg, 98 mg, or 99 mg THC, and any ranges and subranges there between. In some embodiments, the active ingredient portion of the disclosed pharmaceutical comprise low amounts of THC, such as 1 mg, 2 mg, 3 mg, 4 mg, 5 mg, 6 mg, 7 mg, 8 mg, 9 mg, or 10 mg THC.

In some embodiments, the active ingredient portion of the disclosed pharmaceutical comprises 1 mg, 2 mg, 3 mg, 4 mg, 5 mg, 6 mg, 7 mg, 8 mg, 9 mg, 10 mg, 11 mg, 12 mg, 13 mg, 14 mg, 15 mg, 16 mg, 17 mg, 18 mg, 19 mg, 20 mg, 21 mg, 22 mg, 23 mg, 24 mg, 25 mg, 26 mg, 27 mg, 28 mg, 29 mg, 30 mg, 31 mg, 32 mg, 33 mg, 34 mg, 35 mg, 36 mg, 37 mg, 38 mg, 39 mg, 40 mg, 41 mg, 42 mg, 43 mg, 44 mg, 45 mg, 46 mg, 47 mg, 48 mg, 49 mg, 50 mg, 51 mg, 52 mg, 53 mg, 54 mg, 55 mg, 56 mg, 57 mg, 58 mg, 59 mg, 60 mg, 61 mg, 62 mg, 63 mg, 64 mg, 65 mg, 66 mg, 67 mg, 68 mg, 69 mg, 70 mg, 71 mg, 72 mg, 73 mg, 74 mg, 75 mg, 76 mg, 77 mg, 78 mg, 79 mg, 80 mg, 81 mg, 82 mg, 83 mg, 84 mg, 85 mg, 86 mg, 87 mg, 88 mg, 89 mg, 90 mg, 91 mg, 92 mg, 93 mg, 94 mg, 95 mg, 96 mg, 97 mg, 98 mg, 99 mg, 100 mg, 105 mg, 110 mg, 115 mg, 120 mg, 125 mg, 130 mg, 135 mg, 140 mg, 145 mg, 150 mg, 155 mg, 160 mg, 165 mg, 170 mg, 175 mg, 180 mg, 185 mg, 190 mg, 195 mg, 200 mg, 205 mg, 210 mg, 215 mg, 220 mg, 225 mg, 230 mg, 235 mg, 240 mg, 245 mg, 250 mg, 255 mg, 260 mg, 265 mg, 270 mg, 275 mg, 280 mg, 285 mg, 290 mg, 295 mg, 300 mg, 305 mg, 310 mg, 315 mg, 320 mg, 325 mg, 330 mg, 335 mg, 340 mg, 345 mg, 350 mg, 355 mg, 360 mg, 365 mg, 370 mg, 375 mg, 380 mg, 385 mg, 390 mg, 395 mg, 400 mg, 405 mg, 410 mg, 415 mg, 420 mg, 425 mg, 430 mg, 435 mg, 440 mg, 445 mg, 450 mg, 455 mg, 460 mg, 465 mg, 470 mg, 475 mg, 480 mg, 485 mg, 490 mg, 495 mg, 500 mg, 505 mg, 510 mg, 515 mg, 520 mg, 525 mg, 530 mg, 535 mg, 540 mg, 545 mg, 550 mg, 555 mg, 560 mg, 565 mg, 570 mg, 575 mg, 580 mg, 585 mg, 590 mg, 595 mg, 600 mg, 605 mg, 610 mg, 615 mg, 620 mg, 625 mg, 630 mg, 635 mg, 640 mg, 645 mg, 650 mg of CBD or more, and any ranges and subranges there between.

In some embodiments, the active ingredient portion of the disclosed pharmaceutical comprises 1 mg, 2 mg, 3 mg, 4 mg, 5 mg, 6 mg, 7 mg, 8 mg, 9 mg, 10 mg, 11 mg, 12 mg, 13 mg, 14 mg, 15 mg, 16 mg, 17 mg, 18 mg, 19 mg, 20 mg, 21 mg, 22 mg, 23 mg, 24 mg, 25 mg, 26 mg, 27 mg, 28 mg, 29 mg, 30 mg, 31 mg, 32 mg, 33 mg, 34 mg, 35 mg, 36 mg, 37 mg, 38 mg, 39 mg, 40 mg, 41 mg, 42 mg, 43 mg, 44 mg, 45 mg, 46 mg, 47 mg, 48 mg, 49 mg, 50 mg, 51 mg, 52 mg, 53 mg, 54 mg, 55 mg, 56 mg, 57 mg, 58 mg, 59 mg, 60 mg, 61 mg, 62 mg, 63 mg, 64 mg, 65 mg, 66 mg, 67 mg, 68 mg, 69 mg, 70 mg, 71 mg, 72 mg, 73 mg, 74 mg, 75 mg, 76 mg, 77 mg, 78 mg, 79 mg, 80 mg, 81 mg, 82 mg, 83 mg, 84 mg, 85 mg, 86 mg, 87 mg, 88 mg, 89 mg, 90 mg, 91 mg, 92 mg, 93 mg, 94 mg, 95 mg, 96 mg, 97 mg, 98 mg, or 99 mg (E)-BCP, and any ranges and subranges there between.

Persons having skill in the art will recognize that the presently disclosed compositions will, in some embodiments, also apply to modified CBD molecules. In some embodiments, the present disclosure's compositions comprise modified CBD molecules in place of the recited CBD content. Thus in some embodiments, the presently disclosed compositions use fluorinated CBD instead of CBD. For example, in some embodiments, the compositions described herein comprise HUF101, HUF103, and/or HUF559a. Additional examples of fluorinated CBD (F-CBD) can be found in U.S. Pat. No. 9,447,019, and published PCT Application No. WO 2017/008136, each of which are hereby incorporated by reference in their entireties.

In some embodiments, the compositions of the present disclosure use THCA instead of THC. Thus, in some embodiments, the compositions ranges, concentrations, ranges, and ingredient lists of the present disclosure which utilize THC, also apply to THCA.

In some embodiments, one or more of the active ingredients of the present disclosure are substantially pure ingredients. In other embodiments, the present disclosure provides whole plant, or botanical drug substance extractions, in which extracted active ingredients may comprise one or more non-active constituents. In some embodiments, the botanical drug substance extractions produce one or more enriched active ingredient(s). The non-active constituents present in enriched active ingredients are not considered part of the active ingredient portion of the formulation, and are therefore not included in the active ingredient portion formulations of the present disclosure.

In some embodiments, all active ingredients are bred into a single cannabis plant. Thus in some embodiments, the pharmaceutical of the present disclosure comprises flower tissue from one or more cannabis strains.

In some embodiments, the pharmaceutical compositions of the present disclosure can be administered orally, via implant, parenterally, sublingually, rectally, topically, via inhalation, etc.

In some embodiments, the present disclosure provides formulations of the compositions described herein comprising a coconut oil base in kosher vegetable capsules. In some embodiments, the present disclosure provides a 1:30:4 formulation of THC, CBD, and (E)-BCP, in an oil solvent base.

In some embodiments, the active ingredients are lipophilic, and exhibit low water solubility. In some embodiments, the active ingredients of the present disclosure are made water soluble via pre-treatments, such as those described in U.S. Published Patent Application Nos. 2016/0243177, 2016/0143972, and 2016/0324776.

In some embodiments, the present disclosure provides liquid formulations of the presently disclosed pharmaceutical compositions. In some embodiments, the liquid formulations are suitable for oral administration and include, but are not limited to, pharmaceutically acceptable emulsions, solutions, suspensions, syrups and elixirs. In addition to the active ingredients, the liquid formulations can contain in some embodiments inert diluents commonly used in the art. For instance, in some embodiments, liquid formulations can contain water, alcohol, oils, polyethylene glycol ethers, or any other pharmaceutically acceptable solvents. In some embodiments, the compositions of the present disclosure include solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor, sesame oil, or other vegetable oils), glycerol, tetrahydrofurfuryl alcohol, polyethylene glycols and fatty acid esters of sorbitan, and mixtures thereof.

In some embodiments, liquid formulations are suitable for oral administration and can include adjuvants such as wetting agents, emulsifying and suspending agents, sweetening, flavoring, and perfuming agents. When formulated as a suspension, the inventive compositions contain the active ingredients and suspending agents, for example, ethoxylated isostearyl alcohols, polyoxyethylene sorbitol, sorbitan esters, microcrystalline cellulose, aluminum metahydroxide, bentonite, agar-agar, tragacanth, and mixtures thereof.

In some embodiments, the liquid formulations of the compositions of the present disclosure are spray formulations suitable for buccal delivery. In some embodiments, the spray formulation comprises components designed to accelerate absorption through the mucosa, such as those described in U.S. Pat. Nos. 7,622,140; 9,029,423; 8,211,946; 7,025,992; and 6,946,150, each of which is hereby incorporated by reference in its entirety for all purposes.

In other embodiments, the present disclosure provides transdermal formulations of the presently disclosed pharmaceutical compositions. In such embodiments, the transdermal formulations a suitable for absorption through the skin. In some embodiments, the transdermal formulation comprises components designed to accelerate absorption through the skin of the patient, such as those described in US. Patent Application No. 2015/0126595.

In other embodiments, the present disclosure provides solid formulations of the pharmaceuticals compositions described herein. Methods of solidifying the active ingredients are known in the art. In some embodiments, the present disclosure provides use of THC and/or CBD and/or BCP solid formulations as described in U.S. Published Patent Application Nos. 2016/0243177 and 2016/0143972. In other embodiments, the present disclosure teaches the use of solid THC, CBD and/or BCP crystals, such as commercially available THC or CBD solid substantially pure ingredient.

In some embodiments, solid formulations are suitable for oral administration and include for example, capsules, dragees, tablets, pills, powders, and granules. In such solid formulations, the active ingredients are, in some embodiments, mixed with at least one pharmaceutically acceptable excipient or carrier such as sodium citrate or dicalcium phosphate and/or a) fillers or extenders such as starches, lactose, sucrose, glucose, mannitol, and silicic acid; b) binders such as, for example, carboxymethylcellulose, alginates, gelatin, polyvinylpyrrolidone, sucrose, and acacia; c) humectants such as glycerol; d) disintegrating agents such as agar-agar, calcium carbonate, potato or tapioca starch, alginic acid, certain silicates, and sodium carbonate; e) solution retarding agents such as paraffin; f) absorption accelerators such as quaternary ammonium compounds; g) wetting agents such as, for example, acetyl alcohol and glycerol monostearate; h) absorbents such as kaolin and bentonite clay; and i) lubricants such as talc, calcium stearate, magnesium stearate, solid polyethylene glycols, sodium lauryl sulfate, and mixtures thereof. For capsules, tablets and pills, the solid formulations can also comprise buffering agents.

In other embodiments, the present disclosure provides methods of solubilizing the active ingredient portion by creating a micellular or liposomal suspension. In some embodiments, micellular or liposomal suspensions can be encapsulated with a variety of polymers, sugars, and chelating agents to yield stable solid liposomal active ingredient preparations. Encapsulation can take the form of cross-linked polymers, trapping of the micelles or liposomes within a non-crosslinked polymer network, or dispersed within the crystalline structure of sugar starches or protein molecules. These granules can be further processed to yield sublingual films, suppositories, dispersible powder, tablets, gel capsules, etc. In some embodiments, the present disclosure provides formulations created according to U.S. Pat. No. 9,095,555.

In some embodiments, the present disclosure provides that solid formulations in the form of tablets, dragees, capsules, pills, and granules can be coated using compounds that accelerate or decrease the release of the presently disclosed formulation. For instance, the invention encompasses solid formulations having enteric coatings, extended-release coatings, sustained-release coatings, delayed release coatings and immediate-release coatings. Methods used to coat solid dosage forms as well as the materials used to manufacture such coatings are well-known in the pharmaceutical formulary art. The solid formulations can optionally contain opacity enhancing agents. According to an embodiment, the solid dosage form comprises an enteric coating that permits the release of the active ingredients at a specific location within the gastrointestinal tract, optionally, in a delayed manner. Exemplary of such coating materials include glyceryl monostearate or glyceryl distearate may be employed, polymeric substances and waxes. In some embodiments, the presently disclosed formulation can also be in micro-encapsulated form, if appropriate, with one or more of the above-mentioned excipients.

In some embodiments, the solid formulations of the present invention may optionally be coated with one or more materials suitable for the regulation of release or for the protection of the formulation. In one embodiment, coatings are provided to permit either pH-dependent or pH-independent release, e.g., when exposed to gastrointestinal fluid. In some embodiments, a pH-dependent coating serves to release the disclosed pharmaceutical composition in desired areas of the gastro-intestinal (GI) tract, e.g., the stomach or small intestine. In some embodiments, the present disclosure provides a pH-independent coating designed to achieve optimal release regardless of pH-changes in the environmental fluid, e.g., the GI tract. In some embodiments, the present disclosure provides formulations which release a portion of the dose in one desired area of the GI tract, e.g., the stomach, and release the remainder of the dose in another area of the GI tract, e.g., the small intestine.

Formulations according to the invention that utilize pH-dependent coatings to obtain formulations may also impart a repeat-action effect whereby unprotected drug is coated over the enteric coat and is released in the stomach, while the remainder, being protected by the enteric coating, is released further down the gastrointestinal tract. Coatings which are pH-dependent may be used in accordance with the present invention include shellac, cellulose acetate phthalate (CAP), polyvinyl acetate phthalate (PVAP), hydroxypropylmethyl-cellulose phthalate, and methacrylic acid ester copolymers, zein, and the like.

A dietary composition according to the present invention is any ingestible preparation that contains the active ingredient portion comprising the active ingredients of the invention mixed with a food product. In some embodiments, the food product can be dried, cooked, boiled, lyophilized or baked. Breads, teas, soups, cereals, salads, sandwiches, sprouts, vegetables, animal feed, pills and tablets, are among the vast number of different food products contemplated in the present invention.

In some embodiments, the present disclosure provides parenteral injection formulations of the presently disclosed pharmaceutical composition. In some embodiments, the parenteral injections of the present disclosure comprise pharmaceutically acceptable sterile aqueous or nonaqueous solutions, dispersions, suspensions or emulsions as well as sterile powders for reconstitution into sterile injectable solutions or dispersions prior to use. Examples of suitable aqueous and nonaqueous carriers, diluents, solvents or vehicles for selected embodiments of the present disclosure include water, ethanol, polyols (such as glycerol, propylene glycol, polyethylene glycol, and the like), carboxymethyl-cellulose and suitable mixtures thereof, vegetable oils (such as olive oil), and injectable organic esters such as ethyl oleate. Proper fluidity can be maintained, for example, by the use of coating materials such as lecithin, by the maintenance of the required particle size in the case of dispersions, and by the use of surfactants. The compositions of the present invention can also contain adjuvants such as, but not limited to, preservatives, wetting agents, emulsifying agents, and dispersing agents. Compositions for parenteral delivery generally include isotonic agents such as sugars, sodium chloride, and the like. Prolonged absorption of the injectable pharmaceutical formulation can be brought about by the inclusion of agents that delay absorption such as aluminum monostearate and gelatin.

V. Carydiol™ Methods of Use

In some embodiments, the present disclosure provides methods of treating a disease or condition in a subject in need thereof comprising administering a pharmaceutical composition described herein (e.g. a Carydiol™ composition) to the subject in order to treat said disease or condition. In some embodiments, the present disclosure provides methods for exposing the pharmaceutical compositions to a sample comprising one or more cells A. Carydiol™ Dosing and Administration In some embodiments, the pharmaceutical compositions disclosed herein (e.g., Carydiol™ compositions) are exposed to a sample or administered to a subject. Administration of the pharmaceutical compositions to a subject can occur by injection, irrigation, inhalation, consumption, electro-osmosis, hemodialysis, iontophoresis, and other methods known in the art. In some embodiments, administration route is local or systemic. In some embodiments administration route is intraarterial, intracranial, intradermal, intraduodenal, intrammamary, intrameningeal, intraperitoneal, intrathecal, intratumoral, intravenous, intravitreal, ophthalmic, parenteral, spinal, subcutaneous, ureteral, urethral, vaginal, intrauterine, or intraperitoneal. In some embodiments, the administration route is by infusion (e.g., continuous or bolus). In some embodiments, the administration route is by topical administration or direct injection. For administration to subject, the pharmaceutical compositions disclosed herein (e.g., Carydiol™ compositions) are administered and dosed in accordance with good medical practice, taking into account the clinical condition of the individual patient, the disease or condition to be treated, the site and method of administration, scheduling of administration, patient age, sex, body weight, and other factors known to medical practitioners.

Typically, a therapeutically effective amount of a pharmaceutical composition is administered. The effective amount of a particular pharmaceutical composition may be represented in a variety of ways based on the nature of the pharmaceutical composition, such as mass/volume or (mass of the composition)/(mass of a subject). The effective amount of a particular composition may also be expressed as the half-maximal effective concentration ($EC_{50}$), which refers to the concentration of the composition that results in a magnitude of a particular physiological response that is half-way between a reference level and a maximum response level. The therapeutically effective dose can be determined by a person having ordinary skill in the art upon perusal of the disclosure according to known considerations and appropriate measurements. For example, in some embodiments, the therapeutically effective dose is the dose or amount effective reduce one or more symptoms or characteristics of inflammatory responses including reduced expression of one or more pro-inflammatory genes, reduced production of one or more pro-inflammatory mediators, reduction in one or more symptoms of pain (e.g. to increase nociceptive thresholds of a subject compared to an untreated subject), reduced swelling, and/or reduced fever.

In some embodiments, the therapeutically effective dose of the active ingredient portion of the presently disclosed pharmaceutical composition ranges from about 0.5 mg/kg to about 50 mg/kg, such as, for example, from about or from about 0.5 mg/kg to about 40 mg/kg, 0.5 mg/kg to about 30 mg/kg, 0.5 mg/kg to about 20 mg/kg, 0.5 mg/kg to about 10 mg/kg, from about 0.5 mg/kg to about 6 mg/kg, from about 0.5 mg/kg to about 4 mg/kg, from about 0.5 mg/kg to about 2 mg/kg, from about 0.5 mg/kg to about 1.8 mg/kg, from about 0.5 mg/kg to about 1.6 mg/kg, from about 0.5 mg/kg to about 1.4 mg/kg, from about 0.5 mg/kg to about 1.2 mg/kg, from about 0.5 mg/kg to about 1 mg/kg, from about 0.5 mg/kg to about 0.8 mg/kg, or from about 0.5 mg/kg to about 0.6 mg/kg. Each possibility is a separate embodiment of the invention.

Thus, in some embodiments, the present disclosure provides active ingredient portion doses of 1 mg/kg, 2 mg/kg, 3 mg/kg, 4 mg/kg, 5 mg/kg, 6 mg/kg, 7 mg/kg, 8 mg/kg, 9 mg/kg, 10 mg/kg, 11 mg/kg, 12 mg/kg, 13 mg/kg, 14 mg/kg, 15 mg/kg, 16 mg/kg, 17 mg/kg, 18 mg/kg, 19 mg/kg, 20 mg/kg, 21 mg/kg, 22 mg/kg, 23 mg/kg, 24 mg/kg, 25 mg/kg, 26 mg/kg, 27 mg/kg, 28 mg/kg, 29 mg/kg, 30 mg/kg, 31 mg/kg, 32 mg/kg, 33 mg/kg, 34 mg/kg, 35 mg/kg, 36 mg/kg, 37 mg/kg, 38 mg/kg, 39 mg/kg, 40 mg/kg, 41 mg/kg, 42 mg/kg, 43 mg/kg, 44 mg/kg, 45 mg/kg, 46 mg/kg, 47 mg/kg, 48 mg/kg, 49 mg/kg, 50 mg/kg, and any ranges and subranges there between.

In some embodiments, the average daily dose of the active ingredient portion of the present disclosure for a human subject (such as a human child, weighing between about 10 kg and about 40 kg or a human adult, weighing between about 40 kg and about 120 kg) can be about 5 mg, about 10 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, about 100 mg, about 200 mg, about 300 mg, about 400 mg, about 500 mg about 600 mg, about 700 mg, about 800 mg, about 900 mg, about 1000 mg, about 1100 mg, about 1200 mg, about 1300 mg, or about 1400 mg. Each possibility is a different embodiment of the invention.

In some embodiments, the present disclosure discloses that the pharmaceutical compositions of the present disclosure exhibit greater pharmaceutical efficacy than an equally dosed administration of any of the THC, CBD, or (E)-BCP active ingredients alone, as dosed in the full pharmaceutical composition. That is, in some embodiments, the active ingredient portion of the present disclosure exploits the additive pharmaceutical effects of each of its THC, CBD and (E)-BCP components. In some embodiments, the present disclosure discloses that the active ingredient portion of the present disclosure provides at least one additional benefit to patients over the individual dosing of either THC, CBD or (E)-BCP (e.g., improved absorbance, flavor, reduced side effects, increased patient compliance, etc.). For example, in some embodiments, the pharmaceutical compositions of the present disclosure is essentially free from the paranoia, dystonic side effects of the THC portion of the dose, had it been administered alone.

In other embodiments, the pharmaceutical compositions of the present disclosure exhibits synergistic improvements in pharmaceutical efficiency over the measured efficacies of individual THC, CBD or (E)-BCP treatments.

In some embodiments, the present disclosure provides methods of treating a subject with CBD and (E)-BCP, said treatment comprising the step of administering said active ingredients to a subject in need thereof. In other embodiments, the present disclosure provides methods of treating a subject with THC, CBD, and (E)-BCP, said treatment comprising the step of administering said active ingredients to a subject or patient in need thereof.

In some embodiments, the treatments of the present disclosure comprise pre-mixed pharmaceutical compositions comprising the active ingredients. Thus, in some embodiments, the administering step of the present disclosure comprises the administering of a single mixture or formulation according to the present disclosure.

In other embodiments, the administering step comprises the co-administration of each individual unmixed active ingredient, either in its natural form, or in an individual formulation according to present disclosure. Thus in some embodiments, the administering step comprises providing a subject with three separate doses for each of the active ingredients, either in their natural form, or in individual formulations according to the present disclosure.

In some embodiments, all active ingredients are administered at the same time. In other embodiments, the active ingredients are administered sequentially. In some embodiments, the present disclosure discloses that each active ingredient may be administered any time within a 24 hour period. Thus in some embodiments one or more active ingredient is administered 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 90, 120, 150, 180, 210, 240, 270, 300, 330, 360, 390, or 420 minutes apart from the administration of the previous active ingredient. In other embodiments, one or more active ingredient(s) are administered 1, 2, 3, 4, 5, 6, 7, 8, 9, 10, 11, 12, 13, 14, 15, 16, 17, 18, 19, 20, 21, 22, or 23 hours apart from the administration of the previous active ingredient.

In some embodiments of the present disclosure, all of the active ingredients are administered within a 24 hour period. In some embodiments of the present disclosure, all of the active ingredients are administered within a 16 hour period. In some embodiments of the present disclosure, all of the active ingredients are administered within a 12 hour period. In some embodiments of the present disclosure, all of the active ingredients are administered within an 8 hour period. In some embodiments of the present disclosure, all of the active ingredients are administered within a 4 hour period. In some embodiments of the present disclosure, all of the active ingredients are administered within a 2 hour period. In some embodiments of the present disclosure, all of the active ingredients are administered within 1 hour.

In some embodiments, the present disclosure teaches that the active ingredients may be administered in any desired order. In other embodiments, the present disclosure teaches ordered administration. Thus in some embodiments, the present disclosure teaches administration of the ingredients in the order of THC-CBD-(E)-BCP, THC-(E)-BCP-CBD, CBD-THC-(E)-BCP, CBD-(E)-BCP-THC, (E)-BCP-THC-CBD, or (E)-BCP-CBD-THC.

In some embodiments, the present disclosure teaches a single daily dose (e.g. a single dose of the pharmaceutical composition). In other embodiments, the present disclosure teaches 2, 3, 4, 5, 6, 7, 8, 10, 11, 12, 13, 14, 15, 16, 17, 18, 19, 20, 21, 22, 23, or 24 doses per day. In some embodiments, the present disclosure teaches 3 doses per day.

B. Carydiol™ Methods of Treatment

In some embodiments, the present disclosure provides methods of treating a disease or condition in a subject in need thereof comprising administering a pharmaceutical composition described herein (e.g. a Carydiol™ composition) to the subject in order to treat said disease or condition. In some embodiments, treating refers to (a) amelioration of various physiological symptoms associated with the disease or condition (e.g., a reduction in the severity, frequency, and/or persistence of one or more symptoms of the disease or condition); (b) arresting development or preventing progression of the disease or condition; (c) regression in the state of the disease or condition; (d) curing the disease or condition; (e) increased life expectancy; and/or (f) increased progression-free or disease-free survival.

Diseases or conditions suitable for treatment with the pharmaceutical compositions described herein include, but are not limited to, inflammatory diseases, neurological diseases, pain, substance addiction, and inflammatory skin conditions. Measurements for assessing the treatment of a disease or condition will vary with the nature of the disease or condition and suitable measurements for a particular disease or condition can be determined by one of skill in the art. Suitable measurements and assays may include gene expression analyses (e.g., qPCR, DNA sequencing, RNA sequencing), soluble and cellular protein expression analyses (e.g., Western blot, ELISA, ELISpot, flow cytometry, histology), cell counts, physical measurements to assess swelling, fever, pain tolerance, or other symptom of a particular disease or condition.

1. Carydiol™ for the treatment of inflammatory conditions

In some embodiments, the present disclosure provides a method of reducing inflammation in a subject in need thereof, comprising administering to the subject a composition containing one or more active ingredients, said active ingredients comprising a therapeutically effective amount of CBD and (E)-BCP. In some embodiments, the present disclosure provides a method of reducing inflammation in a subject in need thereof, comprising administering to the subject a composition containing one or more active ingredients, said active ingredients consisting essentially of a therapeutically effective amount of CBD and (E)-BCP. In some embodiments, the present disclosure provides a method of reducing inflammation in a subject in need thereof, comprising administering to the subject a composition containing one or more active ingredients, said active ingredients consisting of a therapeutically effective amount of CBD and (E)-BCP.

In some embodiments, the present disclosure provides a method of reducing inflammation in a subject in need thereof, comprising administering to the subject a composition containing one or more active ingredients, said active ingredients comprising a therapeutically effective amount of CBD, (E)-BCP, and THC. In some embodiments, the present disclosure provides a method of reducing inflammation in a subject in need thereof, comprising administering to the subject a composition containing one or more active ingredients, said active ingredients consisting essentially of a therapeutically effective amount of CBD, (E)-BCP, and THC. In some embodiments, the present disclosure provides a method of reducing inflammation in a subject in need thereof, comprising administering to the subject a composition containing one or more active ingredients, said active ingredients consisting of a therapeutically effective amount of CBD, (E)-BCP, and THC.

In some embodiments, the efficacy of a composition described herein in the treatment of an inflammatory disease can be determined by measurement of one or more physical symptoms of inflammation and/or one or more cellular or molecular inflammatory responses. Physical symptoms of inflammation include, but are not limited to, heat (i.e., fever), redness, pain, swelling, and loss of function. Cellular or molecular inflammatory responses include, but are not limited to, cellular proliferation and differentiation, production of inflammatory mediators (e.g., antibodies, cytokines, chemokines, etc.), cell death, and tissue remodeling. Inflammation can be acute, with onset minutes to hours after exposure to the injurious stimuli and lasting a few days, or chronic, with delayed onset after exposure to the injurious stimuli and lasting for months or years.

In some embodiments, the inflammatory response is characterized by molecular and cellular responses including increased expression of one or more inflammatory genes (e.g., inflammatory cytokines or other inflammatory mediators), increased production of inflammatory mediators (e.g. inflammatory cytokines), increased proliferation of white blood cells, increased localization of white blood cells to an affected area, increased activation of one or more types of white blood cells, and the like, as compared to a subject that does not suffer from the disease or condition, or has not been exposed to the microbe or microbial component. In some embodiments, the inflammatory response is characterized by physical symptoms such as edema (e.g., swelling), fever, decreased nociceptive thresholds (e.g. increased sensitivity or pressure or heat applied to an affected area of the subject), increased pain, and the like, as compared to a subject that does not suffer from the disease or condition, or has not been exposed to the microbe or microbial component. In some embodiments, the inflammatory response in the subject may be a chronic inflammatory response or an acute inflammatory response. In some embodiments, the inflammatory response in the subject is a result of exposure to a microbe (e.g., a bacteria, a virus, or a fungus) or a microbial component. In some embodiments, the inflammatory response in the subject is a result of a disease or condition from which the subject suffers, or from which the subject is predicted to suffer.

In some embodiments, the compositions described herein exert anti-inflammatory effects when administered to a subject. In some embodiments, the anti-inflammatory properties of a composition described herein can be determined by measuring the ability of the pharmaceutical composition to reduce or inhibit one or more signs or symptoms of an inflammatory response. Anti-inflammatory properties or effects of a composition can be measured and observed by a variety of means known in the art including, but not limited to, changes in the expression of pro- and anti-inflammatory genes (e.g., cytokine genes and chemokine genes) and changes in production of pro- and anti-inflammatory mediators (e.g., cytokine and chemokine). For example, in some embodiments, administration of a pharmaceutical composition described herein to a subject results in the decreased expression of one or more pro-inflammatory genes. Inflammatory genes may include cytokine genes including, but not limited to, IL-1α, IL-1β, TNFα, IFNα, IFNβ, IFNγ, IL-6, IL-8, IL-12. In some embodiments, administration of a pharmaceutical composition described herein to a subject results in the increased expression of one or more anti-inflammatory genes. Anti-inflammatory genes may include anti-inflammatory cytokines including, but not limited to, TGFβ and IL-10. In some embodiments, administration of a pharmaceutical composition described herein to a subject results in the decreased production of one or more inflammatory mediators, including inflammatory cytokines (e.g., IL-1α, IL-1β, TNFα, IFNα, IFNβ, IFNγ, IL-6, IL-8, and IL-12), reactive oxygen species, and cytolytic factors (e.g., perforin and granzymes). In some embodiments, administration of a pharmaceutical composition described herein to a subject results in the increased production of one or more anti-inflammatory mediators, including, but not limited to, anti-inflammatory cytokines (e.g., IL-10 and TGFβ).

In some embodiments, the present disclosure provides methods of reducing one or more inflammatory responses in a cell, comprising exposing a sample comprising one or more cells to a pharmaceutical composition described herein, thereby preventing or reducing one or more pro-inflammatory cellular responses. In some embodiments, the sample comprises a population of cells. In some embodiments, the sample is a primary sample obtained directly from a subject. In some embodiments, a sample may be obtained from a healthy subject (i.e., a subject that does not suffer from a particular disease or condition). In some embodiments, a sample may be obtained from a subject suffering from a particular disease or condition. In some embodiments, a sample comprises cells of a cell line. In some embodiments, in vitro analyses of samples in cell culture models (e.g., using cells obtained from subjects or cell lines) are used to predict the in vivo effect of a pharmaceutical composition described herein on a subject.

2. Carydiol™ for Treatment of Neurological Diseases and Disorders

In some embodiments, the present disclosure provides a method of treating a neurological disease or disorder in a subject in need thereof, comprising administering to the subject a composition containing one or more active ingredients, said active ingredients comprising a therapeutically effective amount of CBD and (E)-BCP. In some embodiments, the present disclosure provides a method of treating a neurological disease or disorder in a subject in need thereof, comprising administering to the subject a composition containing one or more active ingredients, said active ingredients consisting essentially of a therapeutically effective amount of CBD and (E)-BCP. In some embodiments, the present disclosure provides a method of treating a neurological disease or disorder in a subject in need thereof, comprising administering to the subject a composition containing one or more active ingredients, said active ingredients consisting of a therapeutically effective amount of CBD and (E)-BCP.

In some embodiments, the present disclosure provides a method of treating a neurological disease or disorder in a subject in need thereof, comprising administering to the subject a composition containing one or more active ingredients, said active ingredients comprising a therapeutically effective amount of CBD, (E)-BCP, and THC. In some embodiments, the present disclosure provides a method of treating a neurological disease or disorder in a subject in need thereof, comprising administering to the subject a composition containing one or more active ingredients, said active ingredients consisting essentially of a therapeutically effective amount of CBD, (E)-BCP, and THC. In some embodiments, the present disclosure provides a method of treating a neurological disease or disorder in a subject in need thereof, comprising administering to the subject a composition containing one or more active ingredients, said active ingredients consisting of a therapeutically effective amount of CBD, (E)-BCP, and THC.

Neurological disorders include, but are not limited to, anxiety, depression, memory loss, dementia, sleep apnea, stroke, urinary incontinence, narcolepsy, essential tremor, epilepsy, movement disorder, atrial fibrillation, epilepsy, cancer (e.g., brain tumors), Parkinson's disease, and Alzheimer's disease.

In some embodiments, the compositions and methods herein may be utilized to ameliorate one or more symptoms of a neurological disorder in a subject. In some cases, the frequency, duration, and/or severity of one or more symptoms of a neurological disorder is ameliorated by at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 99%, or 100%.

In some embodiments, the methods and compositions of the disclosure are utilized to treat epilepsy. In some embodiments, the present disclosure provides a method of treating epilepsy in a subject in need thereof, comprising administering to the subject a composition containing one or more active ingredients, said active ingredients comprising a therapeutically effective amount of CBD and (E)-BCP. In some embodiments, the present disclosure provides a method of treating epilepsy in a subject in need thereof, comprising administering to the subject a composition containing one or more active ingredients, said active ingredients consisting essentially of a therapeutically effective amount of CBD and (E)-BCP. In some embodiments, the present disclosure provides a method of treating epilepsy in a subject in need thereof, comprising administering to the subject a composition containing one or more active ingredients, said active ingredients consisting of a therapeutically effective amount of CBD and (E)-BCP.

In some embodiments, the present disclosure provides a method of treating epilepsy in a subject in need thereof, comprising administering to the subject a composition containing one or more active ingredients, said active ingredients comprising a therapeutically effective amount of CBD, (E)-BCP, and THC. In some embodiments, the present disclosure provides a method of treating epilepsy in a subject in need thereof, comprising administering to the subject a composition containing one or more active ingredients, said active ingredients consisting essentially of a therapeutically effective amount of CBD, (E)-BCP, and THC. In some embodiments, the present disclosure provides a method of treating epilepsy in a subject in need thereof, comprising administering to the subject a composition containing one or more active ingredients, said active ingredients consisting of a therapeutically effective amount of CBD, (E)-BCP, and THC.

In some embodiments, the pharmaceutical compositions described herein may be used to prevent or control epileptic seizures. Epileptic seizures may be classified as tonic-clonic, tonic, clonic, myoclonic, absence, or atonic seizures. In some cases, the compositions and methods herein may prevent or reduce the number of epileptic seizures experienced by a subject by about 5%, about 10%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 99% or 100%.

3. Carydiol™ as a Treatment for Addiction

In recent years, accumulating scientific evidence has started to uncover a potential link between substance dependence and the animal endocannabinoid system (ECS). In humans, the ECS is regulated by endogenous bioactive lipid-derived endocannabinoid ligands that act through the cannabinoid receptors CB1 and CB2, which couple to the Gαi/o class of G-proteins and have presynaptic or postsynaptic distribution in the brain peripheral nervous system, and the immune system (Breivogel and Childers, 1998 "The functional neuroanatomy of brain cannabinoid receptors" Neurobiol Dis 5:417-431; Maldonado et al., 2006 "Involvement of the endocannabinoid system in drug addiction" Trends Neurosci 29:225-232).

Recent studies have uncovered specific links between the ECS and the reinforcing effects of alcohol (Erdozain and Callado, 2011 Involvement of the endocannabinoid system in alcohol dependence: the biochemical, behavioral and genetic evidence" Drug Alcohol Depend 117:102-110), opioids (Manzanedo et al., 2004 "Cannabinoid agonist-induced sensitization to morphine place preference in mice" Neuroreport 15:1373-1377), nicotine (Viveros et al., 2007 "The role of the hippocampus in mediating emotional responses to nicotine and cannabinoids: a possible neural substrate for functional interactions" Behav Pharmacol 18:375-389) and cocaine (Tanda, 2007 "Modulation of the endocannabinoid system: therapeutic potential against cocaine dependence" Pharmacol Res 56:406-417).

The present invention further elucidates the link between the ECS and addiction by providing novel compositions and methods for the treatment of addiction. Without wishing to be bound by any one theory, the inventors of the present disclosure believe that the disclosed pharmaceutical compositions comprising a CB1 agonist, a CB2 agonist, and a CB2 inverse agonist result in a unique and synergistic modulation of the ECS to treat addiction.

In some embodiments, the present disclosure provides a method of treating substance addiction in a subject in need thereof, comprising administering to the subject a composition containing one or more active ingredients, said active ingredients comprising a therapeutically effective amount of CBD and (E)-BCP. In some embodiments, the present disclosure provides a method of treating substance addiction in a subject in need thereof, comprising administering to the subject a composition containing one or more active ingredients, said active ingredients consisting essentially of a therapeutically effective amount of CBD and (E)-BCP. In some embodiments, the present disclosure provides a method of treating substance addiction in a subject in need thereof, comprising administering to the subject a composition containing one or more active ingredients, said active ingredients consisting of a therapeutically effective amount of CBD and (E)-BCP.

In some embodiments, the present disclosure provides a method of treating substance addiction in a subject in need thereof, comprising administering to the subject a composition containing one or more active ingredients, said active ingredients comprising a therapeutically effective amount of CBD, (E)-BCP, and THC. In some embodiments, the present disclosure provides a method of treating substance addiction in a subject in need thereof, comprising administering to the subject a composition containing one or more active ingredients, said active ingredients consisting essentially of a therapeutically effective amount of CBD, (E)-BCP, and THC. In some embodiments, the present disclosure provides a method of treating substance addiction in a subject in need thereof, comprising administering to the subject a composition containing one or more active ingredients, said active ingredients consisting of a therapeutically effective amount of CBD, (E)-BCP, and THC.

In some embodiments, treatment of a subject with the presently disclosed pharmaceuticals results in a 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% reduction in the intake of drug or alcohol compared to an untreated subject.

In some embodiments, treatment of a subject with the presently disclosed pharmaceuticals results in a cravings decrease of at least 10% as measured by a 10 point cravings test. In some embodiments, treatment of a subject with the presently disclosed pharmaceuticals results in a cravings decrease of at least 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% as measured by a 10 point cravings test.

4. Carydiol™ as a Treatment for Pain

The present invention contemplates, in part, compositions and methods for controlling, managing, preventing, or treating pain in a subject. "Pain" refers to an uncomfortable feeling and/or an unpleasant sensation in the body of a subject. Feelings of pain can range from mild and occasional to severe and constant.

Pain can be classified as acute pain or chronic pain. "Acute pain" refers to pain that begins suddenly and is usually sharp in quality. Acute pain might be mild and last just a moment, or it might be severe and last for weeks or months. In most cases, acute pain does not last longer than three months, and it disappears when the underlying cause of pain has been treated or has healed. Unrelieved acute pain, however, may lead to chronic pain. "Chronic pain" refers to ongoing or recurrent pain, lasting beyond the usual course of acute illness or injury or lasting for more than three to six months, and which adversely affects the individual's well-being. In particular embodiments, the term "chronic pain" refers to pain that continues when it should not. Chronic pain can be nociceptive pain or neuropathic pain.

Pain can be nociceptive pain (i.e., pain caused by tissue damage), neuropathic pain or psychogenic pain. In some cases, the pain is caused by or associated with a disease (e.g., cancer, arthritis, diabetes). In other cases, the pain is caused by injury (e.g., sports injury, trauma). Non-limiting examples of pain that are amenable to treatment with the compositions and methods herein include: neuropathic pain including peripheral neuropathy, diabetic neuropathy, post herpetic neuralgia, trigeminal neuralgia, back pain, neuropathy associated with cancer, neuropathy associated with HIV/AIDS, phantom limb pain, carpal tunnel syndrome, central post-stroke pain, pain associated with chronic alcoholism, hypothyroidism, uremia, pain associated with multiple sclerosis, pain associated with spinal cord injury, pain associated with Parkinson's disease, epilepsy, osteoarthritic pain, rheumatoid arthritic pain, visceral pain, and pain associated with vitamin deficiency; and nociceptive pain including pain associated with central nervous system trauma, strains/sprains, and burns; myocardial infarction, acute pancreatitis, post-operative pain, posttraumatic pain, renal colic, pain associated with cancer, pain associated with fibromyalgia, pain associated with carpal tunnel syndrome, and back pain.

In some embodiments, the present disclosure provides a method of treating pain in a subject in need thereof, comprising administering to the subject a composition containing one or more active ingredients, said active ingredients comprising a therapeutically effective amount of CBD and (E)-BCP. In some embodiments, the present disclosure provides a method of treating pain in a subject in need thereof, comprising administering to the subject a composition containing one or more active ingredients, said active ingredients consisting essentially of a therapeutically effective amount of CBD and (E)-BCP. In some embodiments, the present disclosure provides a method of treating pain in a subject in need thereof, comprising administering to the subject a composition containing one or more active ingredients, said active ingredients consisting of a therapeutically effective amount of CBD and (E)-BCP.

In some embodiments, the present disclosure provides a method of treating pain in a subject in need thereof, comprising administering to the subject a composition containing one or more active ingredients, said active ingredients comprising a therapeutically effective amount of CBD, (E)-BCP, and THC. In some embodiments, the present disclosure provides a method of treating pain in a subject in need thereof, comprising administering to the subject a composition containing one or more active ingredients, said active ingredients consisting essentially of a therapeutically effective amount of CBD, (E)-BCP, and THC. In some embodiments, the present disclosure provides a method of treating pain in a subject in need thereof, comprising administering to the subject a composition containing one or more active ingredients, said active ingredients consisting of a therapeutically effective amount of CBD, (E)-BCP, and THC.

The compositions and methods herein may be utilized to ameliorate a level of pain in a subject. In some cases, a level of pain in a subject is ameliorated by at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 99%, or 100%. A level of pain in a subject can be assessed by a variety of methods. In some cases, a level of pain is assessed by self-reporting (i.e., a human subject expresses a verbal report of the level of pain he/she is experiencing). In some cases, a level of pain is assessed by behavioral indicators of pain, for example, facial expressions, limb movements, vocalization, restlessness and guarding. These types of assessments may be useful for example when a subject is unable to self-report (e.g., an infant, an unconscious subject, a non-human subject). A level of pain may be assessed after treatment with a composition of the disclosure as compared to the level of pain the subject was experiencing prior to treatment with the composition.

B. Carydiol™ and F-CBD Methods of Treating Skin Disorders

In some embodiments, the present disclosure provides methods of treating an inflammatory skin disease or condition. Inflammatory skin diseases or conditions include, for example, atopic dermatitis, contact dermatitis, allergic dermatitis, pruritic dermatitis, solar (UVB-induced) dermatitis, chemical-induced dermatitis, bacterial and viral skin inflammation, acne, and psoriasis.

Symptoms of inflammatory skin diseases may include, for example, raised bumps that are red or white, a rash (which might be painful or itchy), scaly or rough skin, peeling skin, skin ulcers, open sores or lesions; dry, cracked skin; and discolored patches of skin.

Atopic dermatitis is an allergic disease caused by a defect of a stratum corneum, which is a protective wall located in the outermost part of the skin, caused by hereditary, environmental, or immunological factors and is exacerbated in arid climate. The symptoms of atopic dermatitis include severe pruritus (itch), xeroderma, eruption or oozing of the skin, boils, scale like skin (scaly skin), etc. Scratching worsens symptoms and affected people have an increased risk of skin infections.

Psoriasis is an autoimmune disease characterized by patches of abnormal skin. These skin patches are typically red, itchy, and scaly. They may vary in severity from small and localized to complete body coverage. Injury to the skin can trigger psoriatic skin changes at that spot. There are five main types of psoriasis: plaque, guttate, inverse, pustular, and erythrodermic. Plaque psoriasis, also known as psoriasis vulgaris, makes up about 90% of cases.

Acne vulgaris is the formation of comedones (whiteheads or blackheads), papules, pustules, nodules, and/or cysts as a result of obstruction and inflammation of pilosebaceous units (hair follicles and their accompanying sebaceous gland). Acne develops on the face and upper trunk.

In some embodiments, the present disclosure provides methods of treating an inflammatory skin disease or condition in a subject in need thereof, comprising administering a therapeutically effective amount of a pharmaceutical composition comprising one or more F-CBDs to the subject in need thereof.

In some embodiments, the present disclosure provides methods of treating an inflammatory skin disease or condition selected from the group consisting of atopic dermatitis, contact dermatitis, allergic dermatitis, pruritic dermatitis, solar (UVB-induced) dermatitis, chemical-induced dermatitis, bacterial and viral skin inflammation, acne and psoriasis, in a subject in need thereof, comprising administering a therapeutically effective amount of a pharmaceutical composition comprising one or more F-CBDs to the subject in need thereof.

In some embodiments, the present disclosure provides methods of treating an inflammatory skin disease or condition selected from the group consisting of contact dermatitis, allergic dermatitis, pruritic dermatitis, solar (UVB-induced) dermatitis, chemical-induced dermatitis, and bacterial and viral skin inflammation, in a subject in need thereof, comprising administering a therapeutically effective amount of a pharmaceutical composition comprising one or more F-CBDs to the subject in need thereof.

In some embodiments, the present disclosure provides methods of treating atopic dermatitis comprising administering a therapeutically effective amount of a pharmaceutical composition comprising one or more F-CBDs to the subject in need thereof.

In some embodiments, the present disclosure provides methods of treating acne comprising administering a therapeutically effective amount of a pharmaceutical composition comprising one or more F-CBDs to the subject in need thereof.

In some embodiments, the present disclosure provides methods of treating psoriasis comprising administering a therapeutically effective amount of a pharmaceutical composition comprising one or more F-CBDs to the subject in need thereof.

In some embodiments, the F-CBD is a compound selected from a compound of Formula (I), a compound of Formula (Ia), a compound of Formula (II), a compound of Formula (Ha), a compound of Formula (III), a compound of Formula (Ma), a compound of Formula (IV), a compound of Formula (IVa), a compound of Formula (V), or a compound of Formula (VI), described herein.

In some embodiments, the F-CBD is a compound selected the following compounds:

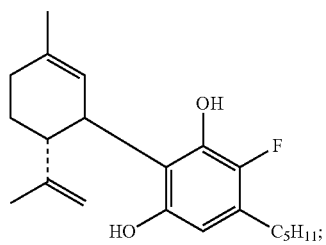

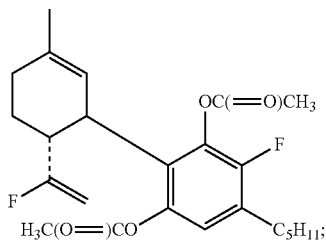

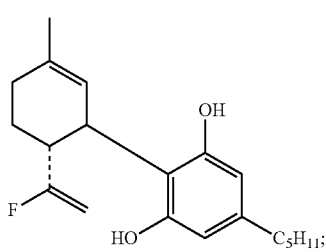

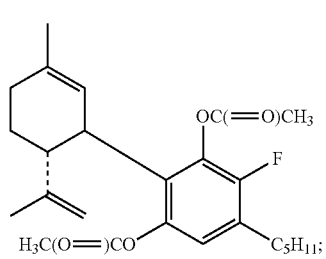

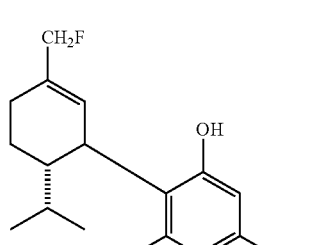

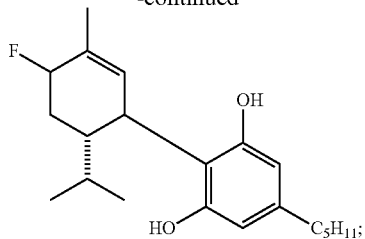

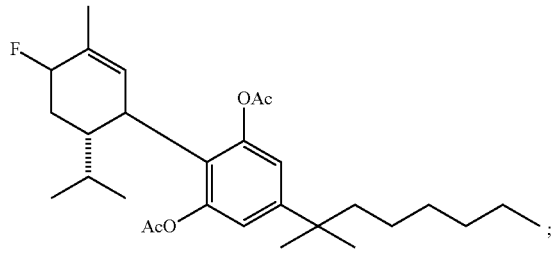

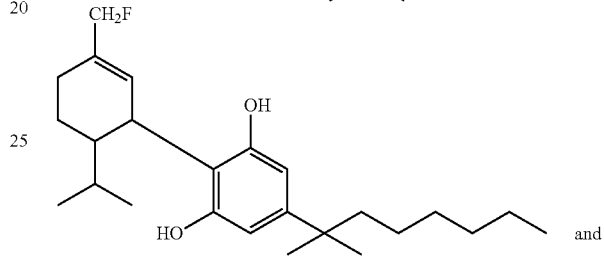

and

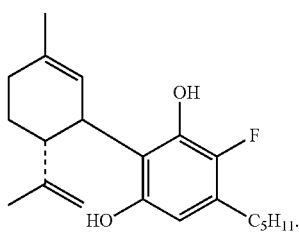

.

In some embodiments, the F-CBD is a compound of formula

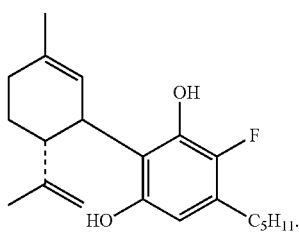

In some embodiments, the present disclosure provides methods of treating a disease or condition in a subject in need thereof comprising administering a pharmaceutical composition described herein (e.g. a Carydiol™ composition) to the subject in order to treat said disease or condition In some embodiments, the present disclosure provides methods of treating an inflammatory skin disease or condition, in a subject in need thereof, comprising administering a therapeutically effective amount of a pharmaceutical composition comprising CBD and (E)-BCP to the subject in need thereof. In some embodiments, the present disclosure provides methods of treating an inflammatory skin disease or condition, in a subject in need thereof, comprising administering a therapeutically effective amount of a pharmaceutical composition consisting essentially of CBD and (E)-BCP to the subject in need thereof. In some embodiments, the present disclosure provides methods of treating an inflammatory skin disease or condition, in a subject in need thereof, comprising administering a therapeutically effective amount of a pharmaceutical composition consisting of CBD and (E)-BCP to the subject in need thereof.

In some embodiments, the present disclosure provides methods of treating an inflammatory skin disease or condition selected from the group consisting of atopic dermatitis, contact dermatitis, allergic dermatitis, pruritic dermatitis, solar (UVB-induced) dermatitis, chemical-induced dermatitis, bacterial and viral skin inflammation, acne and psoriasis, in a subject in need thereof, comprising administering a therapeutically effective amount of a pharmaceutical composition comprising CBD and (E)-BCP to the subject in need thereof. In some embodiments, the present disclosure provides methods of treating an inflammatory skin disease or condition selected from the group consisting of atopic dermatitis, contact dermatitis, allergic dermatitis, pruritic dermatitis, solar (UVB-induced) dermatitis, chemical-induced dermatitis, bacterial and viral skin inflammation, acne and psoriasis, in a subject in need thereof, comprising administering a therapeutically effective amount of a pharmaceutical composition consisting essentially of CBD and (E)-BCP to the subject in need thereof. In some embodiments, the present disclosure provides methods of treating an inflammatory skin disease or condition selected from the group consisting of atopic dermatitis, contact dermatitis, allergic dermatitis, pruritic dermatitis, solar (UVB-induced) dermatitis, chemical-induced dermatitis, bacterial and viral skin inflammation, acne and psoriasis, in a subject in need thereof, comprising administering a therapeutically effective amount of a pharmaceutical composition consisting of CBD and (E)-BCP to the subject in need thereof.

In some embodiments, the present disclosure provides methods of treating an inflammatory skin disease or condition selected from the group consisting of contact dermatitis, allergic dermatitis, pruritic dermatitis, solar (UVB-induced) dermatitis, chemical-induced dermatitis, and bacterial and viral skin inflammation, in a subject in need thereof, comprising administering a therapeutically effective amount of a pharmaceutical composition comprising CBD and (E)-BCP to the subject in need thereof.

In some embodiments, the present disclosure provides methods of treating atopic dermatitis comprising administering a therapeutically effective amount of a pharmaceutical composition comprising CBD and (E)-BCP to the subject in need thereof. In some embodiments, the present disclosure provides methods of treating atopic dermatitis comprising administering a therapeutically effective amount of a pharmaceutical composition consisting essentially of CBD and (E)-BCP to the subject in need thereof. In some embodiments, the present disclosure provides methods of treating atopic dermatitis comprising administering a therapeutically effective amount of a pharmaceutical composition consisting of CBD and (E)-BCP to the subject in need thereof.

In some embodiments, the present disclosure provides methods of treating acne comprising administering a therapeutically effective amount of a pharmaceutical composition comprising CBD and (E)-BCP to the subject in need thereof. In some embodiments, the present disclosure provides methods of treating acne comprising administering a therapeutically effective amount of a pharmaceutical composition consisting essentially of CBD and (E)-BCP to the subject in need thereof. In some embodiments, the present disclosure provides methods of treating acne comprising administering a therapeutically effective amount of a pharmaceutical composition consisting of CBD and (E)-BCP to the subject in need thereof.

In some embodiments, the present disclosure provides methods of treating psoriasis comprising administering a therapeutically effective amount of a pharmaceutical composition comprising CBD and (E)-BCP to the subject in need thereof. In some embodiments, the present disclosure provides methods of treating psoriasis comprising administering a therapeutically effective amount of a pharmaceutical composition consisting essentially of CBD and (E)-BCP to the subject in need thereof. In some embodiments, the present disclosure provides methods of treating psoriasis comprising administering a therapeutically effective amount of a pharmaceutical composition consisting of CBD and (E)-BCP to the subject in need thereof.

In some embodiments, the pharmaceutical composition for treating an inflammatory skin disease or condition is administered in a topical dosage form. In some embodiments, the topical dosage form is selected from a solid (e.g., dusting powder), liquid (e.g., lotion, liniment) and semi-liquid (e.g., ointment, paste, cream and gel).

EXAMPLES

The following examples are given for the purpose of illustrating various embodiments of the disclosure and are not meant to limit the present disclosure in any fashion. Changes therein and other uses which are encompassed within the spirit of the disclosure, as defined by the scope of the claims, will occur to those skilled in the art.

Example 1: Anti-Inflammatory Properties of CBD and BCP Measured Using RAW-Blue™ Cells RAW 264.7 macrophages are commonly used to study the functional characteristics of the endocannabinoid system (ECS). Specifically, this model is widely employed to assess the anti-inflammatory functions of the ECS (Carrier, et al. 2006, "Inhibition of an equilibrative nucleoside transporter by cannabidiol: A mechanism of cannabinoid immunosuppression," PNAS, 103(20), 7895-7900). RAW-Blue™ cells are derived from RAW 264.7 macrophages and are genetically modified to comprise a secreted embryonic alkaline phosphatase (SEAP) reporter construct that is inducible by NF-κB and AP-1. These RAW-Blue™ cells express a variety of pattern recognition receptors, including Toll like receptor 4 (TLR4). The activation of these pattern recognition receptors on the RAW-Blue™ cells (e.g., by lipopolysaccharide (LPS) in the case of TLR4) induces signaling through NF-κB and/or AP-1, thereby leading to increased secretion of the SEAP reporter gene. Therefore, the RAW-Blue™ macrophages and provide a robust, high-throughput model of inflammatory processes.

A three-phase study was performed to assess the anti-inflammatory properties of CBD and BCP, alone and in combination:
  (a) Phase 1: Screening of CBD and BCP individually in the RAW-Blue™ cellular model;
  (b) Phase 2: Screening of various combinations of CBD and BCP concentrations in the RAW-Blue™ cells to determine and optimize synergistic anti-inflammatory effects; and
  (c) Phase 3: Determine the anti-inflammatory effect of adding various concentrations of THC to select synergistic CBD-BCP combinations.

Cell Culture:

RAW-Blue™ cells were cultured in high-glucose containing Dulbecco's Modified Eagle Medium (Merck) supplemented with 10 (V/V) % fetal bovine serum (FBS; ThermoFisher), 2-4 mM L-glutamine, 50 U/mL penicillin, 50 µg/mL streptomycin as well as with antibiotics for selection: 100 µg/mL Normocin™ (InvivoGen) and Zeocin™ (InvivoGen). Cells were cultured at 37° C. in humidified, 5% $CO_2$ containing atmosphere. The medium was changed every other day, and cells were sub-cultured at 70-80% confluence.

Inflammatory Challenge and Quanti-Blue™ Assay Protocols:

For each of these phases, 100,000 RAW-Blue™ cells/well were seeded in a 96-well plate in triplicate and cultured for 24 hours to allow attachment of the macrophages to the cell culture plate. After 24 hrs cells were pre-treated with selected concentrations of CBD, BCP, or CBD+BCP. Two hours after drug pre-treatment, cells were stimulated with 0.1 µg/mL LPS (Sigma-Aldrich) to induce activation of the TLR4 pathway. After 24 hours of LPS stimulation, 150 µL Quanti-Blue™ Medium was aliquoted per well in a 96-well plate and 50 µL of the experimental supernatants were added per well. Cell culture medium was used as negative control. After 1 hour incubation, SEAP levels were detected by measuring absorbance levels at $\lambda=650$ nm at 37° C. Results are expressed as a % decrease in SEAP levels in drug-treated, LPS-stimulated groups compared to the SEAP level of the untreated, LPS-stimulated group (regarded as 100%). All experiments were repeated 2-3 times.

Cell Viability Assays:

In order to exclude putative cytotoxicity of the drugs, cellular viability was also measured throughout the experimental series using a colorimetric MTT. For these assays, cells were plated into 96-well plates at 20,000 cells/well and cultured for 24, 48, or 72 hours in the presence of CBD, BCP, or CBD+BCP. Cells were then incubated with 0.5 mg/mL MTT for 2-3 hours, and the concentration of formazan crystals (as an indicator of number of viable cells) was determined by measuring absorbance levels at $\lambda=550$ nm). Cytotoxic drug concentrations/combinations identified in the MTT assays were omitted from further analysis.

Results:

Phase 1—Effects of CDB and BCP Alone:

Ten (10) concentrations of CBD and thirteen (13) concentrations of BCP were individually tested in the RAW-Blue™ cellular model. The following concentrations of CBD were tested: 30, 10, 3, 1, 0.3, 0.1, 0.01, 0.001, 0.0001, and 0.00001 µM. The following concentrations of BCP were tested: 300, 100, 30, 10, 3, 1, 0.3, 0.13, 0.1, 0.013, 0.01, 0.001, and 0.0001 µM. The results of these experiments are shown below in Table 1.

TABLE 1

Effects of CBD and BCP treatment in high-throughput inflammatory assay

| CBD (µM) | % Inhibition | BCP (µM) | % Inhibition |
|---|---|---|---|
| 0.00001 | 1.9 ± 0.9 | 0.0001 | 0 |
| 0.0001 | 2.4 ± 2 | 0.001 | 1 ± 0.8 |
| 0.001 | 3.1 ± 3.1 | 0.01 | 3.8 ± 1.9 |
| 0.01 | 5.8 ± 2.9 | 0.013 | 9.2 ± 3.5 |
| 0.1 | 8.5 ± 1.4 | 0.1 | 8 ± 6.4 |
| 0.3 | 10.0 ± 0.8 | 0.13 | 0 |
| 1 | 44.6 ± 5.8 | 0.3 | 1.6 ± 1.4 |
| 3 | 40.5 ± 9.5 | 1 | 2.5 ± 2 |
| 10 | 59.3 ± 3.7 | 3 | 1.25 ± 1 |
| 30 | 78 ± 7.9* | 10 | 28.6 ± 14.3 |
|  |  | 30 | 0 |
|  |  | 100 | 11.7 ± 5.8 |
|  |  | 300 | 92.2 ± 17.1* |

*indicates possibly cytotoxicity

These data demonstrate that CBD, when applied alone, exerted "classical" dose-dependent effect on SEAP levels, i.e. marked effects were observed at ≥1 µM concentrations. Conversely, BCP, when applied alone, exerted only minor (if any) anti-inflammatory actions. Notably, 30 µM CBD and 300 µM BCP appeared to induce toxicity (as determined by MTT assay). Therefore, data obtained at this concentration were omitted from the analyses.

Phase 2—Combined Effects of CDB and BCP:

Each of the 10 CBD concentrations from Phase 1 were combined with each of the 13 concentrations of BCP from Phase 1 (130 different combinations) and were assessed in RAW-Blue™ cells. FIG. 16 shows the resulting molar ratios of CBD:BCP that were tested.

The percent inhibition of SEAP levels for each combination compared to LPS-stimulated, vehicle-treated controls is shown below in Table 2. To assess the effects of CBD+BCP combinations, the combined anti-inflammatory effects were compared to those obtained with the respective individual concentrations of CBD or BCP in Phase 1.

TABLE 2

Effects of CBD + BCP combination treatment in high-throughput assay of inflammation

| Molar Ratio (CBD:BCP) | CBD µM | % Inhibition CBD Alone | BCP µM | % Inhibition BCP Alone | % Inhibition Combined |
|---|---|---|---|---|---|
| 0:1 | 0 | NA | 0.0001 | 0 | NA |
|  | 0 | NA | 0.001 | 1 ± 0.8 | NA |
|  | 0 | NA | 0.01 | 3.8 ± 1.9 | NA |
|  | 0 | NA | 0.013 | 9.2 ± 3.5 | NA |
|  | 0 | NA | 0.1 | 8 ± 6.4 | NA |
|  | 0 | NA | 0.13 | 0 | NA |
|  | 0 | NA | 0.3 | 1.6 ± 1.4 | NA |
|  | 0 | NA | 1 | 2.5 ± 2 | NA |
|  | 0 | NA | 3 | 1.25 ± 1 | NA |
|  | 0 | NA | 10 | 28.6 ± 14.3 | NA |
|  | 0 | NA | 30 | 0 | NA |
|  | 0 | NA | 100 | 11.7 ± 5.8 | NA |
|  | 0 | NA | 300 | *92.2 ± 17.1 | NA |

TABLE 2-continued

Effects of CBD + BCP combination treatment in high-throughput assay of inflammation

| Molar Ratio (CBD:BCP) | CBD μM | % Inhibition CBD Alone | BCP μM | % Inhibition BCP Alone | % Inhibition Combined |
|---|---|---|---|---|---|
| 1:0 | 0.00001 | 1.9 ± 0.9 | 0 | NA | NA |
|  | 0.0001 | 2.4 ± 2 | 0 | NA | NA |
|  | 0.001 | 3.1 ± 3.1 | 0 | NA | NA |
|  | 0.01 | 5.8 ± 2.9 | 0 | NA | NA |
|  | 0.1 | 8.5 ± 1.4 | 0 | NA | NA |
|  | 0.3 | 10.0 ± 0.8 | 0 | NA | NA |
|  | 1 | 44.6 ± 5.8 | 0 | NA | NA |
|  | 3 | 40.5 ± 9.5 | 0 | NA | NA |
|  | 10 | 59.3 ± 3.7 | 0 | NA | NA |
|  | 30 | 78 ± 7.9* | 0 | NA | NA |
| 1:30000000 | 0.00001 | 1.9 ± 0.9 | 300 | *92.2 ± 17.1 | *95.1 ± 2.6* |
| 1:10000000 | 0.00001 | 1.9 ± 0.9 | 100 | 11.7 ± 5.8 | 0 |
| 1:3000000 | 0.00001 | 1.9 ± 0.9 | 30 | 0 | 8.5 ± 1.1 |
|  | 0.0001 | 2.4 ± 2 | 300 | *92.2 ± 17.1 | *95.0 ± 0.7 |
| 1:1000000 | 0.0001 | 2.4 ± 2 | 100 | 11.7 ± 5.8 | 0 |
|  | 0.00001 | 1.9 ± 0.9 | 10 | 28.6 ± 14.3 | 2.3 ± 0.6 |
| 1:300000 | 0.0001 | 2.4 ± 2 | 30 | 0 | 3.7 ± 0.8 |
|  | 0.001 | 3.1 ± 3.1 | 300 | *92.2 ± 17.1 | *94.9 ± 1.7 |
|  | 0.00001 | 1.9 ± 0.9 | 3 | 1.25 ± 1 | 0 |
| 1:100000 | 0.00001 | 1.9 ± 0.9 | 1 | 2.5 ± 2 | 3.1 ± 0 |
|  | 0.0001 | 2.4 ± 2 | 10 | 28.6 ± 14.3 | 8 ± 2.7 |
|  | 0.001 | 3.1 ± 3.1 | 100 | 11.7 ± 5.8 | 0 |
| 1:30000 | 0.00001 | 1.9 ± 0.9 | 0.3 | 1.6 ± 1.4 | 0 |
|  | 0.0001 | 2.4 ± 2 | 3 | 1.25 ± 1 | 1.8 ± 2.9 |
|  | 0.001 | 3.1 ± 3.1 | 30 | 0 | 13.9 ± 11.2 |
|  | 0.01 | 5.8 ± 2.9 | 300 | *92.2 ± 17.1 | *95.0 ± 1.5 |
| 1:13000 | 0.00001 | 1.9 ± 0.9 | 0.13 | 0 | 0 |
| 1:10000 | 0.00001 | 1.9 ± 0.9 | 0.1 | 8 ± 6.4 | 9.9 ± 1.2 |
|  | 0.0001 | 2.4 ± 2 | 1 | 2.5 ± 2 | 1.5 ± 1.5 |
|  | 0.001 | 3.1 ± 3.1 | 10 | 28.6 ± 14.3 | 3.4 ± 3.4 |
|  | 0.01 | 5.8 ± 2.9 | 100 | 11.7 ± 5.8 | 0.3 ± 0 |
| 1:3000 | 0.001 | 3.1 ± 3.1 | 3 | 1.25 ± 1 | 4.6 ± 4.6 |
|  | 0.01 | 5.8 ± 2.9 | 30 | 0 | 0 |
|  | 0.0001 | 2.4 ± 2 | 0.3 | 1.6 ± 1.4 | 3.8 ± 2.5 |
|  | 0.1 | 8.5 ± 1.4 | 300 | *92.2 ± 17.1 | *95.0 ± 1.3 |
| 1:1300 | 0.0001 | 2.4 ± 2 | 0.13 | 0 | 0 |
|  | 0.00001 | 1.9 ± 0.9 | 0.013 | 9.2 ± 3.5 | 0 |
| 1:1000 | 0.00001 | 1.9 ± 0.9 | 0.01 | 3.8 ± 1.9 | 0 |
|  | 0.0001 | 2.4 ± 2 | 0.1 | 8 ± 6.4 | 4.4 ± 2.2 |
|  | 0.001 | 3.1 ± 3.1 | 1 | 2.5 ± 2 | 12.2 ± 6.6 |
|  | 0.01 | 5.8 ± 2.9 | 10 | 28.6 ± 14.3 | 1.9 ± 1.9 |
|  | 0.1 | 8.5 ± 1.4 | 100 | 11.7 ± 5.8 | 0.8 ± 0 |
|  | 0.3 | 10 ± 0.8 | 300 | *92.2 ± 17.1 | *95.0 ± 0.7 |
| 1:333 | 0.3 | 10 ± 0.8 | 100 | 11.7 ± 5.8 | 19.0 ± 5.0 |
| 1:300 | 0.001 | 3.1 ± 3.1 | 0.3 | 1.6 ± 1.4 | 8.4 ± 7.8 |
|  | 0.01 | 5.8 ± 2.9 | 3 | 1.25 ± 1 | 6.8 ± 3.4 |
|  | 0.1 | 8.5 ± 1.4 | 30 | 0 | 33.4 ± 15.9 |
|  | 1 | 44.6 ± 5.8 | 300 | *92.2 ± 17.1 | *95.1 ± 0.9 |
| 1:130 | 0.001 | 3.1 ± 3.1 | 0.13 | 0 | 2.3 ± 1 |
|  | 0.0001 | 2.4 ± 2 | 0.013 | 9.2 ± 3.5 | 0 |
| 1:100 | 0.00001 | 1.9 ± 0.9 | 0.001 | 1 ± 0.8 | 1.9 ± 1.5 |
|  | 0.0001 | 2.4 ± 2 | 0.01 | 3.8 ± 1.9 | 4 ± 4 |
|  | 0.001 | 3.1 ± 3.1 | 0.1 | 8 ± 6.4 | 20.5 ± 14.5 |
|  | 0.01 | 5.8 ± 2.9 | 1 | 2.5 ± 2 | 11.7 ± 5.8 |
|  | 0.1 | 8.5 ± 1.4 | 10 | 28.6 ± 14.3 | 1.9 ± 1.9 |
|  | 0.3 | 10 ± 0.8 | 30 | 0 | 34.7 ± 4.2 |
|  | 1 | 44.6 ± 5.8 | 100 | 11.7 ± 5.8 | 44.9 ± 18.2 |
|  | 3 | 40.5 ± 9.5 | 300 | *92.2 ± 17.1 | *95.0 ± 1.1 |
| 1:33.3 | 0.3 | 10 ± 0.8 | 10 | 28.6 ± 14.3 | 12.5 ± 1 |
|  | 3 | 40.5 ± 9.5 | 100 | 11.7 ± 5.8 | 85.5 ± 39.4 |
| 1:30 | 0.01 | 5.8 ± 2.9 | 0.3 | 1.6 ± 1.4 | 5.3 ± 3.9 |
|  | 0.1 | 8.5 ± 1.4 | 3 | 1.25 ± 1 | 75.9 ± 8.2 |
|  | 1 | 44.6 ± 5.8 | 30 | 0 | 18.4 ± 2.2 |
|  | 10 | 59.3 ± 3.7 | 300 | *92.2 ± 17.1 | *95.1 ± 1.4 |
| 1:13 | 0.001 | 3.1 ± 3.1 | 0.013 | 9.2 ± 3.5 | 0 |
|  | 0.01 | 5.8 ± 2.9 | 0.13 | 0 | 4.2 ± 2.3 |
| 1:10 | 0.01 | 5.8 ± 2.9 | 0.1 | 8 ± 6.4 | 8.9 ± 4.4 |
|  | 0.3 | 10 ± 0.8 | 3 | 1.25 ± 1 | 70.9 ± 8.9 |
|  | 0.00001 | 1.9 ± 0.9 | 0.0001 | 0 | 1.1 ± 0.5 |
|  | 0.0001 | 2.4 ± 2 | 0.001 | 1 ± 0.8 | 4.2 ± 2.1 |
|  | 0.001 | 3.1 ± 3.1 | 0.01 | 3.8 ± 1.9 | 7.7 ± 5.1 |
|  | 0.1 | 8.5 ± 1.4 | 1 | 2.5 ± 2 | 88.7 ± 2.7 |
|  | 1 | 44.6 ± 5.8 | 10 | 28.6 ± 14.3 | 90.9 ± 4.7 |
|  | 3 | 40.5 ± 9.5 | 30 | 0 | 44.4 ± 11.7 |

TABLE 2-continued

Effects of CBD + BCP combination treatment in high-throughput assay of inflammation

| Molar Ratio (CBD:BCP) | CBD μM | % Inhibition CBD Alone | BCP μM | % Inhibition BCP Alone | % Inhibition Combined |
|---|---|---|---|---|---|
| | 10 | 59.3 ± 3.7 | 100 | 11.7 ± 5.8 | 98.8 ± 4.3 |
| | 30 | *78 ± 7.9 | 300 | *92.2 ± 17.1 | *95.1 ± 1.1 |
| 1:3.33 | 0.3 | 10 ± 0.8 | 1 | 2.5 ± 2 | 70.7 ± 7.7 |
| | 3 | 40.5 ± 9.5 | 10 | 28.6 ± 14.3 | 58 ± 10.9 |
| | 30 | *78 ± 7.9 | 100 | 11.7 ± 5.8 | *93.1 ± 1.6 |
| 1:3 | 1 | 44.6 ± 5.8 | 3 | 1.25 ± 1 | 47.5 ± 7.6 |
| | 10 | 59.3 ± 3.7 | 30 | 0 | 45.0 ± 1.8 |
| | 0.1 | 8.5 ± 1.4 | 0.3 | 1.6 ± 1.4 | 6.1 ± 3.9 |
| 1:1.3 | 0.01 | 5.8 ± 2.9 | 0.013 | 9.2 ± 3.5 | 5.3 ± 1.6 |
| | 0.1 | 8.5 ± 1.4 | 0.13 | 0 | 16.5 ± 3.8 |
| 1:1 | 0.0001 | 2.4 ± 2 | 0.0001 | 0 | 4.2 ± 1.5 |
| | 0.001 | 3.1 ± 3.1 | 0.001 | 1 ± 0.8 | 7.6 ± 3.8 |
| | 0.01 | 5.8 ± 2.9 | 0.01 | 3.8 ± 1.9 | 2 ± 1 |
| | 0.1 | 8.5 ± 1.4 | 0.1 | 8 ± 6.4 | 10.9 ± 5.5 |
| | 0.3 | 10 ± 0.8 | 0.3 | 1.6 ± 1.4 | 86.8 ± 5.2 |
| | 1 | 44.6 ± 5.8 | 1 | 2.5 ± 2 | 83.4 ± 4.6 |
| | 3 | 40.5 ± 9.5 | 3 | 1.25 ± 1 | 49.7 ± 3.6 |
| | 10 | 59.3 ± 3.7 | 10 | 28.6 ± 14.3 | 78.6 ± 3.2 |
| | 30 | *78 ± 7.9 | 30 | 0 | *91.5 ± 83.4 |
| 1:2.3 | 0.3 | 10 ± 0.8 | 0.13 | 0 | 12.4 ± 6.2 |
| 3:1 | 0.3 | 10 ± 0.8 | 0.1 | 8 ± 6.4 | 8.3 ± 3.5 |
| | 3 | 40.5 ± 9.5 | 1 | 2.5 ± 2 | 47.3 ± 6.9 |
| | 30 | *78 ± 7.9 | 10 | 28.6 ± 14.3 | *934 ± 1.2 |
| 3.33:1 | 1 | 44.6 ± 5.8 | 0.3 | 1.6 ± 1.4 | 47.2 ± 3.2 |
| | 10 | 59.3 ± 3.7 | 3 | 1.25 ± 1 | 55.6 ± 15.3 |
| 7.69:1 | 1 | 44.6 ± 5.8 | 0.13 | 0 | 70.8 ± 16.2 |
| | 0.1 | 8.5 ± 1.4 | 0.013 | 9.2 ± 3.5 | 58.9 ± 1.2 |
| 10:1 | 0.001 | 3.1 ± 3.1 | 0.0001 | 0 | 17.5 ± 7.5 |
| | 0.01 | 5.8 ± 2.9 | 0.001 | 1 ± 0.8 | 0.7 ± 0.7 |
| | 0.1 | 8.5 ± 1.4 | 0.01 | 3.8 ± 1.9 | 4.6 ± 2.4 |
| | 1 | 44.6 ± 5.8 | 0.1 | 8 ± 6.4 | 49.2 ± 5.6 |
| | 3 | 40.5 ± 9.5 | 0.3 | 1.6 ± 1.4 | 46 ± 7.8 |
| | 10 | 59.3 ± 3.7 | 1 | 2.5 ± 2 | 85.3 ± 4.1 |
| | 30 | *78 ± 7.9 | 3 | 1.25 ± 1 | *93.4 ± 1.5 |
| 23.1:1 | 0.3 | 10 ± 0.8 | 0.013 | 9.2 ± 3.5 | 11.6 ± 5.2 |
| | 3 | 40.5 ± 9.5 | 0.13 | 0 | 36 ± 13.5 |
| 30:1 | 0.3 | 10 ± 0.8 | 0.01 | 3.8 ± 1.9 | 8.8 ± 6 |
| | 3 | 40.5 ± 9.5 | 0.1 | 8 ± 6.4 | 42.7 ± 7.9 |
| | 30 | *78 ± 7.9 | 1 | 2.5 ± 2 | *74.3 ± 0.7 |
| 33.3:1 | 10 | 59.3 ± 3.7 | 0.3 | 1.6 ± 1.4 | 63.1 ± 1.4 |
| 76.9:1 | 1 | 44.6 ± 5.8 | 0.013 | 9.2 ± 3.5 | 39.4 ± 6.8 |
| | 10 | 59.3 ± 3.7 | 0.13 | 0 | 49.2 ± 21.1 |
| 100:1 | 0.01 | 5.8 ± 2.9 | 0.0001 | 0 | 7.6 ± 5.3 |
| | 0.1 | 8.5 ± 1.4 | 0.001 | 1 ± 0.8 | 66.6 ± 7.4 |
| | 1 | 44.6 ± 5.8 | 0.01 | 3.8 ± 1.9 | 42.9 ± 2.3 |
| | 10 | 59.3 ± 3.7 | 0.1 | 8 ± 6.4 | 82.6 ± 3.7 |
| | 30 | *78 ± 7.9 | 0.3 | 1.6 ± 1.4 | *91.4 ± 0.7 |
| 231:1 | 3 | 40.5 ± 9.5 | 0.013 | 9.2 ± 3.5 | 48.2 ± 5.3 |
| | 30 | *78 ± 7.9 | 0.13 | 0 | *92.4 ± 5.5 |
| 300:1 | 0.3 | 10 ± 0.8 | 0.001 | 1 ± 0.8 | 92.6 ± 0.8 |
| | 3 | 40.5 ± 9.5 | 0.01 | 3.8 ± 1.9 | 39.9 ± 8.9 |
| | 30 | *78 ± 7.9 | 0.1 | 8 ± 6.4 | *91.5 ± 1.0 |
| 769:1 | 10 | 59.3 ± 3.7 | 0.013 | 9.2 ± 3.5 | 51 ± 15.2 |
| 1000:1 | 0.1 | 8.5 ± 1.4 | 0.0001 | 0 | 11.3 ± 5.6 |
| | 1 | 44.6 ± 5.8 | 0.001 | 1 ± 0.8 | 35.1 ± 5 |
| | 10 | 59.3 ± 3.7 | 0.01 | 3.8 ± 1.9 | 63.3 ± 6 |
| 2308:1 | 30 | *78 ± 7.9 | 0.013 | 9.2 ± 3.5 | *88.2 ± 18.4 |
| 3000:1 | 0.3 | 10 ± 0.8 | 0.0001 | 0 | 14.5 ± 7.3 |
| | 3 | 40.5 ± 9.5 | 0.001 | 1 ± 0.8 | 55.8 ± 5.8 |
| | 30 | *78 ± 7.9 | 0.01 | 3.8 ± 1.9 | *91.4 ± 0.7 |
| 10000:1 | 1 | 44.6 ± 5.8 | 0.0001 | 0 | 46.8 ± 2.8 |
| | 10 | 59.3 ± 3.7 | 0.001 | 1 ± 0.8 | 69.2 ± 5.3 |
| 30000:1 | 3 | 40.5 ± 9.5 | 0.0001 | 0 | 42.1 ± 6.8 |
| | 30 | *78 ± 7.9 | 0.001 | 1 ± 0.8 | *91.4 ± 2.7* |
| 100000:1 | 10 | 59.3 ± 3.7 | 0.0001 | 0 | 62.2 ± 15.5 |
| 300000:1 | 30 | *78 ± 7.9 | 0.0001 | 0 | *91.4 ± 2.6 |

*indicates possibly cytotoxicity

These data indicate that some concentrations of CBD and BCP that were ineffective, or minimally effective, on their own resulted in an enhanced reduction of reporter gene expression when used in combination, suggesting that some combinations of CBD and BCP may result in a synergistic anti-inflammatory effect.

Phase 3—Combined Effects of CDB, BCP, and THC:

Based on the data obtained during Phase 2 (shown in Table 2), certain combinations of CBD+BCP will be selected and will be supplemented with various concentrations of THC (e.g. 100, 30, 10, 3, 1, 0.3, 0.1, 0.03, 0.01, 0.003, 0.001, 0.0003, 0.0001, 0.00003 and/or 0.00001 μM THC). The effects of the "triple" CBD+BCP+THC combinations will then be assessed on the RAW-Blue™ cells according to the protocols defined above.

Example 2: Anti-Inflammatory Properties of CBD and BCP on Cytokine Gene Expression Based on the preliminary experiments described in Example 1, particular concentrations and ratios of CBD and BCP were selected for further analysis in gene expression assays for inflammatory cytokines.

Cell Culture and LPS Stimulation:

RAW 264.7 cells were cultured in Dulbecco's Modified Eagle's Medium (high glucose DMEM, Sigma-Aldrich) supplemented with 10% fetal bovine serum (FBS), 1% L-glutamine, 1% Sodium-pyruvate, 1% Penicillin-Streptomycin (culture medium). The cells were maintained in T75 flasks at 37° C. in humidified air containing 5% $CO_2$ in an incubator and passaged every second-third day.

For drug treatment and LPS stimulation, 200,000 cells/well were seeded in 1.5 mL culture medium in a 6-well plate and incubated to allow attachment to the cell culture plate. After attachment, cells were incubated with various concentrations of CBD (0.1 μM, 0.3 μM, 1 μM, 3 μM, 5 μM, 10 μM, and 30 μM) or BCP (0.001 μM, 0.01 μM, 0.013 μM, 0.1 μM, 0.3 μM, 1 μM, 3 μM, 5 μM, 10 μM, and 100 μM), or vehicle (control) for 2 hrs. After the 2 h incubation, 0.1 μg/mL LPS was added to each well to induce inflammation and cells were incubated with LPS for 24 hrs.

Measurement of Anti-Inflammatory Effects of Cannabinoids:

After the 24 h incubation with LPS, the cells were harvested and gene expression of the pro-inflammatory cytokines interleukin (IL)-1α, IL-1β were measured by quantitative real-time polymerase chain reaction (RT-qPCR) on a Roche Light Cycler 480 QPCR System (Roche Applied Sciences) using the 5' nuclease assay. Total RNA was isolated using TRIzol (LifeTechnologies), DNase treatment was performed according to the manufacturer's protocol, and then 1 μg of total RNA was reverse-transcribed into cDNA using High Capacity cDNA Kit from Life Technologies Corporation. PCR amplification was performed using the TaqMan primers and probes (assay IDs: Mm00439620_m1 for murine Il1a; Mm00434228_m1 for murine Il1b, Mm00446190_m1 for murine Il6, Mm00441263_m1 for murine Cxcl15/Il8). Expression of the housekeeping gene, Gapdh, was used (assay ID: Mm999999_g1) as an internal control. The amount of the transcripts was normalized to those of the housekeeping gene using the ΔCT method. Results are expressed as % decrease in the expression levels of IL1α and IL1β in drug-treated, LPS-stimulated groups compared to the expression of each cytokine gene in the vehicle-treated, LPS-stimulated group (regarded as 100%). All experiments were repeated 2-3 times.

For statistical analysis, data were analyzed and graphs were plotted using Origin Pro Plus 6.0 software (Microcal, Northampton, Mass., USA) and Student's two-tailed two samples t-test. $p<0.05$ values were regarded as significant differences.

Cell Viability Assays:

In order to exclude putative cytotoxicity of the phytocannabinoids, cellular viability was also measured throughout the experimental series using a colorimetric MTT. For these assays, cells were plated into 96-well plates at 20,000 cells/well and cultured for 24, 48, or 72 hours in the presence of CBD, BCP, or CBD+BCP. Cells were then incubated with 0.5 mg/mL MTT for 2-3 hours, and the concentration of formazan crystals (as an indicator of number of viable cells) was determined by measuring absorbance levels at $\lambda=550$ nm). If toxic concentrations/combinations of the phytocannabinoids were identified in the MTT assays, those were omitted from further analysis.

Figure 1B:
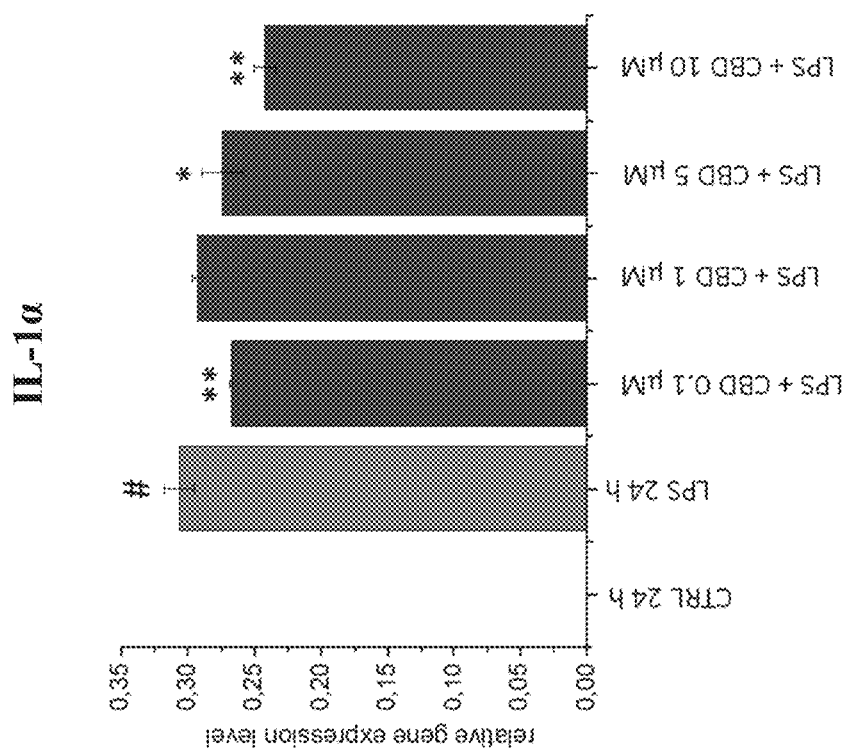
Figures 2A, 2B:
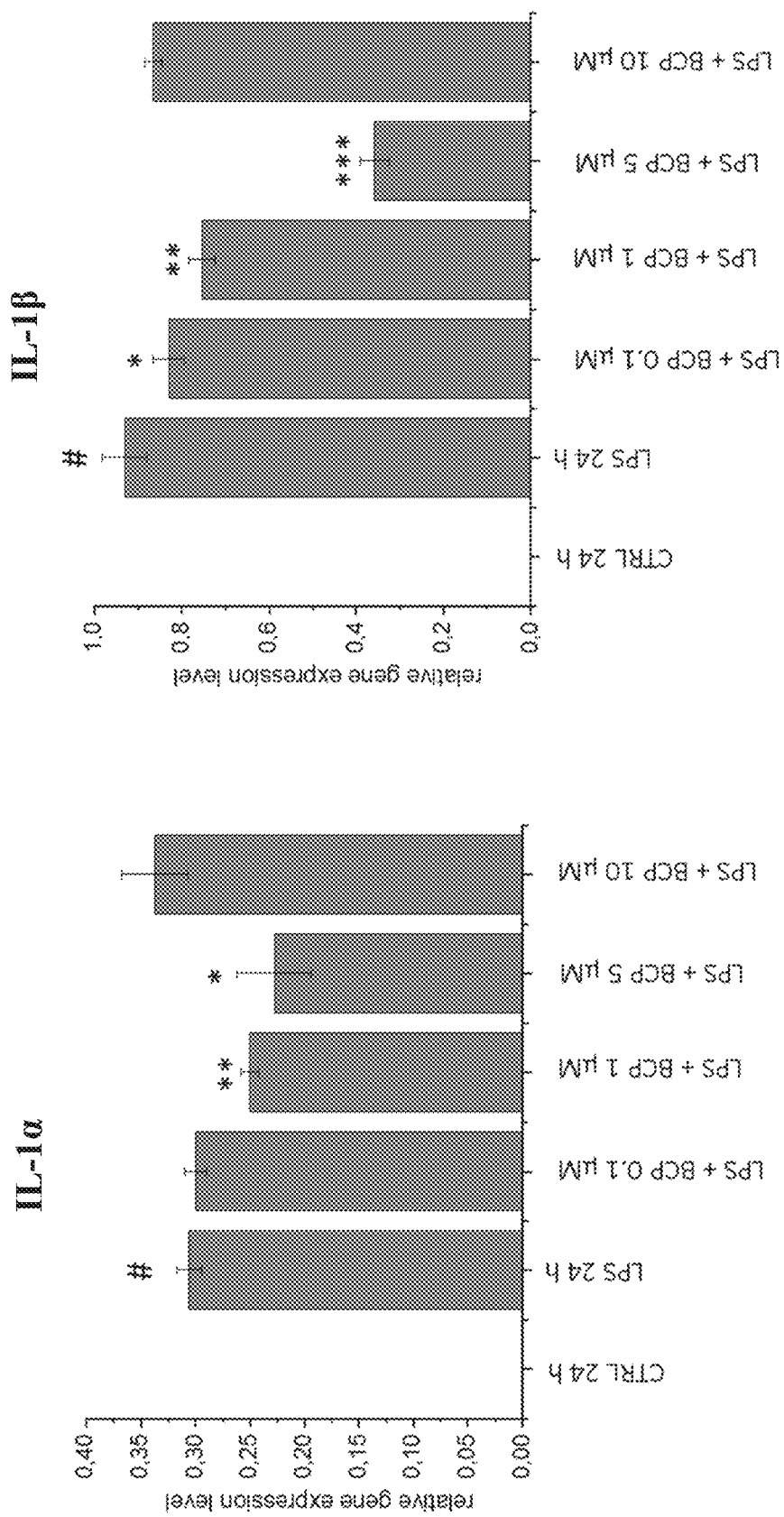
FIG. 2A-FIG. 2B show BCP inhibition of inflammatory cytokine gene expression in LPS-stimulated murine macrophages (RAW 264.7).

Results—Independent Effects of BCP and CBD:

The results from 2 experiments are shown below in Tables 3A and 3B. Table 3A shows the changes in IL-1α and IL-1β expression in CBD- and BCP-treated, LPS-stimulated macrophages compared to untreated, LPS-stimulated controls. Concentrations of CBD used in this experiment were 0.1 μM, 1 μM, 5 μM, or 10 μM and concentrations of BCP used in this experiment were 0.1 μM, 1 μM, 5 μM, or 10 μM. The results of this experiment are also shown graphically in FIGS. 1 and 2. The CBD-mediated inhibition of LPS-stimulated IL-1α and IL-1β expression is shown in FIG. 1A and FIG. 1B, respectively. The BCP-mediated inhibition of LPS-stimulated IL-1α and IL-1β expression is shown in FIG. 2A and FIG. 2B, respectively. In the Figures, # marks comparison of LPS-stimulated groups to the vehicle-treated, unstimulated group (CRTL) and indicate $p<0.05$, whereas *, , and * mark comparison of drug-treated, LPS-stimulated groups to the LPS-stimulated only group and indicate $p<0.05$, $p<0.01$, and $p<0.001$, respectively.

Table 3B shows changes in IL-1α and IL-1β expression in CBD- and BCP-treated, LPS-stimulated macrophages compared to untreated, LPS-stimulated controls. Concentrations of CBD used in this experiment were 10, 3, 1, 0.3, and 0.1 μM and concentrations of BCP used in this experiment were 100, 10, 3, 1, 0.3, 0.1, 0.01, and 0.001 μM.

These data show that CBD, when applied alone, exerted "classical" dose-dependent anti-inflammatory actions; i.e. marked anti-inflammatory effects were observed at concentrations of CBD≥1 μM. Conversely, BCP, when applied alone, exerted only minor (if any) anti-inflammatory actions.

TABLE 3A

Effect of CBD and BCP on IL-1α and IL-1β gene expression

| Concentration | CBD (μM) | | | | BCP (μM) | | | |
|---|---|---|---|---|---|---|---|---|
| | 0.1 | 1 | 5 | 10 | 0.1 | 1 | 5 | 10 |
| IL1α | 13% | 4% | 10% | 21% | 2% | 18% | 26% | 0% |
| Il1β | 19% | 11% | 31% | 33% | 11% | 19% | 62% | 7% |

TABLE 3B

Effect of CBD and BCP on IL-1α and IL-1β gene expression

| | BCP (μM) | | | | | | | |
|---|---|---|---|---|---|---|---|---|
| | 0.001 | 0.01 | 0.1 | 0.3 | 1.0 | 3.0 | 10 | 100 |
| IL1α | 0% | 0% | 1.8 ± 0.2% | 5.8 ± 1.2% | 0% | 0% | 8.2 ± 4.1% | 87 ± 3.2 |
| Il1β | 0% | 0% | 1.8 ± 0.2% | 5.8 ± 1.2% | 0% | 0% | 8.2 ± 4.1% | 94.2 ± 11.3% |

| | CBD (μM) | | | | |
|---|---|---|---|---|---|
| | 0.1 | 0.3 | 1.0 | 3.0 | 10 |
| IL1α | 0% | 3.2 ± 0.2% | 34.5 ± 6.2% | 55.5 ± 4.7% | 82 ± 5.2% |
| Il1β | 5.8 ± 1.4% | 9 ± 3.6% | 39.2 ± 10.1% | 85.6 ± 10% | 92.2 ± 8.4% |

Results—Combined Effects of BCP and CBD:

Additional experiments were performed to determine the effects of CBD and BCP combinations on IL-1α and IL-1β gene expression using particular combinations of CBD and BCP. The CBD concentrations used were 0.1 μM, 0.3 μM, 1.0 μM, 3.0 μM, and 10 μM. The concentrations of BCP used were 0.001 μM, 0.01 μM, 0.1 μM, 0.3 μM, 1.0 μM, 3.0 μM, 10 μM, and 100 μM. Two sets of experiments were performed.

First, experiments were performed with the following combinations of CBD and BCP: 0.1 μM CBD+0.013 μM BCP (representing a CBD:BCP ratio of 7.7:1) and 1 μM CBD+0.13 μM BCP (representing a CBD:BCP ratio of 7.7:1).

The results of this experiment are shown below in Table 4. As shown in Table 4, the combination of 0.1 μM CBD+ 0.013 μM BCP resulted in a greater relative reduction in the LPS-induced gene expression of IL-1α or IL-1β compared to either compound alone. These results are similar to those shown above in Table 2, where 0.1 μM of CBD and 0.013 μM BCP, when used separately, resulted only in a minor or moderate reduction in reporter gene expression (e.g., 0.1 μM CBD=8.5%±1.4 reduction and 0.013 μM BCP=9.2%±3.5 reduction) and resulted in enhanced reduction in reporter gene expression when used in combination (e.g., 0.1 μM CBD+0.013 μM BCP=58.9%±1.2 reduction).

Figure 3B:
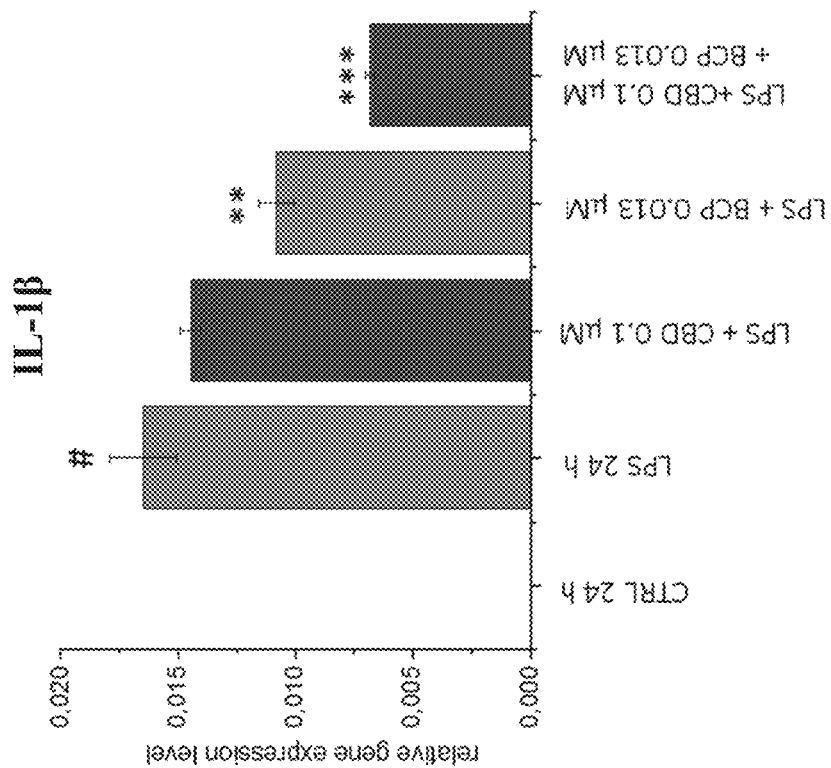
FIG. 3A-FIG. 3B show the effect of CBD+BCP combination on inhibition of inflammatory cytokine gene expression in LPS-stimulated murine macrophages (RAW 264.73).
Figure 3A:
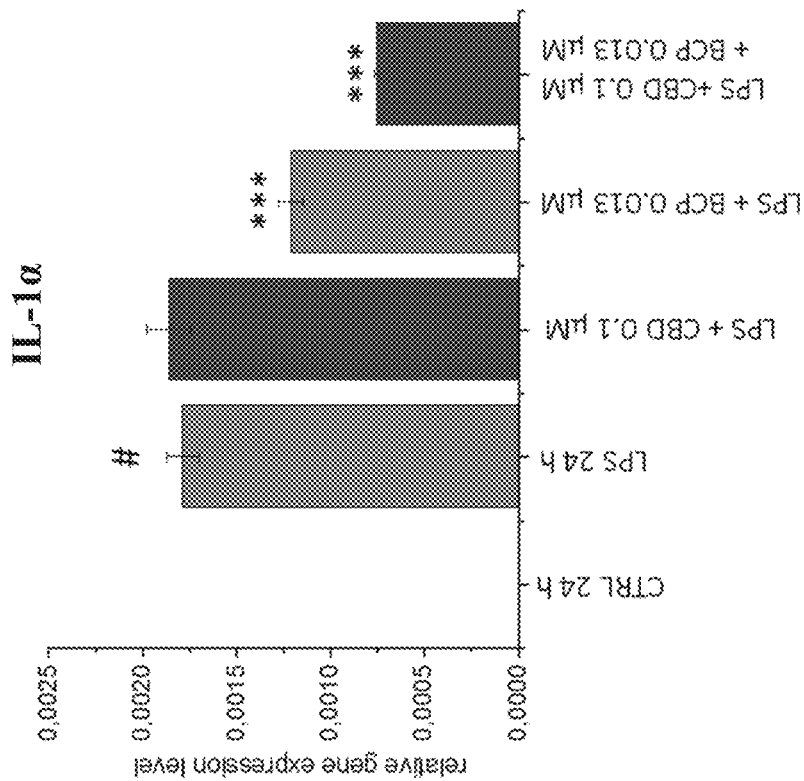

These results are also presented graphically in FIG. 3. As shown in FIG. 3, treatment of macrophages with 0.1 μM of CBD alone did not significantly reduce the LPS-induced expression of IL-1α (FIG. 3A) or IL-1β (FIG. 3B) compared to untreated, LPS-stimulated controls. Treatment of macrophages with 0.013 μM of BCP alone did significantly reduce the LPS-induced expression of both IL-1α (FIG. 3A, * $p<0.001$ compared to LP-stimulated group) and IL-1β (FIG. 3B,  $p<0.01$ compared to LP-stimulated group) compared to untreated, LPS-stimulated controls. However, the combination of 0.1 μM CBD+0.013 μM BCP (representing a CBD:BCP ratio of 7.7:1) resulted in a greater inhibition of both IL-1α (FIG. 3A) and IL-1β (FIG. 3B) gene expression compared to either compound alone (*** $p<0.001$ compared to LP-stimulated group).

Similar results were observed with combinations of 1 μM CBD and 0.13 μM BCP (representing a CBD:BCP ratio of 7.7:1). As shown in Table 4, when applied in combination, 0.1 μM CBD+0.013 μM BCP resulted in a greater relative reduction in the LPS-induced gene expression of IL-1α or IL-1β compared to either compound alone. These results are similar to those shown above in Table 2, where 1 μM of CBD and 0.13 μM BCP, when used separately, resulted only in a minor or moderate reduction in reporter gene expression (e.g., 1 μM CBD=44.6%±5.8 reduction and 0.13 μM BCP=0% reduction) and resulted in enhanced reduction in reporter gene expression when used in combination (e.g., 1 μM CBD+0.13 μM BCP=70.8%±16.2 reduction).

TABLE 4

Effect of CBD and BCP combinations on IL-1α and IL-1β gene expression

| | Exp. 1 | | | Exp. 2 | | |
|---|---|---|---|---|---|---|
| Concentration | CBD 0.1 μM | BCP 0.013 μM | CBD + BCP 0.1 μM + 0.013 μM | CBD 1 μM | BCP 0.13 μM | CBD + BCP 1 μM + 0.13 μM |
| IL-1α | 0% | 32% | 58% | 42% | 0% | 58% |
| IL-1β | 13% | 34% | 59% | 55% | 0% | 64% |

A second set of experiments were performed using the concentration combinations shown below in Table 5. The resulting molar ratios of CBD:BCP are also shown in Table 5.

TABLE 5

Molar Ratios of CBD:BCP

| CBD (μM) | BCP (μM) | | | | | | | |
|---|---|---|---|---|---|---|---|---|
| | 0.001 | 0.01 | 0.1 | 0.3 | 1 | 3 | 10 | 100 |
| 0.1 | 100:1 | 10:1 | 1:1 | 1:3 | 1:10 | 1:30 | 1:100 | 1:1000 |
| 0.3 | 300:1 | 30:1 | 3:1 | 1:1 | 1:3.33 | 1:10 | 1:33.3 | 1:333 |

TABLE 5-continued

| | Molar Ratios of CBD:BCP | | | | | | | |
|---|---|---|---|---|---|---|---|---|
| CBD | BCP (μM) | | | | | | | |
| (μM) | 0.001 | 0.01 | 0.1 | 0.3 | 1 | 3 | 10 | 100 |
| 1 | 1000:1 | 100:1 | 10:1 | 3.33:1 | 1:1 | 1:3 | 1:10 | 1:100 |
| 3 | 3000:1 | 300:1 | 30:1 | 10:1 | 3:1 | 1:1 | 1:3.33 | 1:33.3 |
| 10 | 10000:1 | 1000:1 | 100:1 | 33.3:1 | 10:1 | 10:1 | 1:1 | 1:10 |

The results of this experiment are shown below in Table 6 (IL-1α expression) and Table 7 (IL-1β expression).

TABLE 6

Effect of CBD and BCP combinations on IL-1α gene expression

| Ratio | CBD μM | % Inhibition CBD Alone | BCP μM | % Inhibition BCP Alone | % Inhibition CBD + BCP |
|---|---|---|---|---|---|
| 0:1 | 0 | NA | 0.001 | 0 | NA |
| | 0 | NA | 0.01 | 0 | NA |
| | 0 | NA | 0.1 | 1.8 ± 0.2 | NA |
| | 0 | NA | 0.3 | 5.8 ± 1.2 | NA |
| | 0 | NA | 1 | 0 | NA |
| | 0 | NA | 3 | 0 | NA |
| | 0 | NA | 10 | 8.2 ± 4.1 | NA |
| | 0 | NA | 100 | *87 ± 3.2 | NA |
| 1:1000 | 0.1 | 0 | 100 | *87 ± 3.2 | *93.4 ± 10 |
| 1:333 | 0.3 | 3.2 ± 0.2 | 100 | *87 ± 3.2 | *99 ± 10.2 |
| 1:100 | 0.1 | 0 | 10 | 8.2 ± 4.1 | 13.1 ± 6.3 |
| | 1 | 34.5 ± 6.2 | 100 | *87 ± 3.2 | *94.1 ± 10 |
| 1:33.3 | 0.3 | 3.2 ± 0.2 | 10 | 8.2 ± 4.1 | 43 ± 13.4 |
| | 3 | 55.5 ± 4.7 | 100 | *87 ± 3.2 | *93.2 ± 13.2 |
| 1:30 | 0.1 | 0 | 3 | 0 | 70 ± 12.1 |
| 1:10 | 0.3 | 3.2 ± 0.2 | 3 | 0 | 73.6 ± 14 |
| | 0.1 | 0 | 1 | 0 | 66.9 ± 10 |
| | 1 | 34.5 ± 6.2 | 10 | 8.2 ± 4.1 | 81 ± 11.3 |
| | 10 | 82 ± 5.2 | 100 | *87 ± 3.2 | *96.3 ± 12 |
| 1:3.33 | 0.3 | 3.2 ± 0.2 | 1 | 0 | 50.2 ± 12.3 |
| | 3 | 55.5 ± 4.7 | 10 | 8.2 ± 4.1 | 88.3 ± 12.5 |
| 1:3 | 1 | 34.5 ± 6.2 | 3 | 0 | 77.9 ± 16 |
| | 0.1 | 0 | 0.3 | 5.8 ± 1.2 | 56.9 ± 8.1 |
| 1:1 | 0.1 | 0 | 0.1 | 1.8 ± 0.2 | 49.1 ± 1.6 |
| | 0.3 | 3.2 ± 0.2 | 0.3 | 5.8 ± 1.2 | 76.4 ± 11.8 |
| | 1 | 34.5 ± 6.2 | 1 | 0 | 75.5 ± 16.2 |
| | 3 | 55.5 ± 4.7 | 3 | 0 | 68.5 ± 13 |
| | 10 | 82 ± 5.2 | 10 | 8.2 ± 4.1 | 93.4 ± 11 |
| 3:1 | 0.3 | 3.2 ± 0.2 | 0.1 | 1.8 ± 0.2 | 1.3 ± 0.2 |
| | 3 | 55.5 ± 4.7 | 1 | 0 | 70.8 ± 16 |
| 3.33:1 | 1 | 34.5 ± 6.2 | 0.3 | 5.8 ± 1.2 | 36.2 ± 13 |
| 10:1 | 10 | 82 ± 5.2 | 3 | 0 | 95.6 ± 5.8 |
| | 0.1 | 0 | 0.01 | 0 | 11.2 ± 3 |
| | 1 | 34.5 ± 6.2 | 0.1 | 1.8 ± 0.2 | 43.3 ± 12 |
| | 3 | 55.5 ± 4.7 | 0.3 | 5.8 ± 1.2 | 61.8 ± 13.5 |
| | 10 | 82 ± 5.2 | 1 | 0 | 98.6 ± 14 |
| 30:1 | 0.3 | 3.2 ± 0.2 | 0.01 | 0 | 2.8 ± 0.1 |
| | 3 | 55.5 ± 4.7 | 0.1 | 1.8 ± 0.2 | 52 ± 13.2 |
| 33.3:1 | 10 | 82 ± 5.2 | 0.3 | 5.8 ± 1.2 | 93.3 ± 11.4 |
| 100:1 | 0.1 | 0 | 0.001 | 0 | 51.2 ± 7.4 |
| | 1 | 34.5 ± 6.2 | 0.01 | 0 | 40 ± 11.2 |
| | 10 | 82 ± 5.2 | 0.1 | 1.8 ± 0.2 | 92.8 ± 13 |
| 300:1 | 0.3 | 3.2 ± 0.2 | 0.001 | 0 | 88.1 ± 9.2 |
| | 3 | 55.5 ± 4.7 | 0.01 | 0 | 66.8 ± 16.2 |
| 1000:1 | 1 | 34.5 ± 6.2 | 0.001 | 0 | 35.5 ± 11 |
| | 10 | 82 ± 5.2 | 0.01 | 0 | 88.1 ± 14.2 |
| 3000:1 | 3 | 55.5 ± 47 | 0.001 | 0 | 42.9 ± 14.9 |
| 10000:1 | 10 | 82 ± 5.2 | 0.001 | 0 | 79.2 ± 15.2 |
| 1:0 | 0 | NA | 0 | NA | NA |
| | 0.1 | 0 | 0 | NA | NA |
| | 0.3 | 3.2 ± 0.2 | 0 | NA | NA |
| | 1 | 34.5 ± 6.2 | 0 | NA | NA |
| | 3 | 55.5 ± 4.7 | 0 | NA | NA |
| | 10 | 82 ± 5.2 | 0 | NA | NA |

*indicates possibly cytotoxicity

TABLE 7

Effect of CBD and BCP combinations on IL-1β gene expression

| Ratio | CBD μM | % Inhibition CBD Alone | BCP μM | % Inhibition BCP Alone | % Inhibition CBD + BCP |
|---|---|---|---|---|---|
| 0:1 | 0 | NA | 0.001 | 0 | NA |
| | 0 | NA | 0.01 | 0 | NA |
| | 0 | NA | 0.1 | 1.8 ± 0.2 | NA |
| | 0 | NA | 0.3 | 5.8 ± 1.2 | NA |
| | 0 | NA | 1 | 0 | NA |
| | 0 | NA | 3 | 0 | NA |
| | 0 | NA | 10 | 8.2 ± 4.1 | NA |
| | 0 | NA | 100 | *94.2 ± 11.3 | NA |
| 1:1000 | 0.1 | 5.8 ± 1.4 | 100 | *94.2 ± 11.3 | *90 ± 15.3 |
| 1:333 | 0.3 | 9 ± 3.6 | 100 | *94.2 ± 11.3 | *89.1 ± 6.1 |
| 1:100 | 0.1 | 5.8 ± 1.4 | 10 | 8.2 ± 4.1 | 33.2 ± 8.2 |
| | 1 | 39.2 ± 10.1 | 100 | *94.2 ± 11.3 | *90.1 ± 14 |
| 1:33.3 | 0.3 | 9 ± 3.6 | 10 | 8.2 ± 4.1 | 58.4 ± 8.4 |
| | 3 | 85.6 ± 10 | 100 | *94.2 ± 11.3 | *90.9 ± 6 |
| 1:30 | 0.1 | 5.8 ± 1.4 | 3 | 0 | 43 ± 4.8 |
| 1:10 | 0.3 | 9 ± 3.6 | 3 | 0 | 83.2 ± 18.2 |
| | 0.1 | 5.8 ± 1.4 | 1 | 0 | 52.1 ± 6.6 |

TABLE 7-continued

Effect of CBD and BCP combinations on IL-1β gene expression

| Ratio | CBD μM | % Inhibition CBD Alone | BCP μM | % Inhibition BCP Alone | % Inhibition CBD + BCP |
|---|---|---|---|---|---|
| | 1 | 39.2 ± 10.1 | 10 | 8.2 ± 4.1 | 60.2 ± 10.4 |
| | 10 | 92.2 ± 8.4 | 100 | *94.2 ± 11.3 | *99 ± 3.9 |
| 1:3.33 | 0.3 | 9 ± 3.6 | 1 | 0 | 55 ± 10 |
| | 3 | 85.6 ± 10 | 10 | 8.2 ± 4.1 | 93.8 ± 10.5 |
| 1:3 | 1 | 39.2 ± 10.1 | 3 | 0 | 67.3 ± 20.1 |
| | 0.1 | 5.8 ± 1.4 | 0.3 | 5.8 ± 1.2 | 66 ± 11 |
| 1:1 | 0.1 | 5.8 ± 1.4 | 0.1 | 1.8 ± 0.2 | 39.9 ± 5 |
| | 0.3 | 9 ± 3.6 | 0.3 | 5.8 ± 1.2 | 78.2 ± 12 |
| | 1 | 39.2 ± 10.1 | 1 | 0 | 69.4 ± 13.1 |
| | 3 | 85.6 ± 10 | 3 | 0 | 98.4 ± 12.2 |
| | 10 | 92.2 ± 8.4 | 10 | 8.2 ± 4.1 | 93.9 ± 15 |
| 3:1 | 0.3 | 9 ± 3.6 | 0.1 | 1.8 ± 0.2 | 38.1 ± 5.6 |
| | 3 | 85.6 ± 10 | 1 | 0 | 82.5 ± 13.2 |
| 3.33:1 | 1 | 39.2 ± 10.1 | 0.3 | 5.8 ± 1.2 | 56 ± 8.2 |
| 10:1 | 10 | 92.2 ± 8.4 | 3 | 0 | 85.9 ± 15.6 |
| | 0.1 | 5.8 ± 1.4 | 0.01 | 0 | 6.5 ± 1.1 |
| | 1 | 39.2 ± 10.1 | 0.1 | 1.8 ± 0.2 | 40.1 ± 5.5 |
| | 3 | 85.6 ± 10 | 0.3 | 5.8 ± 1.2 | 91.1 ± 16 |
| | 10 | 92.2 ± 8.4 | 1 | 0 | 88.8 ± 10.2 |
| 30:1 | 0.3 | 9 ± 3.6 | 0.01 | 0 | 18.3 ± 3.8 |
| | 3 | 85.6 ± 10 | 0.1 | 1.8 ± 0.2 | 82.2 ± 10.2 |
| 33.3:1 | 10 | 92.2 ± 8.4 | 0.3 | 5.8 ± 1.2 | 98 ± 14.7 |
| 100:1 | 0.1 | 5.8 ± 1.4 | 0.001 | 0 | 31.4 ± 3.5 |
| | 1 | 39.2 ± 10.1 | 0.01 | 0 | 56.4 ± 8.4 |
| | 10 | 92.2 ± 8.4 | 0.1 | 1.8 ± 0.2 | 93.6 ± 15.1 |
| 300:1 | 0.3 | 9 ± 3.6 | 0.001 | 0 | 34.4 ± 4.2 |
| | 3 | 85.6 ± 10 | 0.01 | 0 | 86 ± 14.1 |
| 1000:1 | 1 | 39.2 ± 10.1 | 0.001 | 0 | 42.3 ± 8.1 |
| | 10 | 92.2 ± 8.4 | 0.01 | 0 | 86.8 ± 15.8 |
| 3000:1 | 3 | 85.6 ± 10 | 0.001 | 0 | 91 ± 10.2 |
| 10000:1 | 10 | 92.2 ± 8.4 | 0.001 | 0 | 89.5 ± 13 |
| 1:0 | 0 | N/A | 0 | NA | NA |
| | 0.1 | 5.8 ± 1.4 | 0 | NA | NA |
| | 0.3 | 9 ± 3.6 | 0 | NA | NA |
| | 1 | 39.2 ± 10.1 | 0 | NA | NA |
| | 3 | 85.6 ± 10 | 0 | NA | NA |
| | 10 | 92.2 ± 8.4 | 0 | NA | NA |

*indicates possibly cytotoxicity

These data indicate that some concentrations of CBD and BCP that were ineffective, or minimally effective, on their own resulted in an enhanced reduction of IL-1α and/or IL-1β gene expression when used in combination, suggesting that some combinations of CBD and BCP may result in a synergistic anti-inflammatory effect.

Example 3: In Vivo Model of Carrageenan-Induced Inflammation

Studies were performed to assess the in vivo efficacy of CBD and BCP, alone and in combination, on multiple read-outs of carrageenan-induced inflammation.

Solution Preparation and Administration:

CBD and BCP solutions (≥80%, FCC, FG) were dissolved in a solution containing 10% Tween 80 and 90% saline (vehicle) and were freshly prepared immediately before use. Mice were treated with drug solutions or vehicle control by intraperitoneal (i.p.) injection at a volume of 0.1 mL/10 g body weight. Acute paw injury was induced by intraplantar injection of 20 μL 3% carrageenan (dissolved in 0.9% NaCl, Sigma Aldrich, St. Louis, Mo., USA) into the right hind paw.

Figure 17:
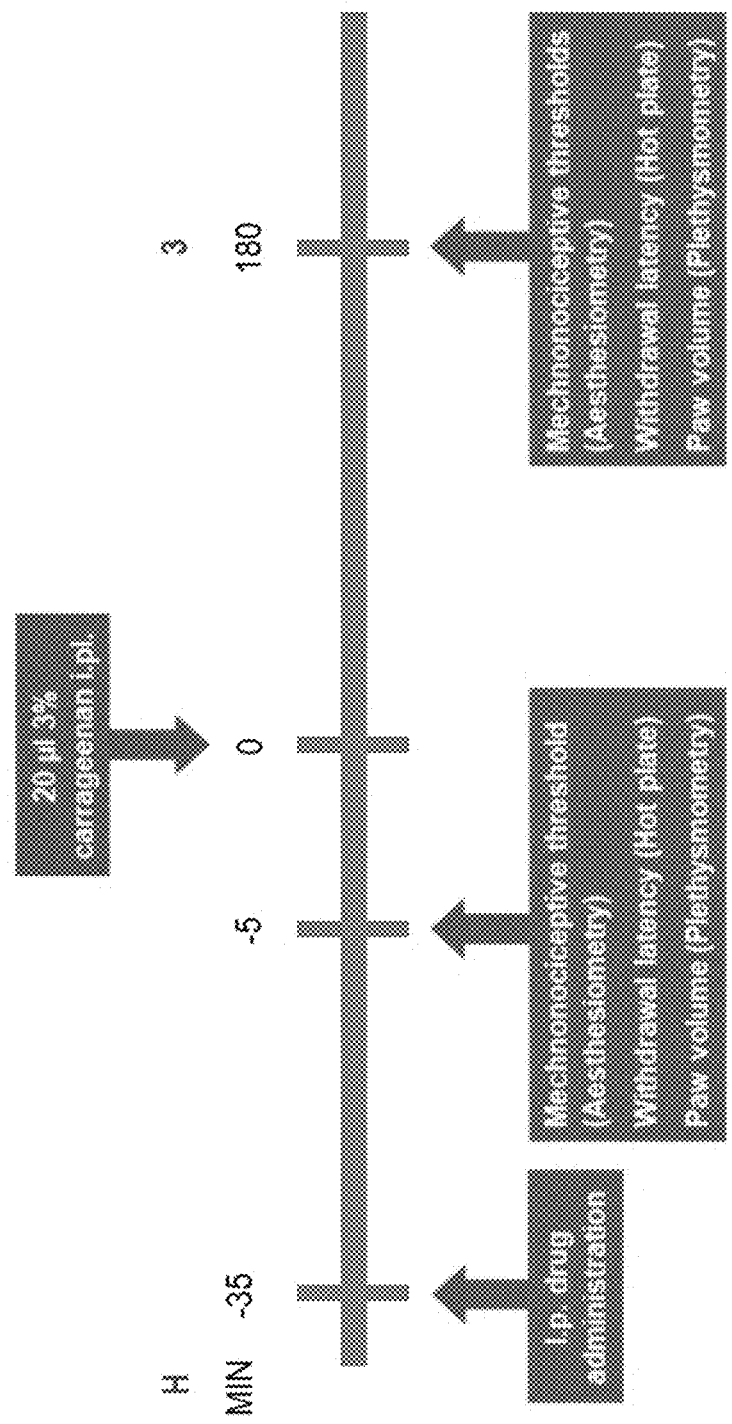
FIG. 17 shows a schematic of the carrageenan-induced inflammation protocol.

Treatment Protocol:

Experiments were performed on 7-16-week-old male NMRI mice (30-50 g) provided with standard chow and water ad libitum. Mice were divided into groups and treated with a single dose of vehicle control (VEH), CBD, BCP, or CBD+BCP delivered i.p. 30 minutes after drug administration, measurements were taken to determine baseline values for mechanonociceptive thresholds and paw volumes. 35 minutes after drug administration, 20 μL of 3% carrageenan was injected intraplantarly (i.pl.) in the right hind paws. 3 hours after carrageenan administration, additional measurements were taken to determine the mechanonociceptive thresholds and paw volumes of the ipsilateral and contralateral paws. A schematic of the treatment protocol is shown in FIG. 17.

Plethysmometry Measurements:

Baseline and post-carrageenan injection paw volume was determined by plethysmometry (Ugo Basile Plethysmometer 7140, Comerio, Italy) and expressed in cubic centimeter ($cm^3$). Paw edema was presented as percentage increase of baseline values obtained prior to carrageenan administration (Bolcskei K. et al., Pain. 2005; 117:368-76).

Mechanonociceptive Threshold Measurements:

The mechanonociceptive threshold of the hind paws were measured by dynamic plantar aesthesiometry (DPA, Ugo Basile 37400, Comerio, Italy). Mice were placed into plexiglass boxes with a wire grid floor. After acclimation, the plantar surface was touched with a straight metal filament, lifting with increasing upward force (until the animal withdrew his paw or until the maximum force of 10 g was reached (maximum force of 10 g reached within 4 s). Mechanonociceptive thresholds are expressed in gram (g), while mechanical hyperalgesia is represented as a percentage decrease from the initial withdrawal thresholds (i.e., before drug and carrageenan administration) (Bolcskei K. et al., Pain. 2005; 117:368-76).

Example 4: Anti-Inflammatory Effects of CBD and BCP In Vivo

To assess the effects of CBD and BCP treatment, mice were divided into groups and treated according to the protocol described in Example 3. Four dosing concentrations of CBD (0.5 mg/kg, 1 mg/kg, 10 mg/kg, and 30 mg/kg) and four dosing concentrations of BCP (1 mg/kg, 5 mg/kg, 10 mg/kg, and 30 mg/kg) were used in these experiments.

Figure 4B:
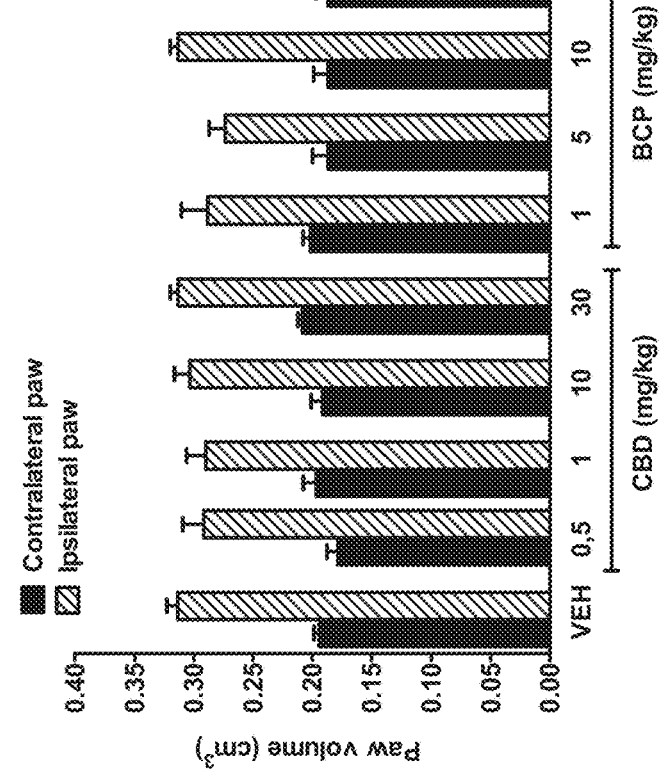
FIG. 4A-FIG. 4B show the effects of CBD and BCP on paw edema induced by an inflammatory stimuli.
Figure 4A:
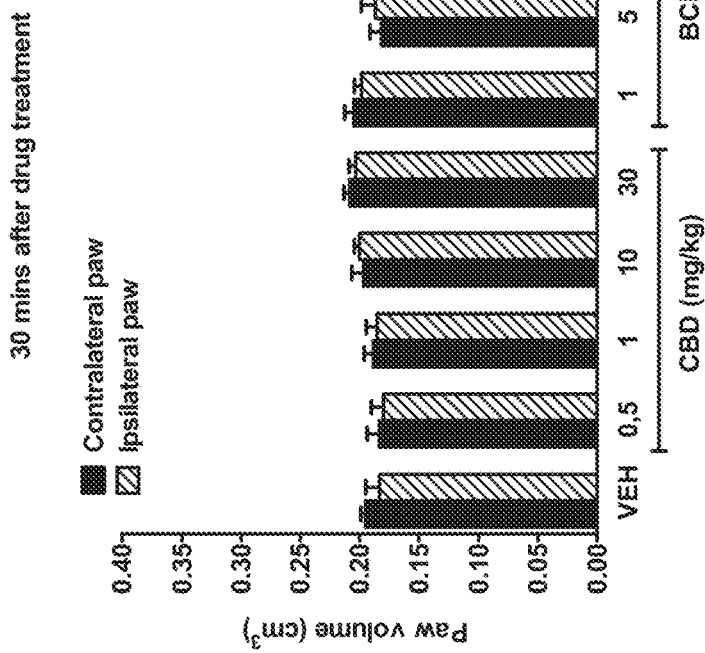
Figure 5B:
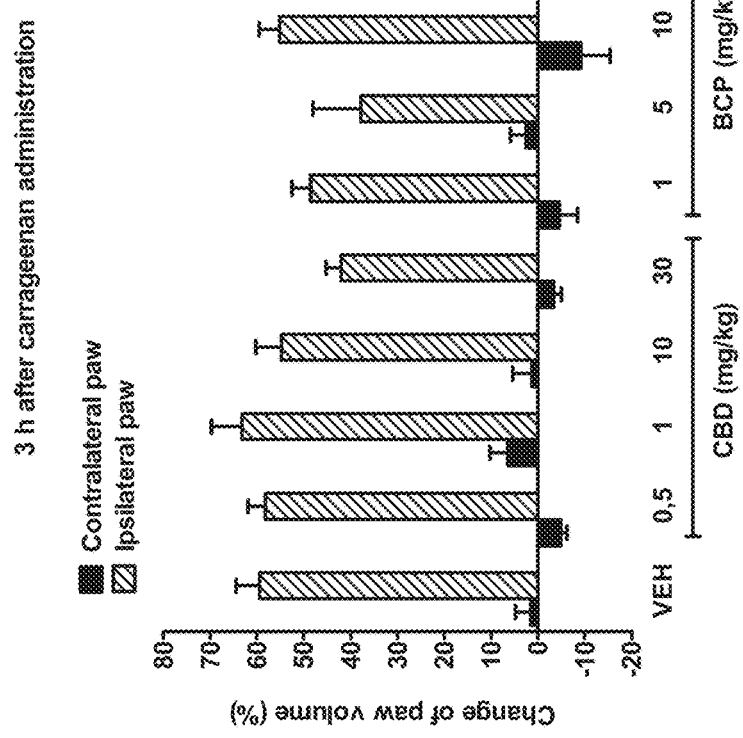
FIG. 5A-FIG. 5B shows the data illustrated in FIG. 4 represented as a change in paw volume compared to vehicle-treated controls.
Figure 5A:
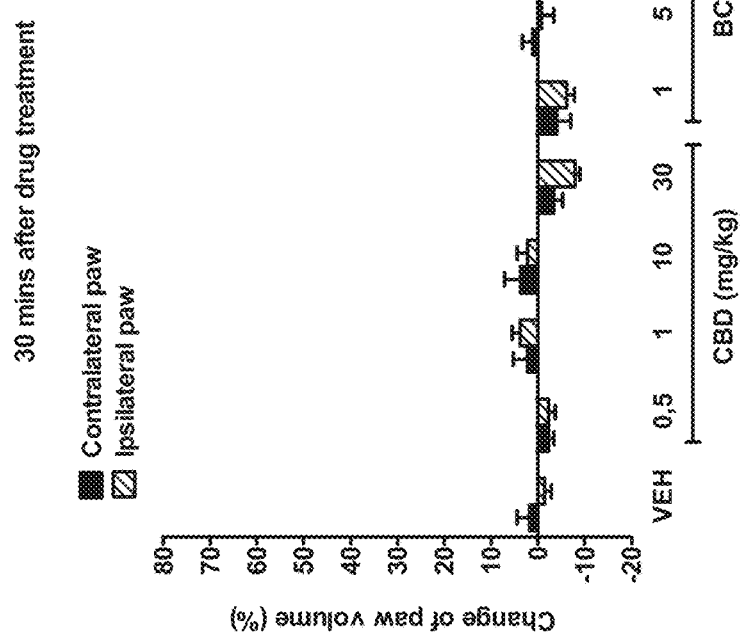

Plethysmometry:

Plethysmometry measurements were taken as described in Example 4. As shown in FIG. 4A and FIG. 5A, none of the investigated single doses of CBD or BCP influenced the basal paw volume of hind paw volume as compared to the vehicle-treated mice 30 min after administration of the given drug. Three hours after i.pl. carrageenan administration, a 60% increase of the paw volume developed in vehicle-treated group (FIG. 5B), and was only mildly influenced by most CBD and BCP single dose pre-treatments (FIG. 4B and FIG. 5B). However, 30 mg/kg BCP markedly reduced the carrageenan-induced paw edema to 20%, as compared to the vehicle-treated controls (FIG. 4B and FIG. 5B, $p<0.0001$).

Figures 6A, 6B:
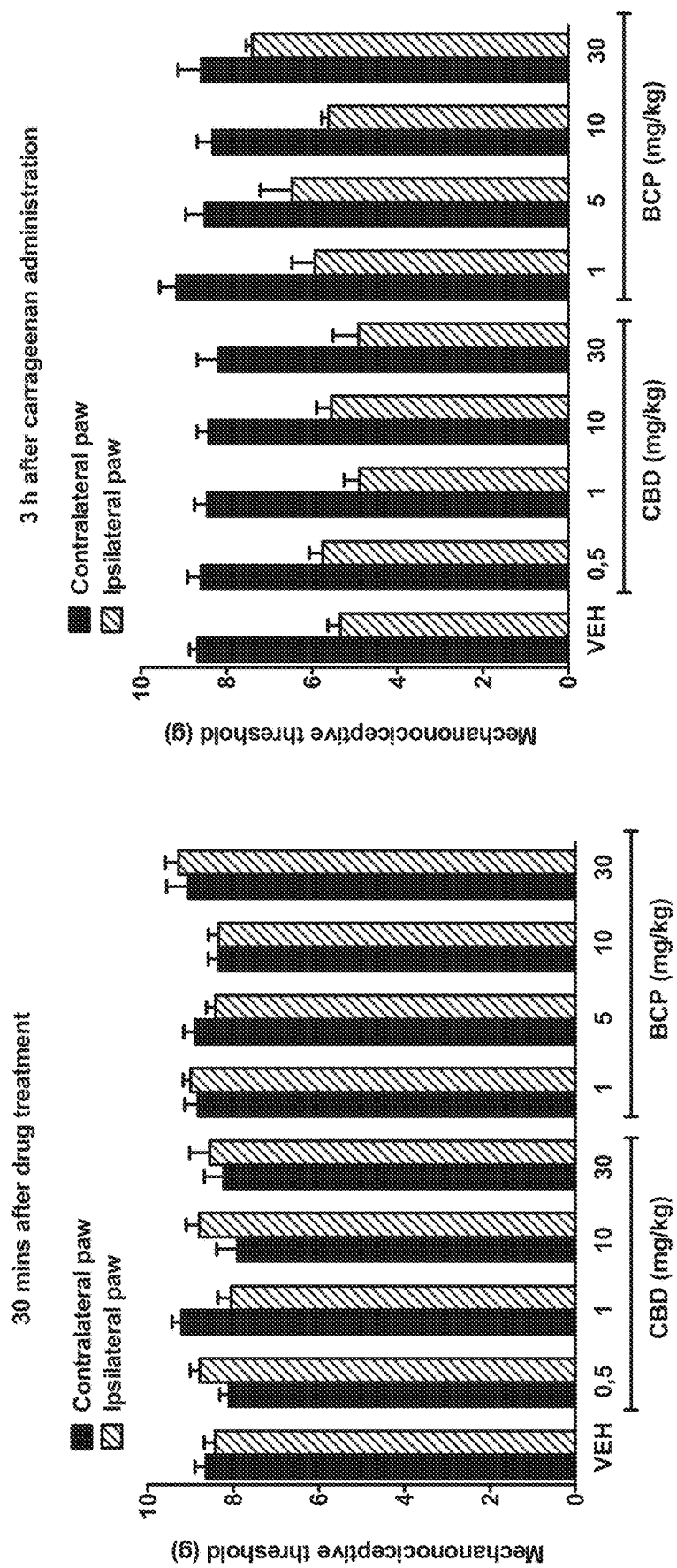
FIG. 6A-FIG. 6B show the effects of CBD and BCP treatment on mechanonociceptive thresholds.
Figure 7B:
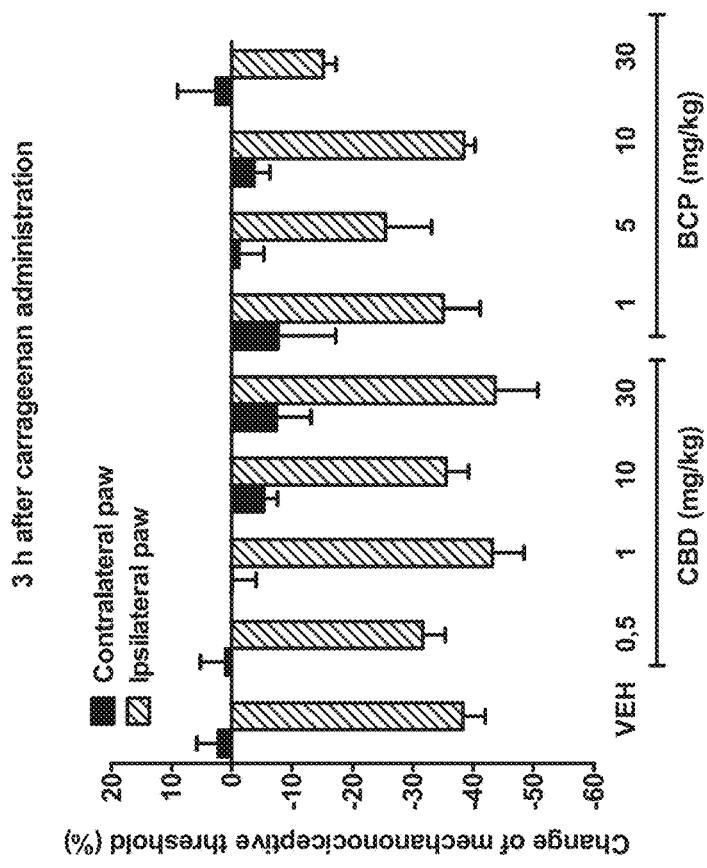
FIG. 7A-FIG. 7B show the data illustrated in FIG. 6 represented as a change in mechanonociceptive threshold as compared to vehicle-treated controls.
Figure 7A:
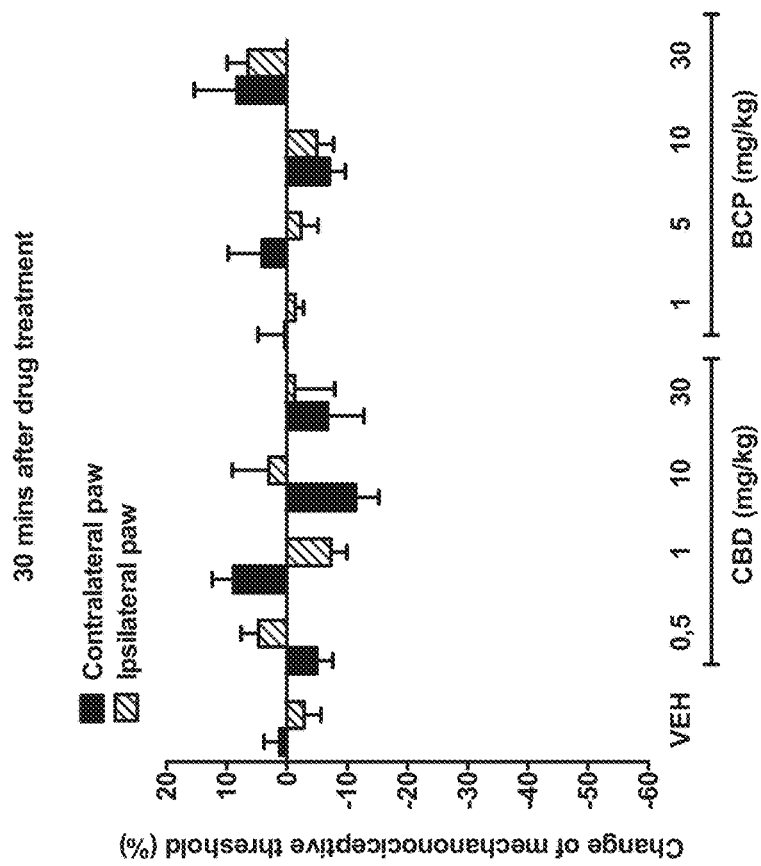

Mechanonociceptive Threshold:

Mechanonociceptive threshold measurements were taken as described in Example 3. As shown in FIG. 6A, none of the investigated single doses of CBD and BCP influenced the basal mechanonociceptive threshold of the hind paws as compared to the vehicle-treated mice 30 min after drug administration. Three hours after i.pl. carrageenan administration, a 40% decrease of the mechanonociceptive threshold (mechanical hyperalgesia) developed in the vehicle-treated group (FIG. 6B and FIG. 7B). This suppression of the mechanonociceptive threshold was only mildly influenced (i.e. reversed) by most CBD and BCP single pre-treatments (FIG. 6B and FIG. 7B). However, 30 mg/kg BCP significantly reduced the carrageenan-induced mechanical hyperalgesia as compared to the vehicle (FIG. 7B, $p<0.001$).

Example 5: Effects of CBD+BCP Combination Treatment In Vivo

To assess the effect of CBD+BCP combination treatment, mice were divided into groups and treated according to the protocol described in Example 3. Two groups of experiments were performed with the concentrations of CBD and BCP, and the respective CBD:BCP ratios, indicated in Table 8 below. In each group of experiments, plethysmometry, and mechanonociceptive threshold measurements were taken as described in Example 3.

TABLE 8

| In vivo CDB and BCP doses and ratios | | | |
|---|---|---|---|
| Exp. Group | CBD (mg/kg) | BCP (mg/kg) | CBD:BCP mass ratio |
| 1 | 1.0 | 0.0 | 1:0 |
|  | 1.0 | 1.0 | 1:1 |
|  | 1.0 | 5.0 | 1:5 |
|  | 1.0 | 10.0 | 1:10 |
|  | 1.0 | 30.0 | 1:30 |

TABLE 8-continued

| In vivo CDB and BCP doses and ratios | | | |
|---|---|---|---|
| Exp. Group | CBD (mg/kg) | BCP (mg/kg) | CBD:BCP mass ratio |
| 2 | 0.5 | 0.0 | 1:0 |
|  | 0.5 | 0.05 | 10:1 |
|  | 0.5 | 5.0 | 1:10 |
|  | 0.5 | 10.0 | 1:20 |

Group 1 Experiments: 1 mg/kg CBD

Figure 8B:
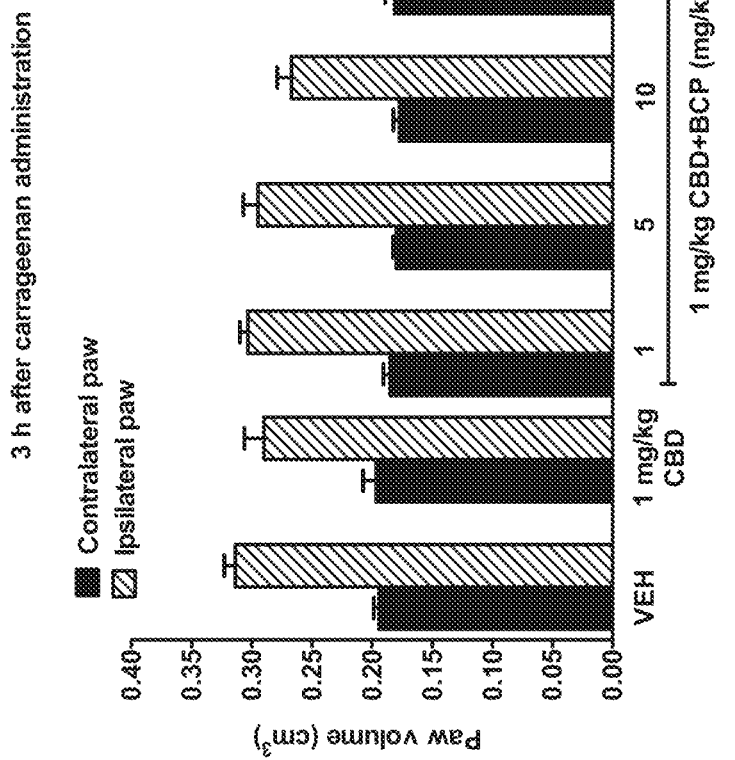
FIG. 8A-FIG. 8B shows the effects of CBD+BCP combination treatment on paw edema induced by an inflammatory stimuli.
Figure 8A:
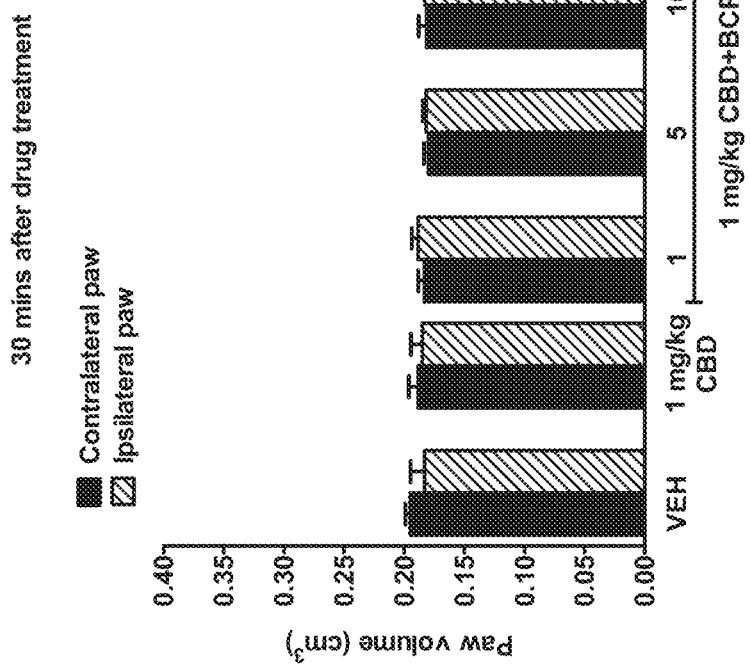
Figure 9A:
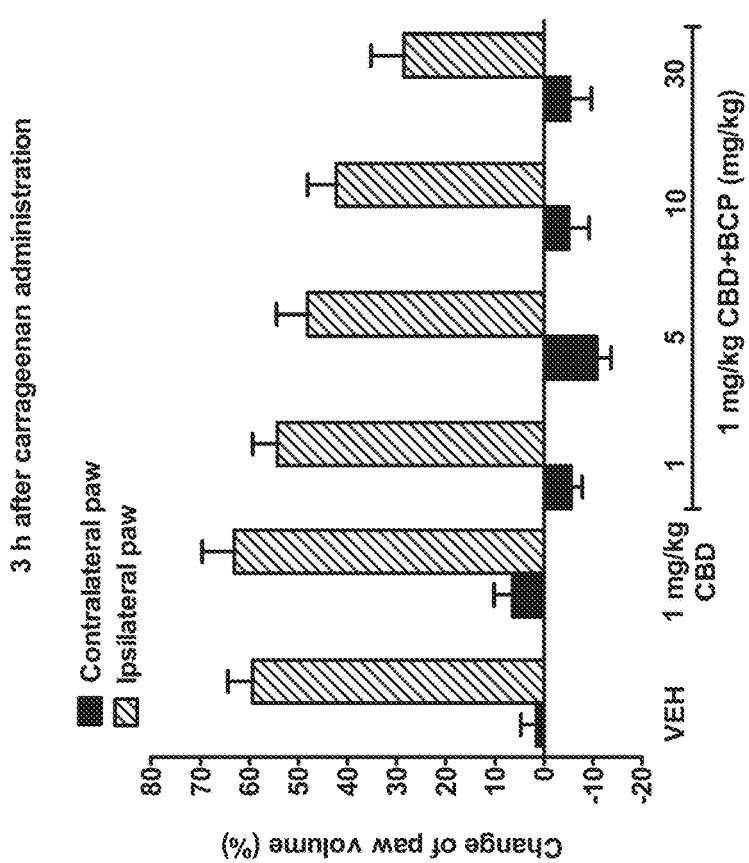
FIG. 9A-FIG. 9B show the data illustrated in FIG. 8 represented as a change in paw volume from a baseline measurement.
Figure 9B:
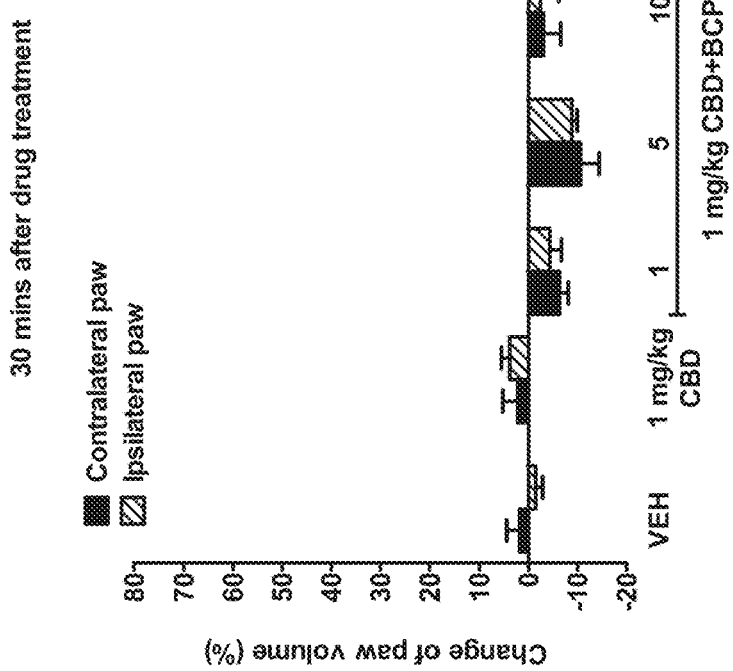

Plethysmometry:

As shown in FIGS. 8A and 9A, none of the investigated combinations of 1 mg/kg CBD and BCP (1, 5, 10 or 30 mg/kg) influenced the basal hind paw volume as compared to the vehicle- and 1 mg/kg CBD-treated mice 30 min after drug administration (FIG. 8A and FIG. 9A). 3 hours after i.pl. carrageenan administration a ca. 60% increase of the paw volume developed in the vehicle-treated group which was not influenced by the administration of 1 mg/kg CBD (FIG. 8B and FIG. 9B). However, co-administration of increasing doses of BCP with the 1 mg/kg CBD improved edema formation in a dose-dependent manner. Furthermore, the 1 mg/kg CBD+10 mg/kg BCP and the 1 mg/kg CBD+30 mg/kg BCP combinations markedly reduced the carrageenan-induced paw edema to 40% and 30%, respectively, as compared to the vehicle or 1 mg/kg CBD-treated group (FIG. 8B and FIG. 9B). The effects of the CBD+BCP combinations were more robust than 1 mg/kg CBD or 1, 5, or 10 mg/kg BCP alone.

Figure 10B:
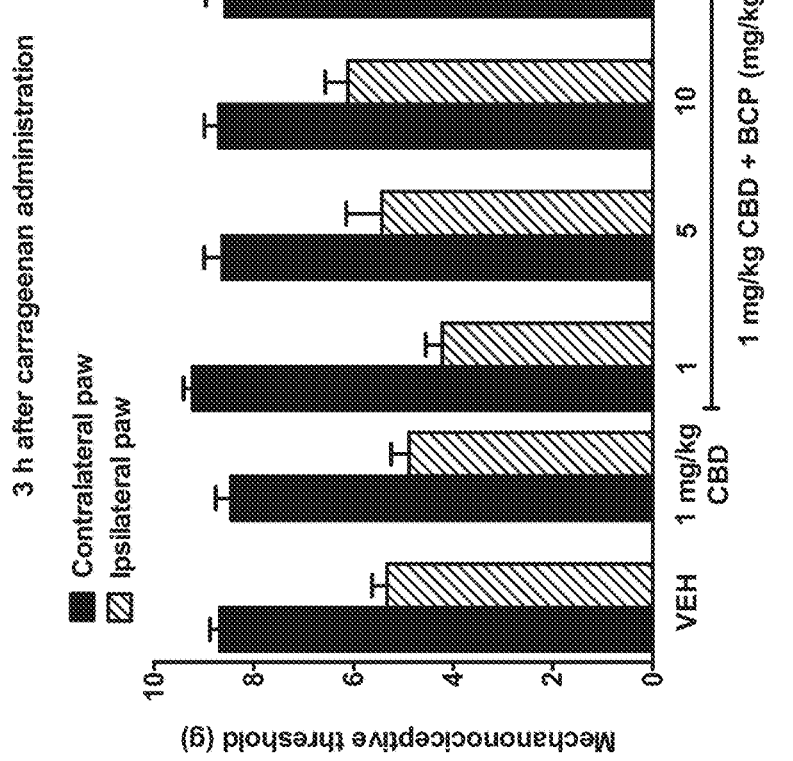
FIG. 10A-FIG. 10B show the effects of CBD+BCP treatment on mechanonociceptive thresholds.
Figure 10A:
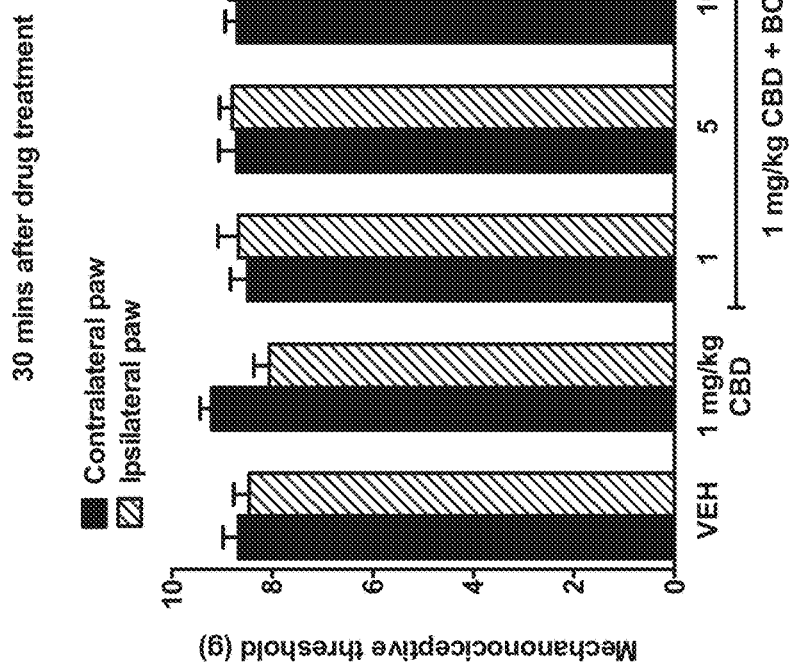
Figure 11B:
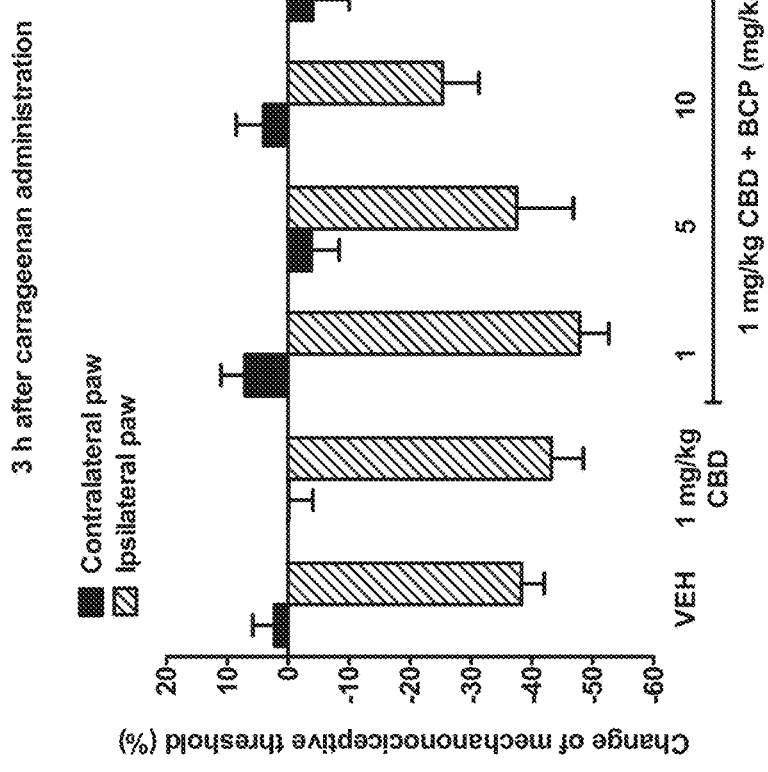
FIG. 11A-FIG. 11B show the data illustrated in FIG. 10 represented as a change in mechanonociceptive threshold as compared to vehicle-treated controls.
Figure 11A:
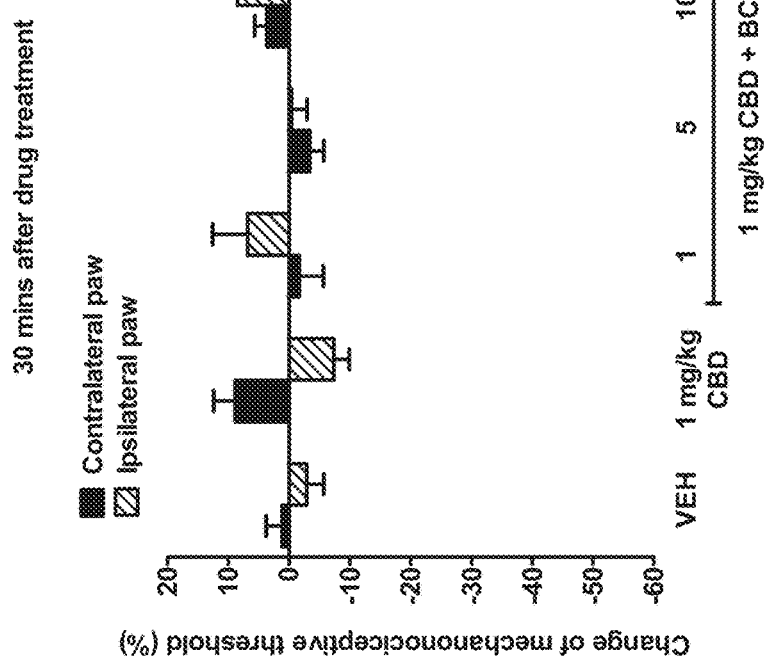

Mechanonociceptive Threshold:

As shown in FIGS. 10A and 11A, none of the investigated combinations of 1 mg/kg CBD+BCP (1, 5, 10 or 30 mg/kg) influenced the basal mechanonociceptive threshold of the hind paws as compared to the vehicle-treated mice 30 min after drug administration. 3 hours after i.pl. carrageenan administration a ca. 40% drop of the mechanonociceptive threshold developed in the vehicle-treated group which was not influenced by the administration of 1 mg/kg CBD (FIGS. 10B and 11B). Of the different CBD+BCP combinations, 1 mg/kg CBD+1 mg/kg BCP and 1 mg/kg CBD+5 mg/kg BCP did not modify the reduced mechanonociceptive threshold (FIGS. 10B and 11B). Notably, the effects of the 1 mg/kg CBD+10 mg/kg BCP and 1 mg/kg CBD+30 mg/kg combinations were much more robust than the negligible effects of 1 mg/kg CBD or 10 mg/kg BCP when applied alone (FIGS. 10B and 11B).

Group 2 Experiments: 0.5 mg/kg CBD

Figure 12B:
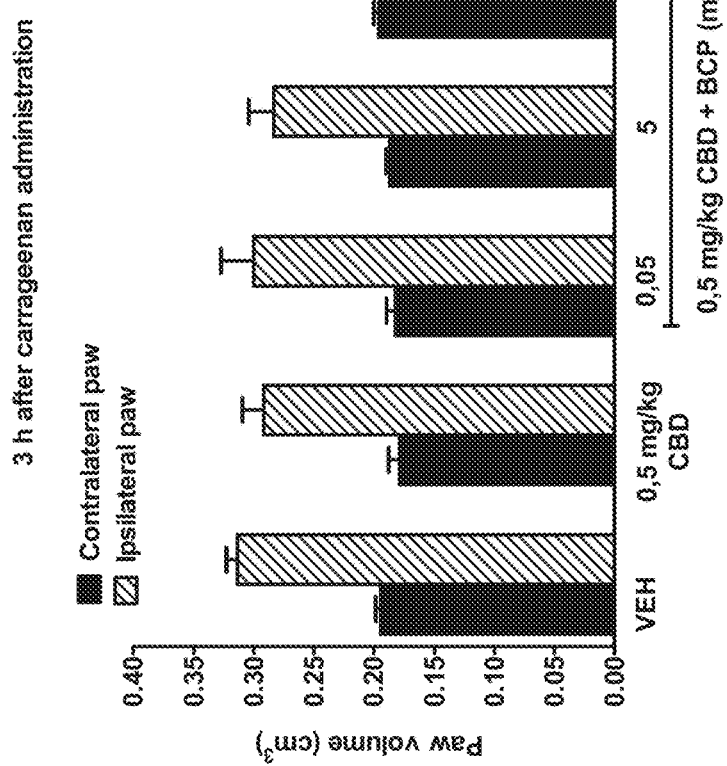
FIG. 12A-FIG. 12B show the results of an additional experiment demonstrating the effects of CBD+BCP combination on paw edema induced by an inflammatory stimuli.
Figure 12A:
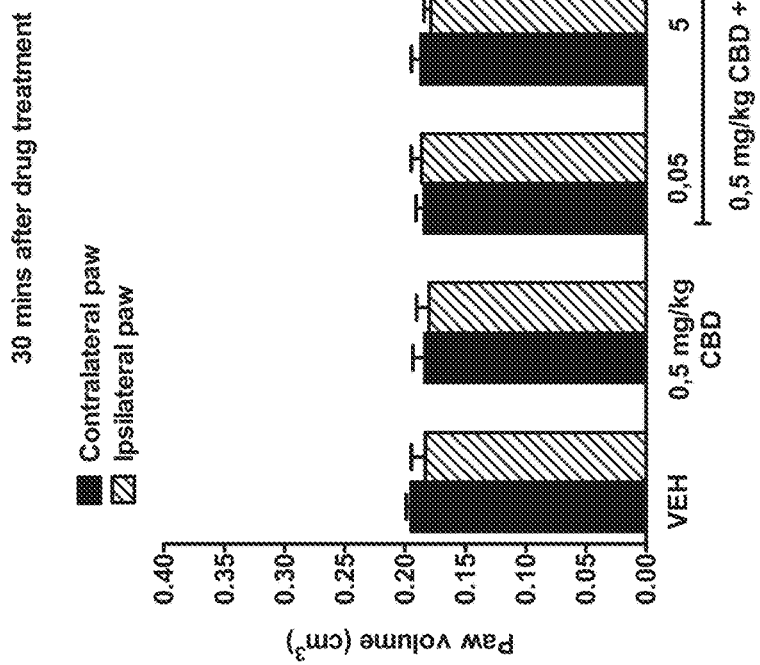
Figure 13B:
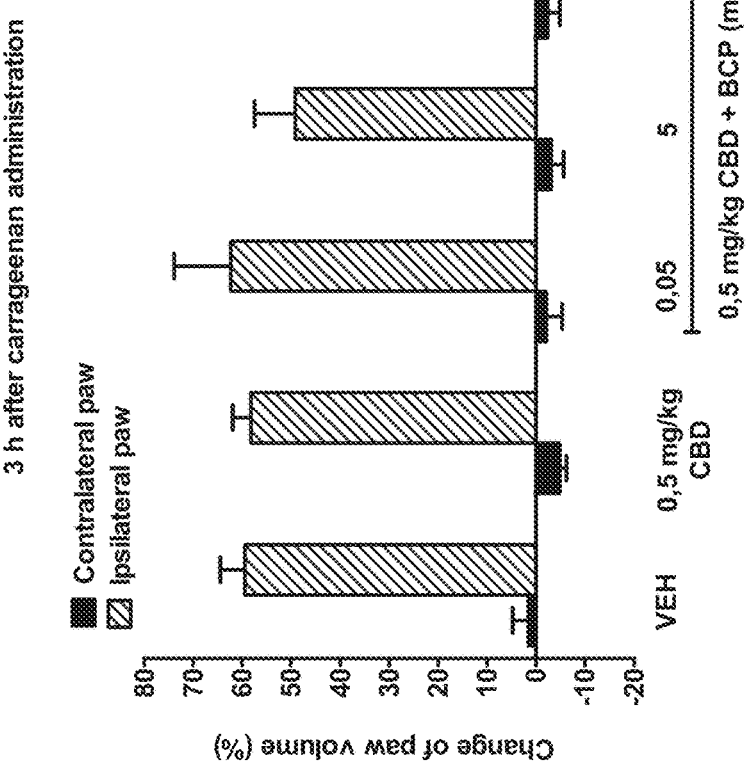
FIG. 13A-FIG. 13B show the data illustrated in FIG. 12 represented as a change in paw volume compared to vehicle-treated controls.
Figure 13A:
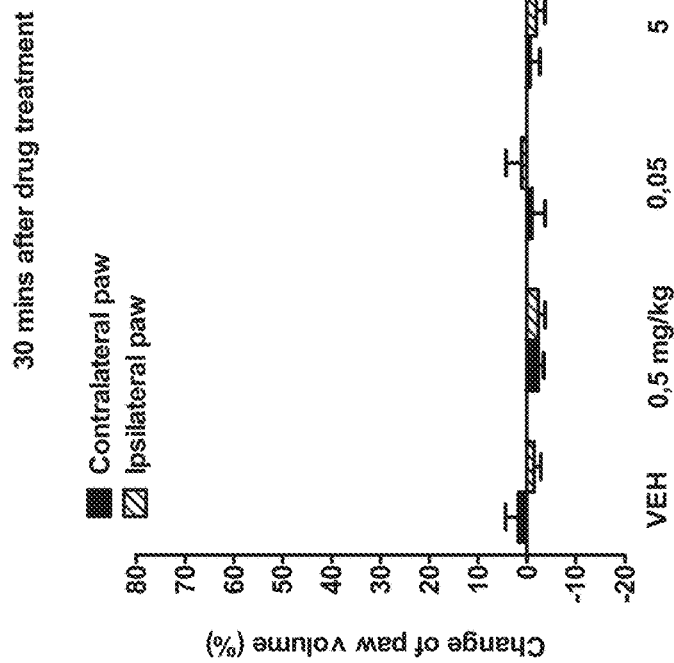

Plethysmometry:

As shown in FIG. 12A and FIG. 13A, none of the investigated combinations of 0.5 mg/kg CBD and BCP (0.05, 5, 10) influenced the basal hind paw volume as compared to the vehicle- and the 0.5 mg/kg CBD-treated mice 30 min after drug treatment. 3 hours after i.pl. carrageenan administration a ca. 60% increase of the paw volume developed in the vehicle-treated group which was not influenced by the administration of 0.5 mg/kg CBD (FIG. 12B and FIG. 13B). Although to lesser degree than observed in CBD+BCP combinations with 1 mg/kg CBD, co-administration of increasing doses BCP with 0.5 mg/kg CBD improved edema formation in a dose-dependent manner (FIG. 12B and FIG. 13B). Notably, the effects of the combined applications were more robust than the single applications of 0.5 mg/kg CBD or 0.05, 5, or 10 mg/kg BCP when applied alone.

Figure 14A:
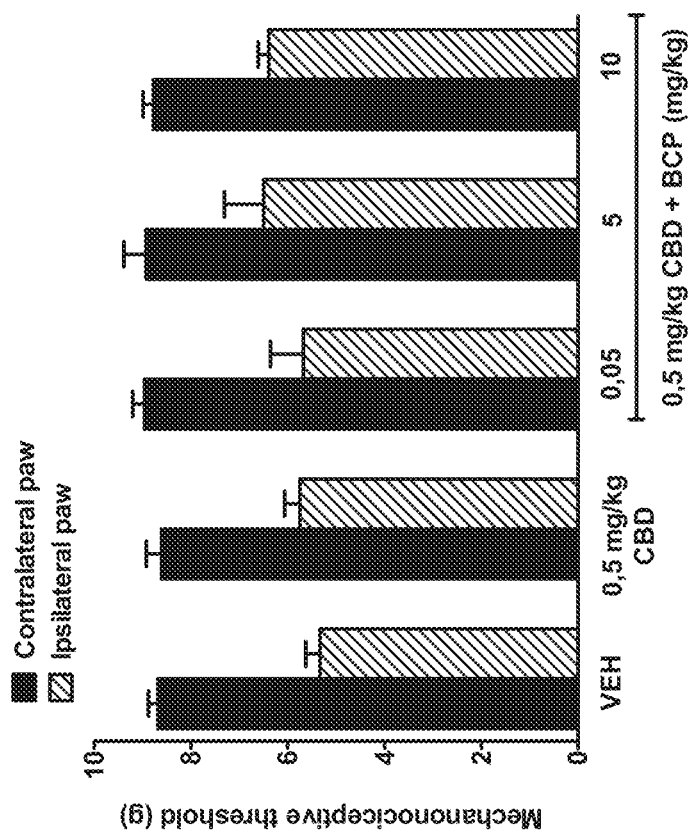
FIG. 14A-FIG. 14B show the effects of CBD+BCP combination treatment on mechanonociceptive thresholds.
Figure 14B:
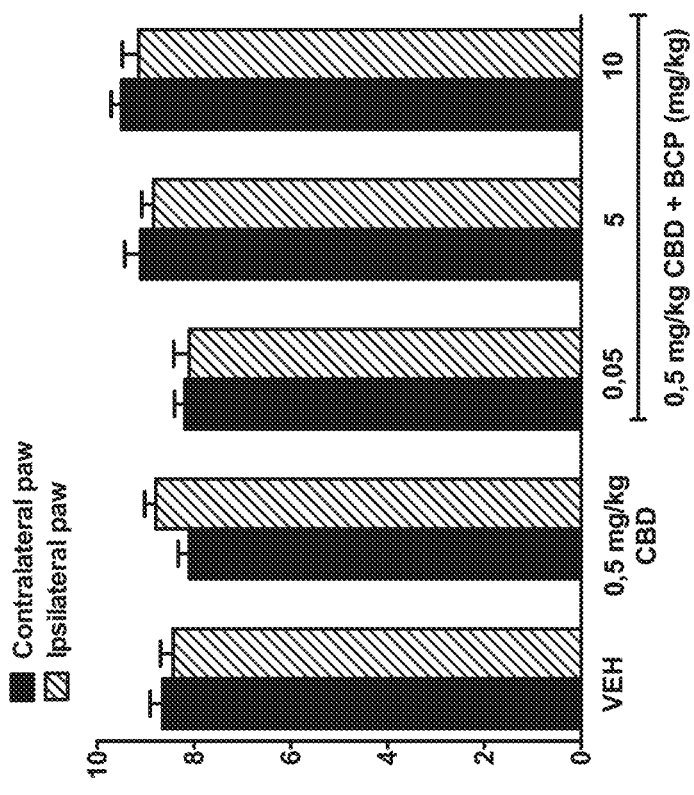
Figure 15B:
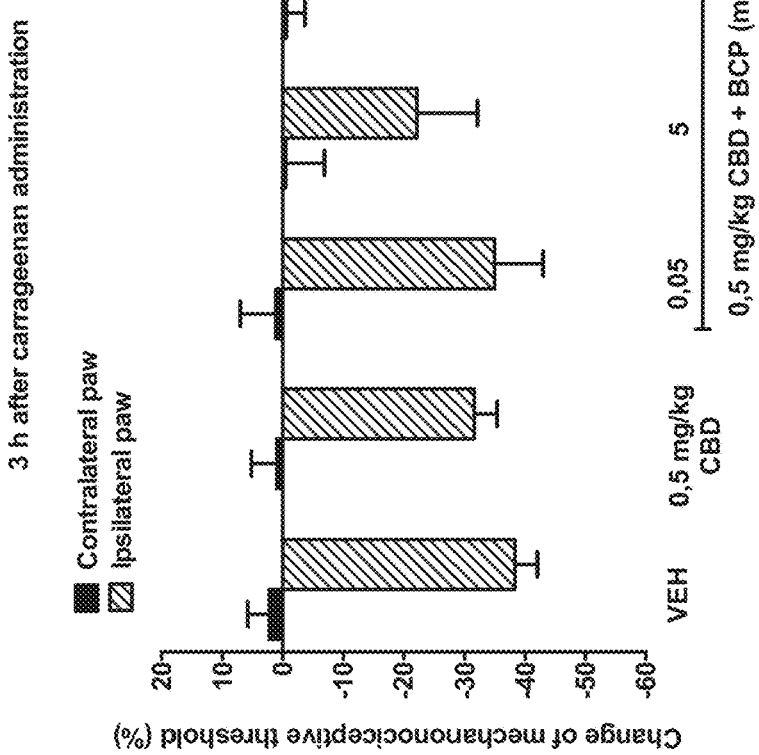
FIG. 15A-FIG. 15B show the data illustrated in FIG. 14 represented as a change in mechanonociceptive threshold as compared to vehicle-treated controls.
Figure 15A:
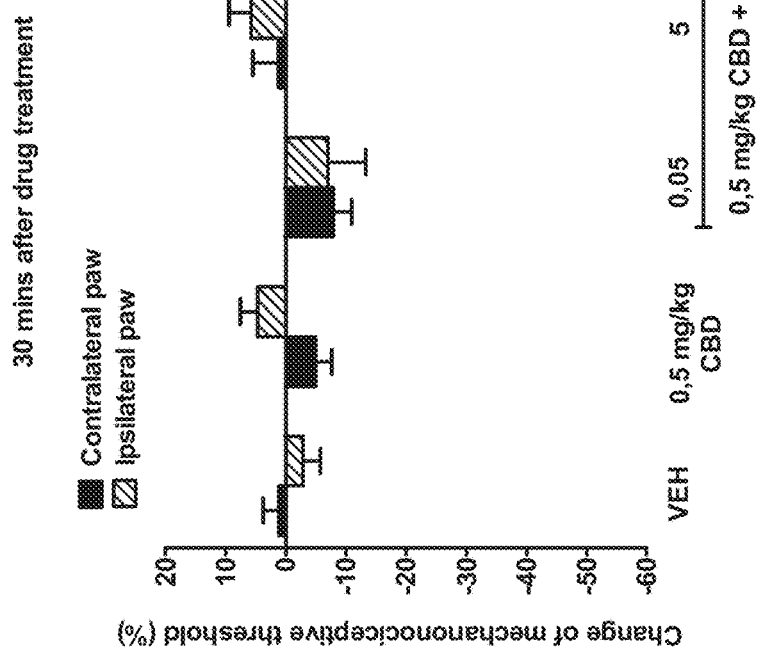

Mechanonociceptive Threshold:

As shown in FIG. 14A and FIG. 15A, none of the investigated combinations of 0.5 mg/kg CBD and BCP (0.05, 5, 10) influenced the basal mechanonociceptive threshold of the hind paws as compared to the vehicle-treated mice 30 min after drug treatment. 3 hours after i.pl. carrageenan administration, a 40% and 30% drop of the mechanonociceptive threshold developed in the vehicle-treated groups which was not influenced by the administration of 0.5 mg/kg CBD (FIG. 14B and FIG. 15B). Among the combined applications, 0.5 mg/kg CBD+5 mg/kg BCP exerted the most pronounced analgesic effects. Notably, the effects of the 00.5 mg/kg CBD+5 mg/kg BCP combination were more robust than the single applications of 0.5 mg/kg CBD or 5 mg/kg BCP when applied alone.

Example 6: Additional Anti-Inflammatory Effects of CBD, BCP, and CBD+BCP Treatment In Vivo Further in vivo studies will be performed to assess the effects of CBD and BCP treatment alone and in combination on additional inflammatory indicators.

Heat-injury induced thermal hyperalgesia model The noxious heat threshold of mice is measured with an increasing-temperature hot plate (IITC Life Science, Woodland Hills, Calif., USA) which has recently been validated (Almasi et al., 2003). After habituation, mice are placed onto the plate, which is then heated up from room temperature at a rate of 12° C./min until the animal showed nocifensive behavior (e.g., licking, lifting, and/or shaking of the hindpaw) or the cut-off temperature (53° C.) was reached. The corresponding plate temperature is considered the noxious heat (thermonociceptive) threshold.

After recording the control threshold as described above, a mild heat injury is applied to one of the hindpaws by immersing the paw in a 51° C. water bath for 15 seconds under brief ether anesthesia. Heat threshold determinations are repeated after heat injury at different time-points (e.g., 5, 10, 15, 20 min, etc.) (See e.g., K. Bolcskei et al. Pain 117 (2005) 368-376). Thermonociceptive thresholds (both under control conditions and after injury) are also recorded at certain time points after intraperitoneal administration of CBD, BCP, or CBD+BCP.

This model is also suitable for assessing heat injury-induced mechanical hyperalgesia. Possible outcomes of these experiments are identification and characterization of CBD and BCP combinations demonstrating enhanced or synergistic effects compared to treatment with either compound alone.

Resiniferatoxin Induced Thermal Hyperalgesia Model

The noxious heat threshold of mice is measured with an increasing-temperature hot plate (IITC Life Science, Woodland Hills, Calif., USA) which has recently been validated (Almasi et al., 2003). After habituation, mice are placed onto the plate, which is then heated up from room temperature at a rate of 12° C./min until the animal showed nocifensive behavior (e.g., licking, lifting or shaking of the hindpaw) or the cut-off temperature (53° C.) was reached. The corresponding plate temperature is considered the noxious heat (thermonociceptive) threshold.

The ultrapotent selective TRPV1 ion channel agonist resiniferatoxin (RTX) is injected intraplantarly (i.pl.) into the right hind paws to induce direct activation of the TRPV1-expressing capsaicin-sensitive peptidergic sensory nerves and a consequent acute neurogenic inflammation with a robust drop of the thermonociceptive thresholds. After applying a single dose (20 µL, 0.03 µg/mL, 10 min before the first measurement), the thermonociceptive thresholds are repeatedly determined at 5, 10, 15 and 20 min to investigate the development of thermal hyperalgesia (See e.g., Á. Horvath et al. Pharmacological Research 131 (2018) 231-243). Thermonociceptive thresholds (both under control conditions and after RTS injection) are also recorded at certain time points after intraperitoneal administration of CBD, BCP, or CBD+BCP.

This model is also suitable for assessing heat injury-induced mechanical hyperalgesia. Possible outcomes of these experiments are identification and characterization of CBD and BCP combinations demonstrating enhanced or synergistic effects compared to treatment with either compound alone.

Example 7: Trial of a High-Cannabidiol Extract in Subjects with Chronic Non-Cancer Pain Despite Optimized Opioid Treatment A study will be performed in association with a pain clinic in the United States to demonstrate the efficacy of the presently claimed formulations in the treatment of non-cancer pain subjects who have inadequate control despite optimized opioid treatment. The study will compare the results of subjects receiving a standardized Good Manufacturing Practice-compliant (GMP) encapsulated pharmaceutical formulation high in cannabidiol (CBD) and beta-caryophyllene (BCP), but low in tetrahydrocannabinol (THC), vs. subjects receiving placebo capsules identical in appearance. The study will be conducted with 30-60 patients over the course of 12 weeks. Prior to commencing the study, subjects will be allowed to dose escalate in three stages over 3 weeks as needed to control pain, but with efforts to avoid adverse events (side-effects). After any necessary dose escalation, subjects will maintain a steady dosage for the remaining 12-weeks of the trial. Dosing will be capped at a limit of 15 mg of THC per day so as to minimize risks of intoxication-type reactions or the development of tolerance.

Subjects will be monitored weekly by telephone call, and will have in-person follow-up clinic visits at Week 0, and Weeks 2, 4, 8 and 12 with a final telephone follow-up at Week 14 (2 weeks after last study drug dosing) to register additional adverse events, and assess changes or withdrawal effects after discontinuation of study drugs.

The primary outcome measure will be measurement of daily pain utilizing an 11-point Numerical Rating Scale (0-10) in which 0 represents no pain, and 10 represents the worst pain one could imagine, registered, for example, via a nightly telephone call utilizing an automated touch-tone response method. A continuous response analysis will be performed and daily opioid utilization will be monitored. Additional secondary outcome measures will include: worst daily pain NRS, and sleep disturbance NRS (via nightly telephone calls), and Hamilton Depression and Anxiety Scores, measures of post-traumatic stress, Columbia Suicide Severity Rating Scale, Patient Global Impression of Change, Physician Global Impression of Change, Caregiver Global Impression of Change, and Quality of Life (QOL) measures assessed at in-person visits. "Pill counts" will be monitored to assess compliance.

The study will be designed to assess the benefits or drawbacks of combining cannabinoid with opioid treatment in the chronic non-cancer pain population. Possible outcomes are improved pain control, opioid-sparing, improved sleep, and improved quality of life.

Example 8: Trial of a High-Cannabidiol, High-Caryophyllene Cannabis Extract in Subjects with Cocaine Dependency This study would be performed through a University, Hospital, Clinic, or other facility with proper approvals and access to subjects and will be performed to demonstrate the efficacy of the presently claimed formulations in the treatment of adult cocaine users who have had previous difficulty maintaining sobriety. This study will compare the outcomes of subjects receiving a standardized Good Manufacturing Practice-compliant (GMP) encapsulated pharmaceutical compositions high in cannabidiol (CBD) and beta-caryophyllene, but low in tetrahydrocannabinol (THC), vs. subjects receiving placebo capsules identical in appearance. The study will include about 40 adult cocaine users, and will last 12 weeks. Prior to commencing the study, subjects will be allowed to dose escalate in three stages over 1 week as needed to control withdrawal symptoms. Subjects will then maintain a steady dosage of study capsules for the remaining 12-week trial. Dosing will be capped at a limit of 10-15 mg of THC per day so as to minimize risks of intoxication-type reactions, or the development of tolerance.

Standard exclusions will include: dependence on opioids or sedatives, concomitant psychosis, dementia, unstable medical illness including cardiac conditions.

Subjects will be monitored weekly by telephone call, and will have in-person follow-up clinic visits at Week 0, and Weeks 2, 4, 8 and 12 with a final telephone follow-up at Week 14 (2 weeks after last study drug dosing) to register additional adverse events, and assess changes or withdrawal effects after discontinuation of study drugs.

The primary outcome measure will be measurement of daily cocaine usage patterns confirmed by weekly qualitative urine benzoylecgonine tests (UBT), as well as subjective measures of craving, withdrawal symptoms, etc. utilizing an 11-point Numerical Rating Scale (0-10) in which 0 represents no symptom, and 10 represents the worst symptom one could imagine, registered via a nightly telephone call utilizing, for example, an automated touch-tone response method. A continuous response analysis will be performed for each parameter. Additional secondary outcome measures will include: average daily and worst daily pain NRS, and sleep disturbance NRS (via nightly telephone calls), Addiction Severity Index (ASI) administered before trial commencement and four times during the trial, weekly measure of withdrawal symptoms via Cocaine Selective Severity Assessment (CSSA) and craving via the Brief Substance Craving Scale (SCCS), with Hamilton Depression and Anxiety Scores, measures of post-traumatic stress, Columbia Suicide Severity Rating Scale, Patient Global Impression of Change, Physician Global Impression of Change, Caregiver Global Impression of Change, and Quality of Life (QOL) measures assessed at in-person visits. Adverse events will be tabulated during clinical encounters, or as needed during the trial. Capsule counts will be utilized to measure compliance. Comparison of abstinence rates of cannabis extract vs. placebo will be calculated at the end of the trial, with follow-up at 1 and 2 months to monitor persistence of sobriety.

The study is designed to assess the benefits or drawbacks of a daily oral agent in treatment of cocaine dependency. Possible outcomes are improved abstinence, pain control, improved sleep, and quality of life.

Example 9: Assessment of CBD and BCP in the Treatment of Epilepsy

Additional studies can be performed to determine the efficacy of CBD and BCP in the clinical treatment of epilepsy. This study would be performed through a University, Hospital, Clinic, or other facility with proper approvals and access to subjects and will be performed to demonstrate the efficacy of the presently claimed formulations in the treatment of adults suffering from epilepsy that is inadequately controlled by the standard of care treatment. This study will compare the outcomes of subjects receiving a standardized Good Manufacturing Practice-compliant (GMP) encapsulated pharmaceutical compositions high in CBD and BCP, but low in tetrahydrocannabinol (THC), vs. subjects receiving placebo capsules identical in appearance.

The study will be designed to assess the benefits or drawbacks of treating epilepsy patients with pharmaceutical compositions containing different ratios of CBD and BCP (for example, CBD to BCP ratio of about 1:10; about 1:5; about 1:1; about 5:1 and about 10:1), as well as to assess the benefits or drawbacks of combining CBD and BCP compositions with current epilepsy treatments. Possible outcomes are reduced seizure frequency, reduced seizure intensity, reduced seizure-induced memory loss, and improved quality of life. Further possible outcomes include identification of particular CBD to BCP ratios providing an increased clinical benefit in the treatment of epilepsy compared to other tested CBD to BCP ratios.

Example 10: Assessment of CBD and BCP in the Treatment of Chronic Pain

Additional studies can be performed to determine the efficacy of CBD and BCP in the clinical treatment of chronic pain. This study would be performed through a University, Hospital, Clinic, or other facility with proper approvals and access to subjects and will be performed to demonstrate the efficacy of the presently claimed formulations in the treatment of adults suffering from chronic pain that is inadequately controlled by the standard of care treatment (e.g., patients who have developed a tolerance to opioid treatment). This study will compare the outcomes of subjects receiving a standardized Good Manufacturing Practice-compliant (GMP) encapsulated pharmaceutical compositions high in CBD and BCP, but low in tetrahydrocannabinol (THC), vs. subjects receiving placebo capsules identical in appearance.

The study will be designed to assess the benefits or drawbacks of treating chronic pain patients with pharmaceutical compositions containing different ratios of CBD and BCP (for example, CBD to BCP ratio of about 1:10; about 1:5; about 1:1; about 5:1 and about 10:1). Possible outcomes are reduced pain as indicated by a change in one or more clinical pain scales compared to a placebo, reduced frequency or amount of traditional pain killers (e.g., opioid) taken by treated patients, low adverse event profile and low drug abuse liability, improved sleep and improved quality of life. Further possible outcomes include identification of particular CBD to BCP ratios providing an increased clinical benefit in the treatment of chronic pain compared to other tested CBD to BCP ratios.

Example 11: Assessment of the Anti-Inflammatory Effect of Novel Semi-Synthetic Phytocannabinoids in RAW 264.7 Cells Experiments were performed to compare the effects of CBD vs. semi-synthetic F-CBDs in various keratinocyte inflammation models.

Cell Culture:

Human immortalized HaCaT keratinocytes were cultured in one of two media: (i) serum-free EpiLife medium (Life Technologies) supplemented with Human Keratinocyte Growth Supplement (HKGS; at 1:100; Life Technologies)

and a preformed antibiotic mixture of 1:100 penicillin and streptomycin (PAA Laboratories) and 1:200 Fungizone® Antimycotic in (Life Technologies); or (ii) Dulbecco's Modified Eagle Medium (DMEM; Life Technologies) supplemented with 10 (V/V) % fetal bovine serum (FBS; Life Technologies) and the above mentioned antibiotic/Fungizone® Antimycotic mixture. Cells were cultured at 37° C. in humidified, 5% $CO_2$ containing atmosphere. Media was changed every other day, and cells were sub-cultured at 70-80% confluence in all cases Agents Tested:
(a) CBD;
(b) HUF-101;
(c) HUF-103; and
(d) HU-559a All compounds were applied 30 min before the induction of inflammation by the indicated stimuli in each model.

Assessment of Inflammatory Markers by RT-qPCR:

RT-qPCR experiments were performed as described previously (Olah et al., 2014) on a Roche Light Cycler 480 QPCR System (Roche Applied Sciences) using the 5' nuclease assay. In brief, total RNA was isolated using TRIzol (LifeTechnologies), DNase treatment was performed according to the manufacturer's protocol, and then 1 μg of total RNA were reverse-transcribed into cDNA by using High Capacity cDNA Kit from Life Technologies. PCR amplification was performed by using the TaqMan primers and probes (assay IDs: Hs00174092_m1 for IL-1α, Hs00174097_m1 for IL-1β, Hs00985639_m1 for IL-6, Hs00174103_m1 for IL-8 and Hs00174128_m1 for TNFα). As internal control, expression of peptidyl-prolyl isomerase A (PPIA) or 18S RNA were used (assay IDs: Hs99999904_m1 for PPIA, and Hs03928905_g1 for 18S RNA). The amount of the transcripts was normalized to those of the housekeeping gene using the ΔCT method. When indicated, the results were then normalized to the expression of the vehicle control or the LTA-treated culture (ΔΔCT method), and were plotted as mean±SD of 3 technical replicates.

Inflammatory Epidermal Keratinocyte Models:

The details of each model tested are listed below. A summary of the key features of each model is provided in Table 9.

(a) Non-Specific Irritation and Inflammation Model—Model for Common Irritative Dermatitis:

Human epidermal keratinocytes were treated for 24 hrs with 1 μM Sodium Dodecyl Sulfate (SDS), a non-specific skin irritant, to induce non-specific irritation. After 24 hrs, elevated mRNA levels of interleukin IL6 and IL8 were observed.

(b) Contact Irritation and Inflammation Model—Model for Allergic Contact Dermatitis:

Human epidermal keratinocytes were treated for 6 hrs with 1 μM Nickel, which, in sensitive subjects, often causes contact dermatitis, to induce contact irritation. After 6 hrs, elevated mRNA levels of IL6 and IL8 were observed.

(c) Chemical Irritation and Inflammation Model—Model for Chemical-Induced Irritative Dermatitis:

Human epidermal keratinocytes were treated for 6 hrs with 300 μM Carvacrol, a TRPV3 ion channel agonist (activation of TRPV3 in epidermal keratinocytes is known to result in inflammation) to induce chemical irritation. After 6 hrs, elevated mRNA levels of IL1α, IL6, IL8, and tumor necrosis factor TNFα were observed.

(d) Protease-Induced Irritation and Inflammation Model—Model for Pruritic Dermatitis/Dermatosis:

Human epidermal keratinocytes were treated for 3 hrs with 10 μM SLIGRL, an agonist of protease-activated PAR2 receptor (activation of PAR2 in epidermal keratinocytes is known to result in the release of itch-inducing mediators and inflammation) to induce pruritic irritation. After 3 hrs, elevated mRNA levels of IL6 and IL8 were observed.

(e) UV-Induced Irritation and Inflammation Model—Model for Pruritic Dermatitis/Dermatosis:

Human epidermal keratinocytes were irradiated for 6 hrs with 40 $mJ/cm^2$ UVB light to induce solar irritation. After 6 hrs, elevated mRNA levels of IL1α, IL1β, IL6, and IL8 were observed.

(f) TLR3-Induced Irritation and Inflammation Model—Model forMicrobial Dermatitis:

Human epidermal keratinocytes were treated for 3 hrs with 20 μg/ml Polyinosinic:polycytidylic acid (Poly p(I:C)), activator of toll-like receptor TLR3 (activation of TLR3 in epidermal keratinocytes is known to result in inflammation) to induce solar irritation. After 3 hrs, elevated mRNA levels of IL1α, IL1β, IL6, and IL8 were observed.

(g) Atopic Model—Model for Atopic Dermatitis:

Human epidermal keratinocytes were treated for 24 hrs with the combination of 100 ng/ml *Staphylococcus aureus* enterotoxin B (SEB) and 30 ng/ml thymic stromal lymphopoietin (TSLP), 2 key molecules in the pathogenesis of atopic dermatitis. After 24 hrs, elevated mRNA levels of IL1α, IL6, and IL8 were observed.

TABLE 9

Summary of Inflammatory Skin Models

| Model | Protocol | Read-out | Related Disease |
|---|---|---|---|
| Non-specific irritation & inflammation | SDS (1 μM) treatment for 24 hrs | IL6, IL8 | Common irritative dermatitis |
| Contact irritation & inflammation | Nickel (1 μM) treatment for 6 hrs | IL6, IL8 | Allergic contact dermatitis |
| Chemical irritation & inflammation | Carvacrol (300 μM) treatment for 6 hrs | IL1α, IL6, IL8, TNFα | Chemical-induced irritative dermatitis |
| Protease-induced irritation & inflammation | SLIGRL (10 μM) treatment for 3 hrs | IL6, IL8 | Pruritic dermatitis/dermatosis |
| UV-induced irritation & inflammation | UVB (40 $mJ/cm^2$) irradiation for 6 hrs | IL1α, IL1β, IL6, IL8 | Solar dermatitis, solar burns |
| TLR3-induced irritation & inflammation | Poly p(I:C) (20 μg/mL) treatment for 3 hrs | IL1α, IL1β, IL6, IL8 | Bacterial, viral, and other microbial dermatitis |

TABLE 9-continued

Summary of Inflammatory Skin Models

| Model | Protocol | Read-out | Related Disease |
| --- | --- | --- | --- |
| Atopic model | SEB (100 ng/mL) and TSLP (30 ng/mL) treatment for 48 hrs | IL1α, IL6, IL8 | Atopic dermatitis |

Results:

The putative anti-inflammatory effects of CBD and F-CBDs were evaluated by measuring their ability to suppress pro-inflammatory cytokine expression induced by the stimuli in each of the different models tested (i.e., SDS, Ni, Carvacrol, UVB, p(I:C), and SEB/TSLP. A summary of these results are shown in FIG. 18A (Models 1-3) and FIG. 18B (Models 4-7). The values in the tables indicate the relative change in gene expression of the indicated cytokine as a result of treatment with the test agents relative to the expression level measured with the stimuli alone (referred to in this Example as the positive control). Therefore, in FIGS. 18A and 18B, the lower the number, the higher the degree of inhibition. The bolded values indicate an expression level of the indicated cytokine gene that is <50% relative to the positive control (i.e. a reduction in the gene expression of greater than 50%). The values that are bolded and underlined indicate an expression level of the indicated cytokine gene that is <30% relative to the positive control (i.e. a reduction in the gene expression of greater than 70%).

Figure 19A:
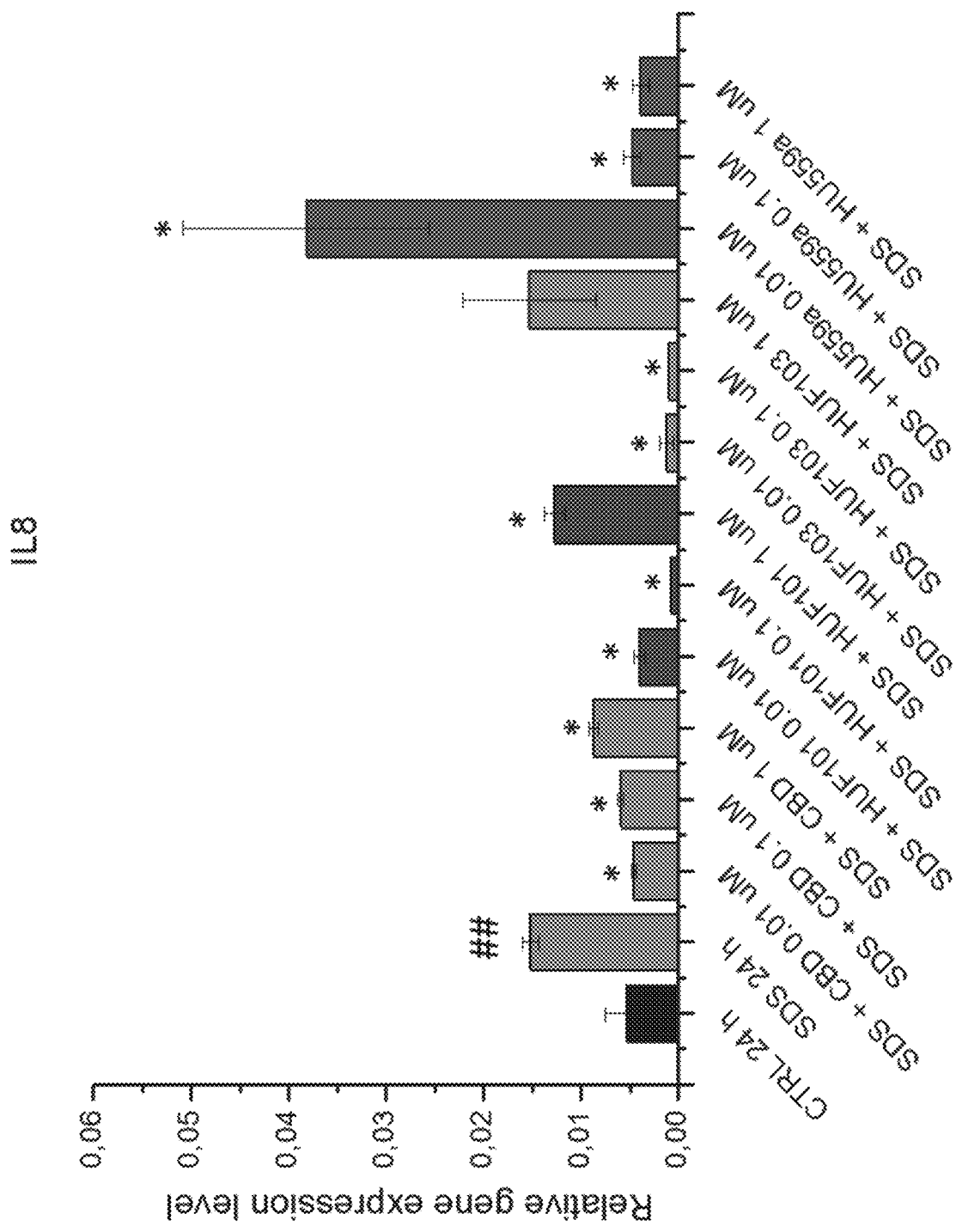
FIG. 19A-FIG. 19B illustrate the effects of CBD and F-CBDs on IL-8 gene expression in models of skin inflammation.
Figure 19B:
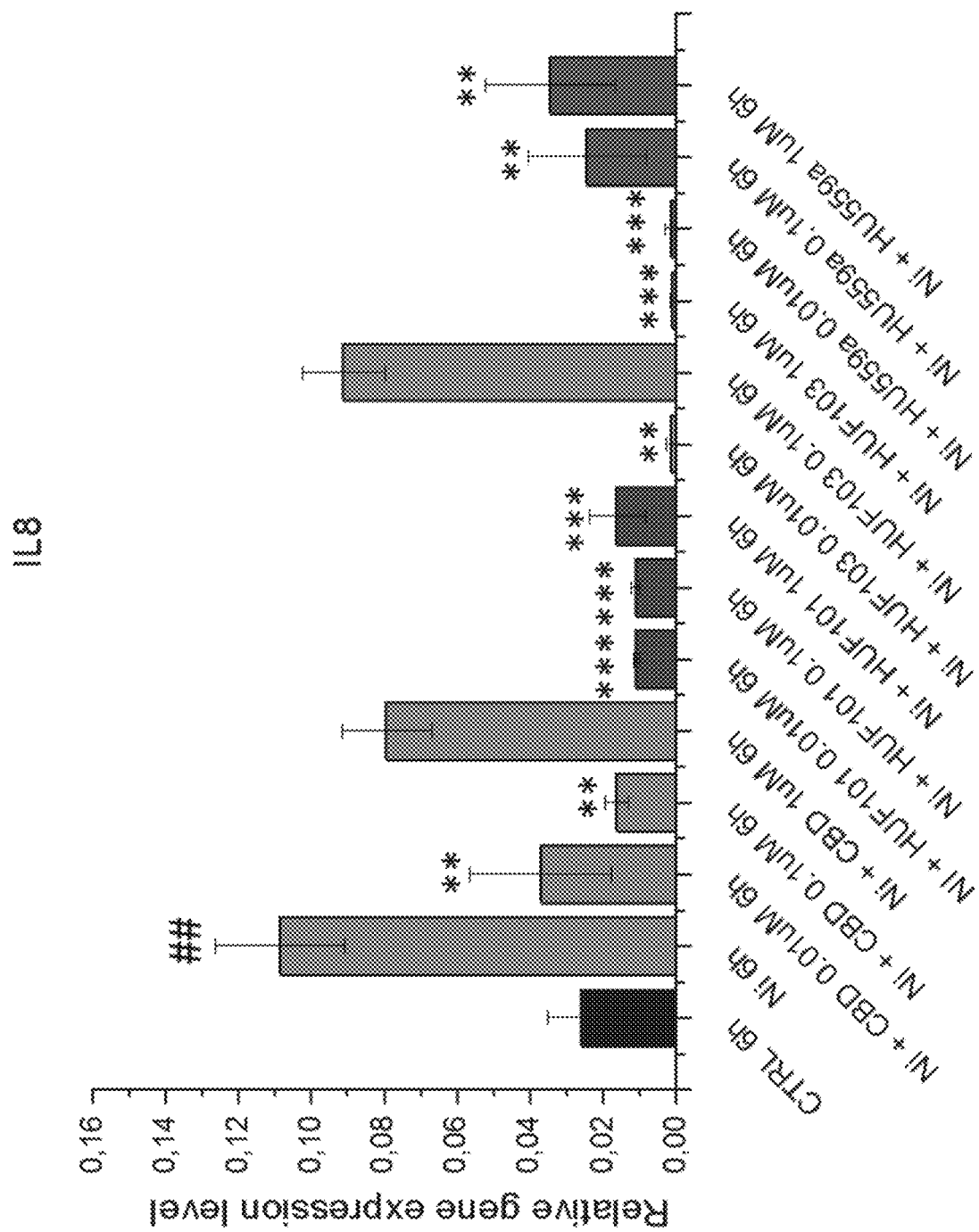
Figure 20A:
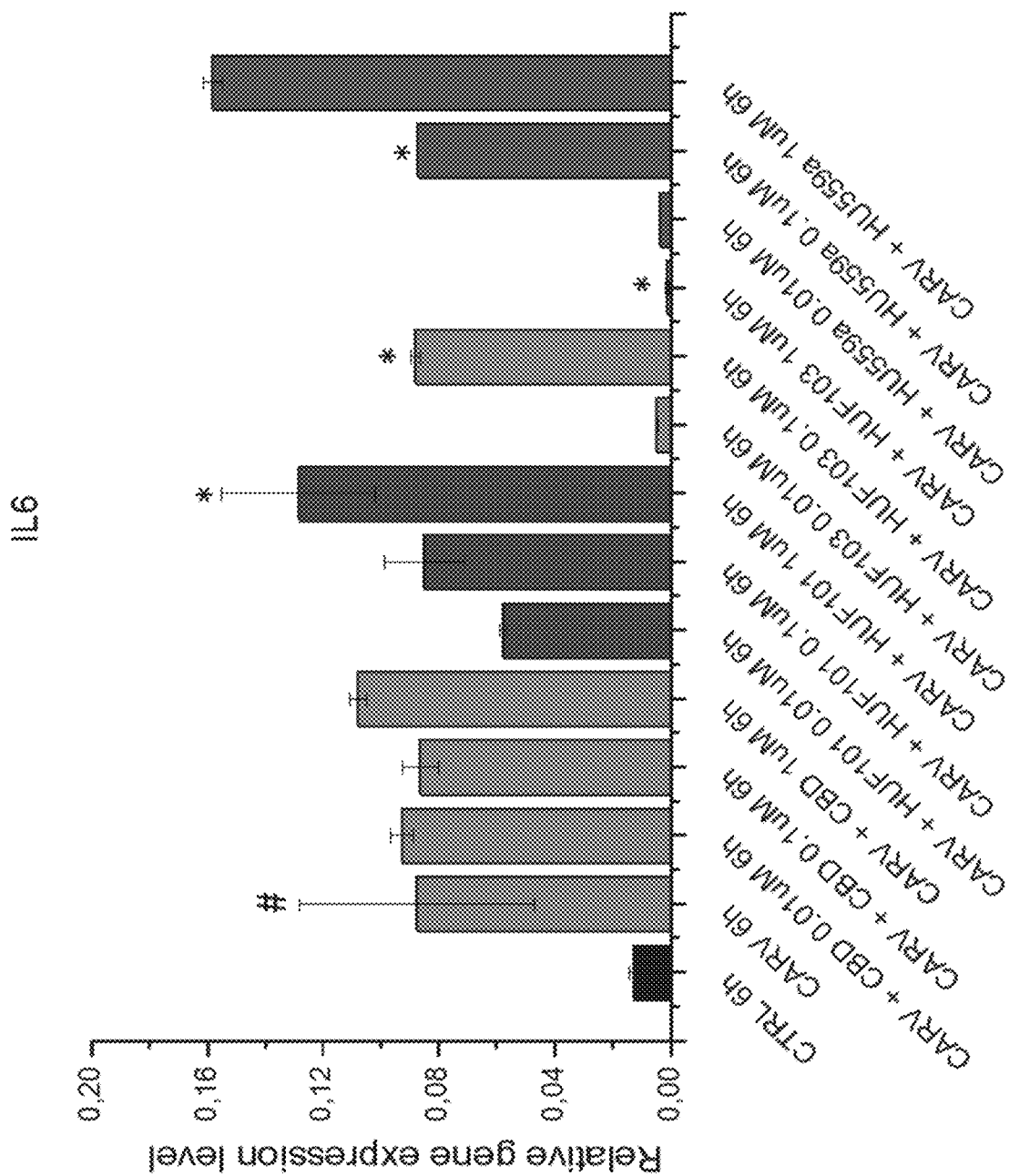
FIG. 20A-FIG. 20B illustrate the effects of CBD and F-CBDs on IL-6 gene expression (FIG. 20A) and IL-8 (FIG. 20B) in a chemical-induced inflammation/irritation model of skin inflammation.
Figure 20B:
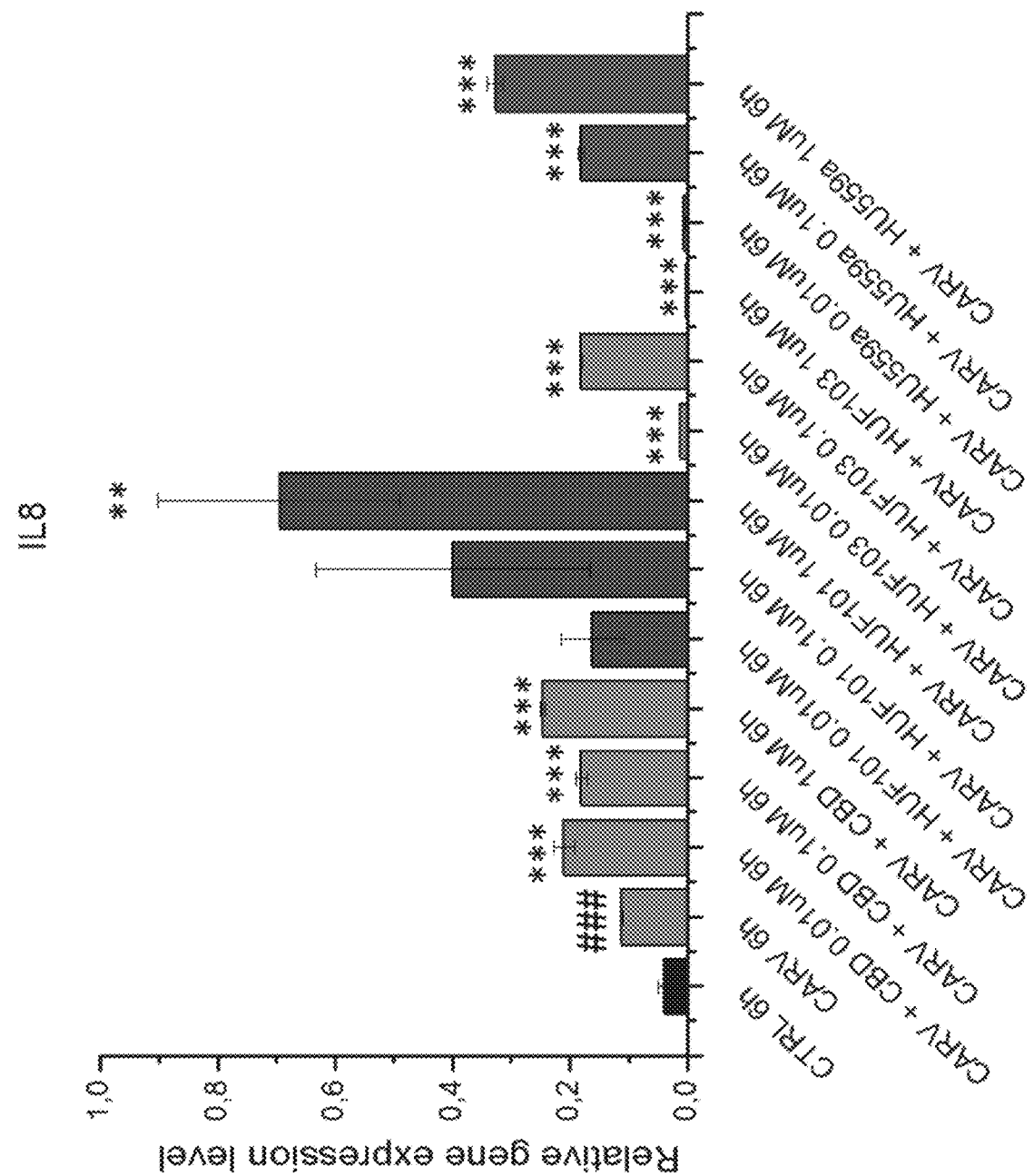
Figure 21A:
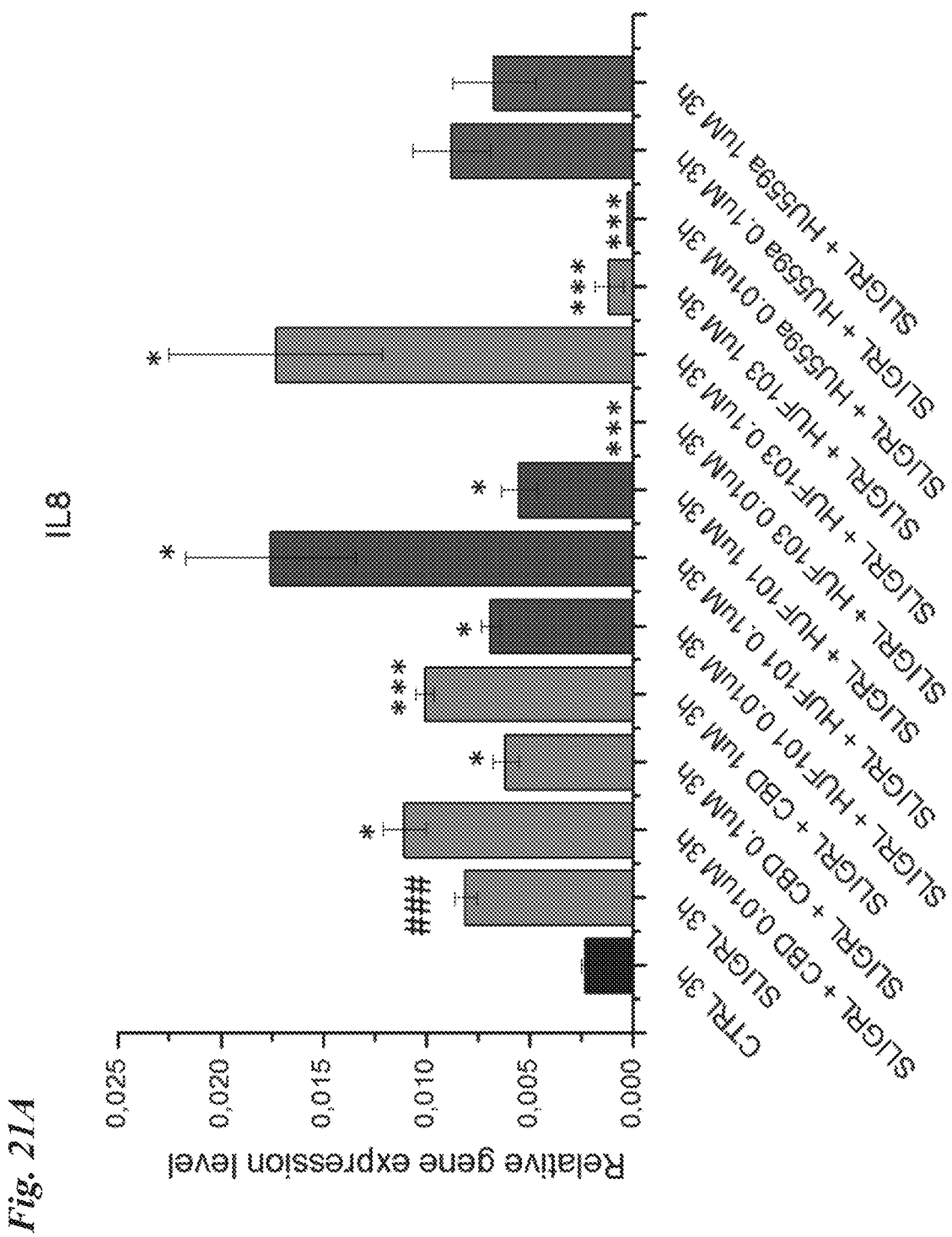
FIG. 21A-FIG. 21B illustrate the effects of CBD and F-CBDs on IL-8 gene expression in models of skin inflammation.
Figure 21B:
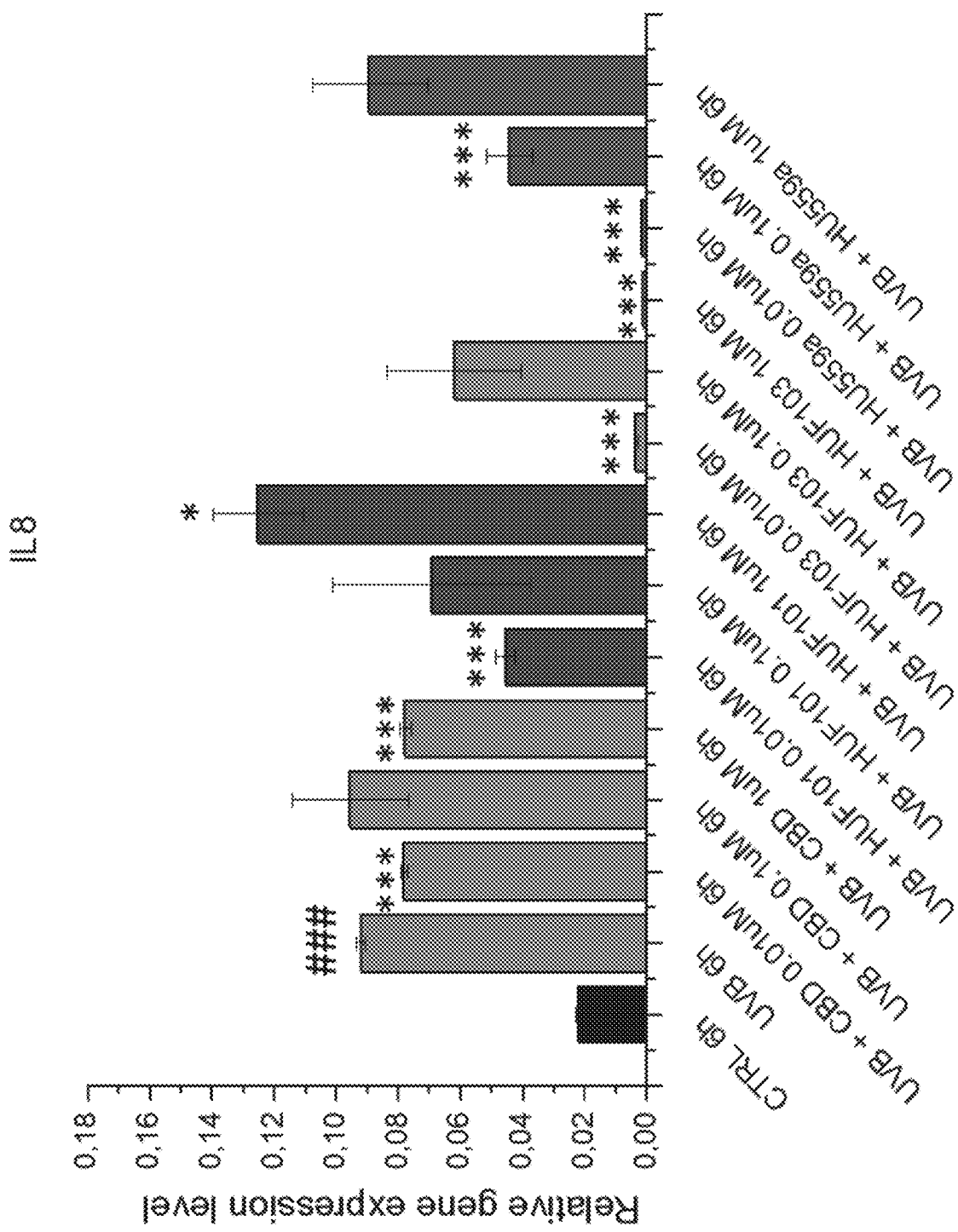
Figure 22A:
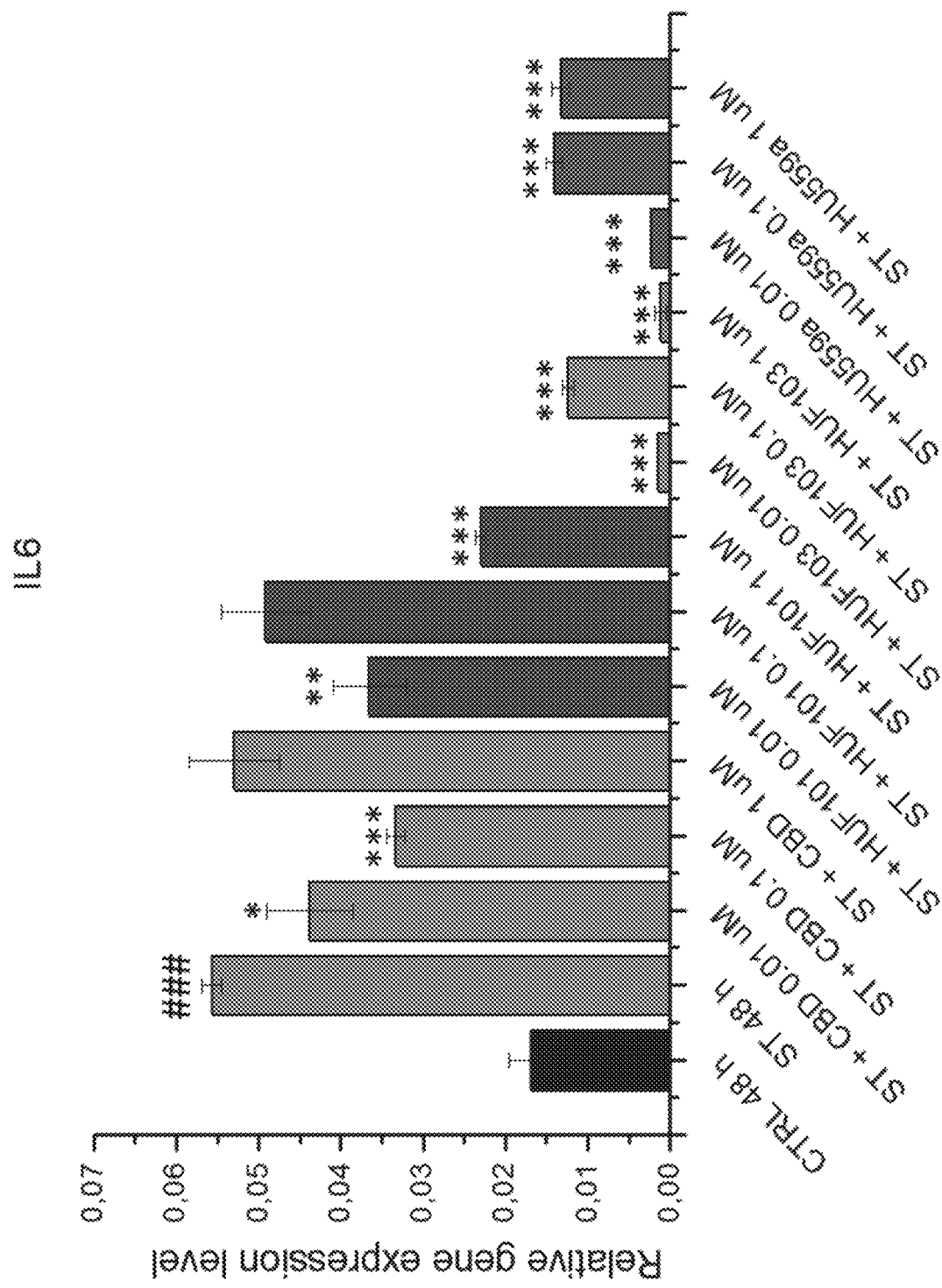
FIG. 22A-FIG. 22B illustrate the effects of CBD and F-CBDs on IL-6 gene expression (FIG. 22A) and IL-8 (FIG. 22B) in a SEB/TSLP-induced inflammation/irritation model.
Figure 22B:
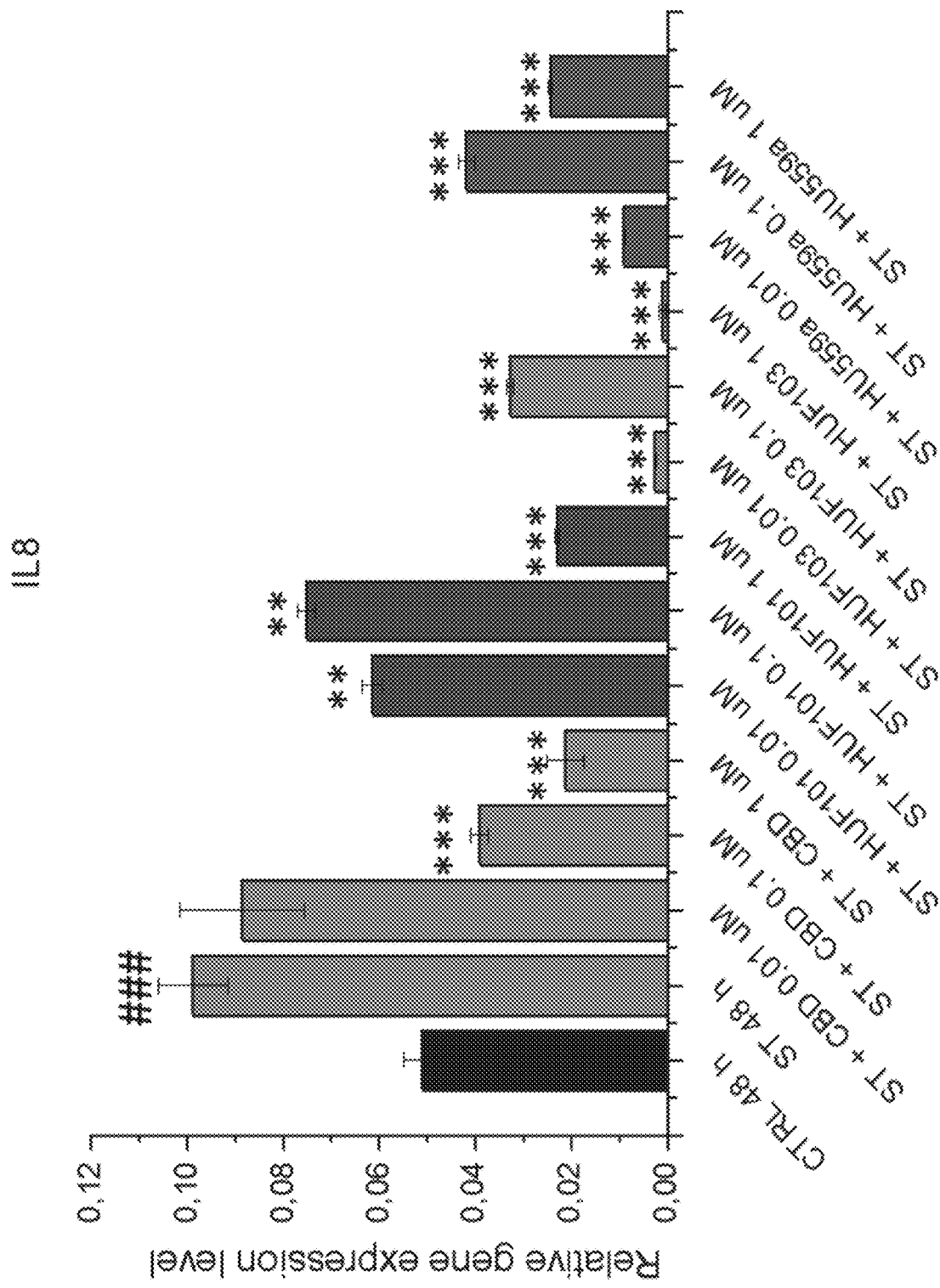
Figure 23:
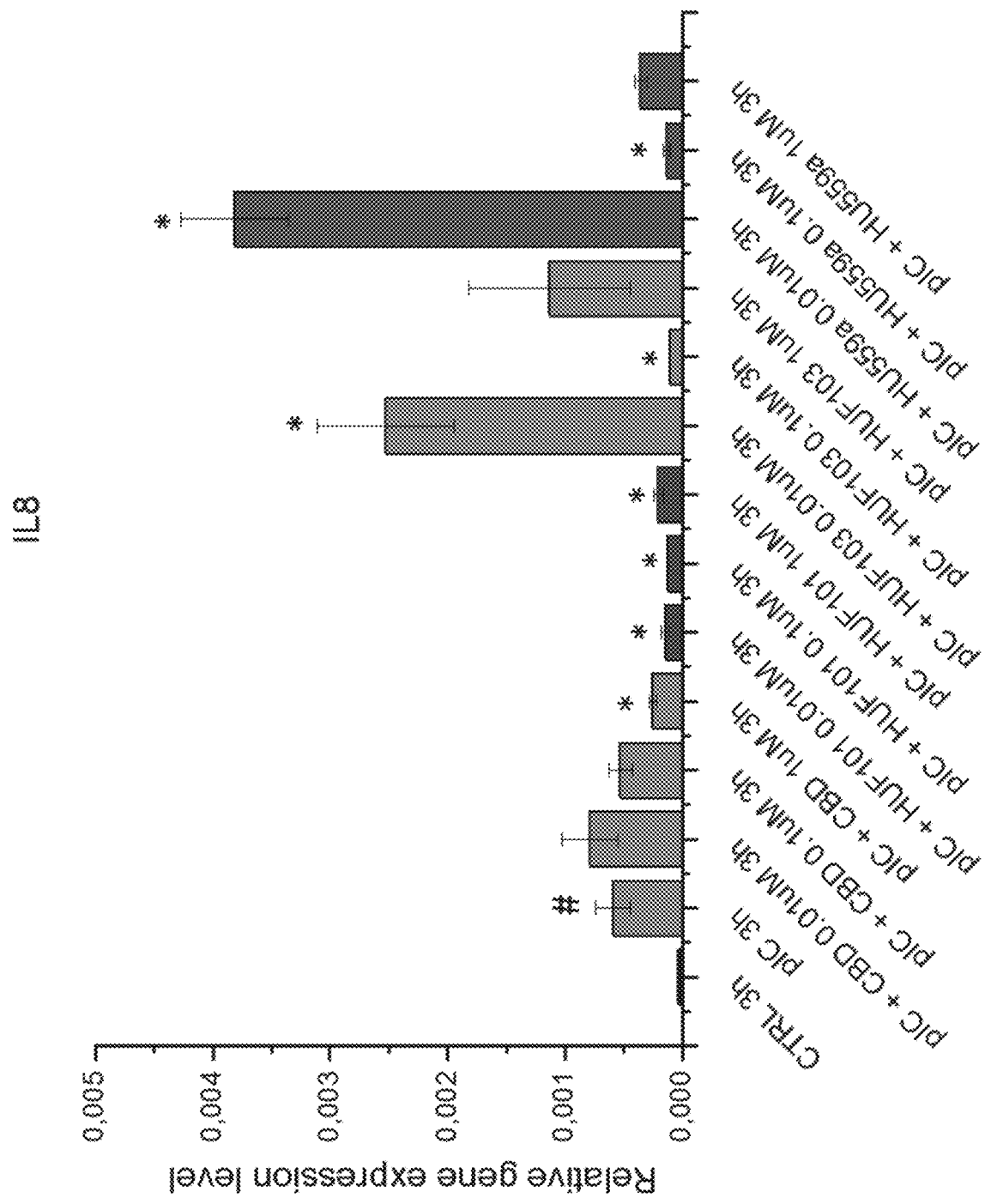
FIG. 23 illustrates the effects of CBD and F-CBDs on IL-8 gene expression in a TLR3 activation inflammation/irritation model.

Graphical representations of a selection of these results are also provided. In FIG. 19A, the effects of these compounds on IL-8 gene expression in the non-specific inflammation/irritation model are shown (#$p<0.05$, compared to the vehicle control group; * $p<0.05$ compared to the SDS group). In FIG. 19B, the effects of these compounds on IL-8 gene expression in the contact allergic inflammation/irritation model are shown (##$p<0.01$, compared to the vehicle control group;  $p<0.01$, * $p<0.001$ compared to the Ni-treated-group). In FIG. 20, the effects of these compounds on IL-6 gene expression (FIG. 20A) and IL-8 (FIG. 20B) in the chemical-induced inflammation/irritation model are shown (#$p<0.05$, ###$p<0.001$ compared to the vehicle control group; * $p<0.05$, *** $p<0.001$ compared to the Carvacrol group). In FIG. 21A, the effects of these compounds on IL-8 gene expression in the PAR2-receptor activation inflammation/irritation model are shown (###$p<0.001$, compared to the vehicle control group; * $p<0.05$, *** $p<0.001$ compared to the SLIGRL-group). In FIG. 21B, the effects of these compounds on IL-8 gene expression in the UVB-induced inflammation/irritation model are shown (###$p<0.001$, compared to the vehicle control group; * $p<0.05$, *** $p<0.001$ compared to the UVB-group). In FIG. 22, the effects of these compounds on IL-6 gene expression (FIG. 22A) and IL-8 (FIG. 22B) in the SEB/TSLP-induced inflammation/irritation model are shown (###$p<0.001$, compared to the vehicle control group; * $p<0.05$,  $p<0.01$, * $p<0.001$ compared to the SEB/TSLP group). In FIG. 23, the effects of these compounds on IL-8 gene expression in the TLR3 activation inflammation/irritation model are shown (#$p<0.05$, compared to the vehicle control group; * $p<0.05$ compared to the pIC group).

Conclusion:

All F-CBD compounds exerted higher anti-inflammatory efficacy than CBD. Among the F-CBDs, the rank order of efficacy is HUF103>HU559a>HUF101. In multiple cases, the lower concentrations proved to be more effective than the higher ones (characteristics for phytocannabinoids when assessing the anti-inflammatory actions). In certain cases, some of the compounds (actually at the higher, 1 μM concentration) showed different degrees of pro-inflammatory effects. Therefore, these data indicate the F-CBDs may have clinical relevance in the treatment of inflammatory skin conditions.

Example 12: Assessment of the In Vivo Effects of Novel Semi-Synthetic Phytocannabinoids Experiments were performed to assess the effects of CBD and HUF101 in an in vivo model of atopic contact dermatitis. Additional experiments will be performed to assess the effects of other semi-synthetic phytocannabinoids (e.g., HUF103 and HUF559a) in models of skin inflammation.

Solution Preparation, Drug Administrations:

Prednisolone was solved in 1:1 of DMSO/saline and was administered topically (15-15 μL to the inner and outer surface of the ears). All other test compounds were solved in 96% ethanol. All solutions of all the concentrations were prepared freshly on the first day of every experiment and were stored at 4° C., then shaken properly before the treatments.

Figure 24:
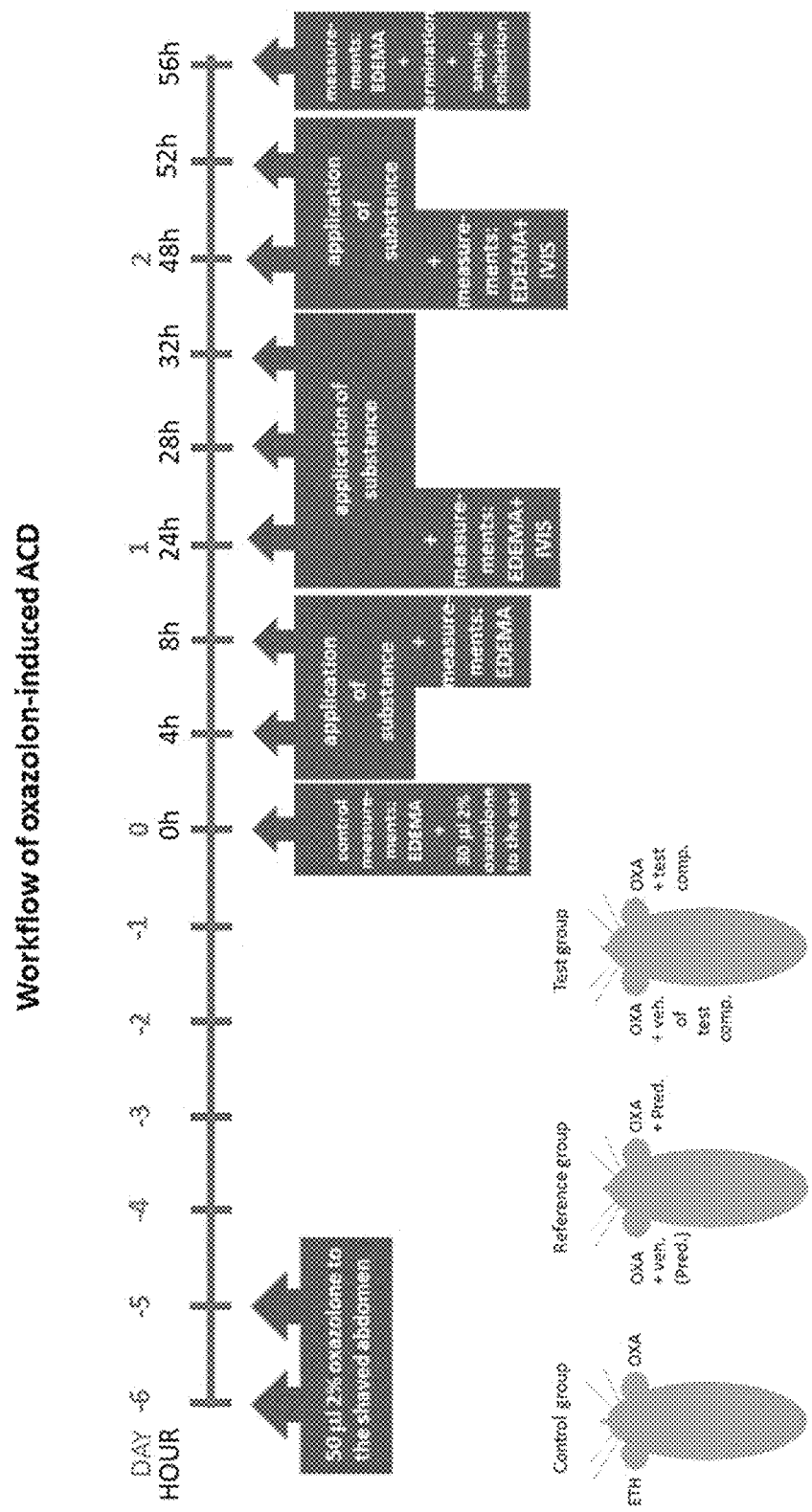
FIG. 24 shows a schematic of the experimental protocol for a murine model of atopic contact dermatitis.

Oxazolone-Induced Allergic Contact Dermatitis Model—Model for Human Atopic Dermatitis (AD):

Anesthesia was induced by ketamine (Richter Gedeon, Budapest, Hungary) (100 mg/kg i.p., repeated as required) with xylazine (Lavet Ltd., Budapest, Hungary) (5 mg/kg i.m.). Animals were sensitized on two consecutive days by painting 2% oxazolone (50-50 μL, Merck KGaA) on the shaved abdomen. On the $6^{th}$ day the right ears were smeared with 2% oxazolone (OXA) dissolved in 96% ethanol: 15-15 μL solution was applied on each of the inner and outer surfaces. Control ears were treated with 96% ethanol in the same way. Drug-treated groups were treated with 15-15 μL of drug solution smeared to the inner and outer side of the ears every 4 hrs of the experiment after oxazolone treatment. A schematic of the experimental protocol is provided in FIG. 24 and the experimental groups are defined below.

(a) Group 1: Ethanol-treated Controls: left ear: 96% ethanol, right ear: 2% oxazolone
(b) Group 2: 1 μM CBD
(c) Group 3: 10 μM CBD
(d) Group 4: 1 μM HU101
(e) Group 5: 10 μMHU101

Measurement of the Ear Edema:

Ear thickness was measured with an engineer's micrometer, with 0.1 mm accuracy, before challenge with test agents and after the challenge at different time points. Data are expressed as % increase of ear thickness compared to the initial values.

Statistical Analysis:

Results are expressed as mean±SEM. Comparisons between different treatment groups were performed using two-way ANOVA followed by Sidak's post hoc test for skin thickness and one-way ANOVA followed by Bonferroni's post hoc test for MPO and vascular leakage. * p<0.05 was considered to be significant.

Figure 25:
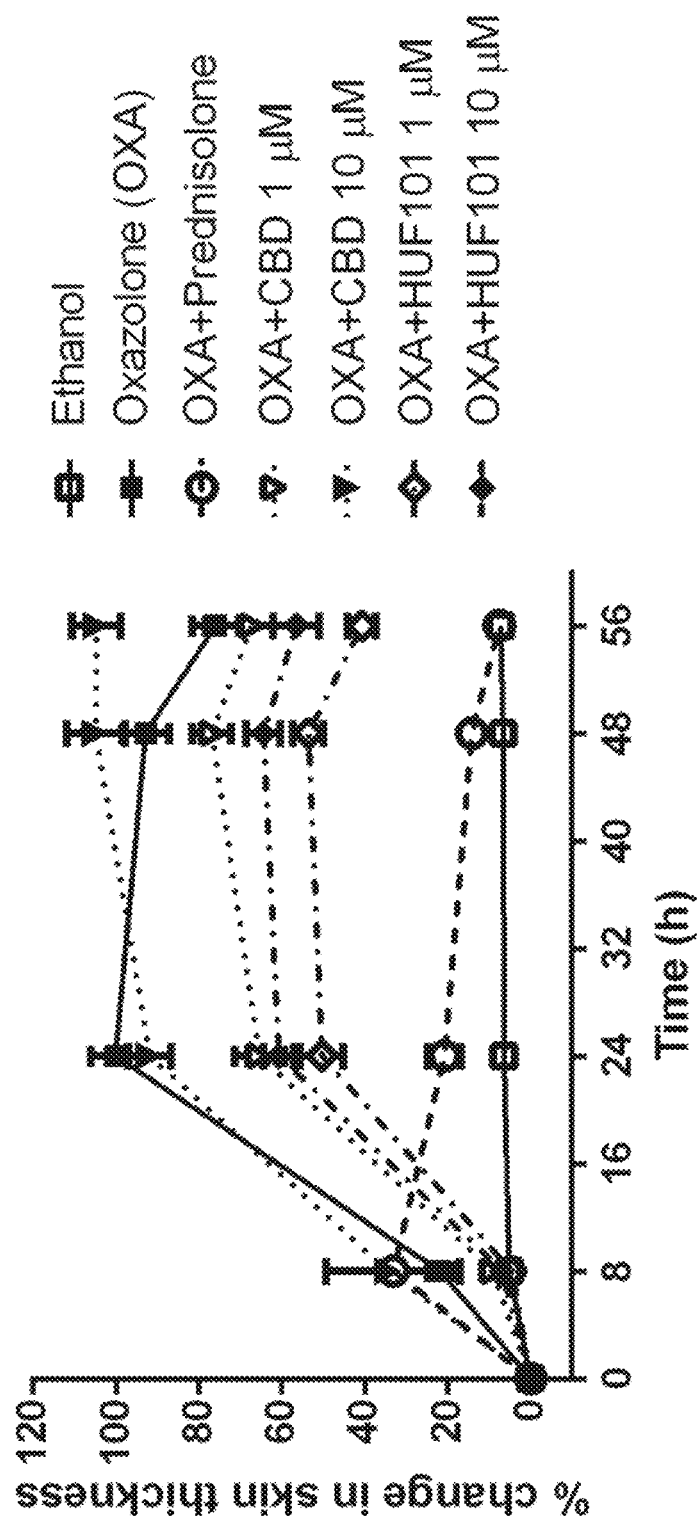
FIG. 25 shows the effects of CBD and HUF101 on ear edema in the murine model of atopic contact dermatitis shown in FIG. 24.

Results:

Results of this experiment are provided in FIG. 25 and in Table 10 below.

TABLE 10

Effect of compounds in ACD mouse model

| Exp. Groups Compared | 24 h | 48 h | 56 h |
|---|---|---|---|
| OXA vs. OXA + CBD 1 μM | ** | | |
| OXA vs. OXA + HUF101 1 μM | *** | *** | *** |
| OXA vs. OXA + HUF101 10 μM | *** | *** | * |
| OXA + CBD 1 μM vs. OXA + CBD 10 μM | | | * |
| OXA + CBD 10 μM vs. OXA + HUF101 1 μM | ** | *** | *** |
| OXA + CBD 10 μM vs. OXA + HUF101 10 μM | | ** | *** |

* $p \leq 0.05$;
** $p \leq 0.01$;
*** $p \leq 0.001$

As shown, the positive control (Prednisolone) exerted the most robust reduction in OXA-induced edema formation. Topically applied 1 μM CBD significantly prevented OXA-induced edema formation at the 24 hr time-point (whereas its effect was only minor at later time-points). Topically applied 10 μM CBD did not exert any anti-inflammatory effect. Actually, the efficacy of 1 μM CBD was statistically significantly better at 56 hr time-point than that of 10 μM CBD. Importantly, both HUF-101 doses (1 μM and 10 μM), when administered topically, exerted statistically significant anti-inflammatory actions at all time-points. The efficacy of 1 μM HUF-101 was somewhat higher than that of 10 μM HUF-101. Further, both HUF-101 doses exerted more robust effects than either 1 μM or 10 μM CBD and was statistically significant compared to the effect of 10 μM CBD. The efficacy of the most potent 1 μM HUF-101 was ca. 40-60% of the efficacy of prednisolone, depending on the time-point investigated.

Example 13: Assessment of the In Vitro and In Vivo Effects of Cannabis Extracts

Experiments will be performed to compare the effects of compositions comprising substantially pure CBD and BCP to the effects of cannabis extracts in various in vitro and in vivo inflammation models. These studies are designed to assess the benefits of compositions comprising substantially pure CBD and BCP compared to whole cannabis extracts.

Based on the results described in Examples 1-12, select concentrations and combinations of CBD and BCP will be compared to extracts from a variety of cannabis strains. For example, the experiment can be performed with an extract from a chemotype III plant with beta caryophyllene, extracts from plants containing only THC, extracts from plants containing both THC and CBD, and extracts from plants containing only CBD.

Assays can be performed to determine the effect of cannabis extracts on NFκB activation (Example 1), changes in cytokine gene expression in response to inflammatory stimuli (Example 2), edema (Examples 3, 4, 5), mechanonociceptive thresholds (Examples 3, 4, 5), thermonociceptive thresholds (Example 6), efficacy in the treatment of pain (Examples 7 and 10), efficacy in the treatment of addiction (Example 8), efficacy in the treatment of epilepsy (Example 9), effects in in vitro models of inflammatory skin diseases (Example 11), and effects in in vivo models of inflammatory skin diseases (Example 12).

Possible outcomes of these experiments are identification and characterization of CBD and BCP concentrations and combinations that demonstrate enhanced effects compared to treatment with whole cannabis extracts.

Example 14: Assessment of CBD and BCP in In Vitro and In Vivo Models of Inflammatory Skin Diseases Experiments will be performed to assess the effects of CBD, BCP, and CBD+BCP compositions in various models of inflammatory skin diseases. Experiments will be performed with concentrations and combinations of CBD and BCP identified in Examples 1-6. These concentrations and combinations will then be used in the experimental models described in Examples 11 and 12 according to the protocols described therein.

Possible outcomes of these experiments are identification and characterization of CBD and BCP combinations demonstrating enhanced or synergistic effects in models of skin inflammation compared to treatment with either compound alone.

EMBODIMENTS

The following are exemplary enumerated embodiments of the present disclosure.

Embodiment 1

A pharmaceutical composition comprising one or more active ingredients, wherein the active ingredient portion of the composition consists essentially of a therapeutically effective amount of CBD and (E)-BCP.

Embodiment 2

The pharmaceutical composition of Embodiment 1, wherein the active ingredient portion of the composition consists of a therapeutically effective amount of CBD and (E)-BCP.

Embodiment 3

The pharmaceutical composition of Embodiment 1, wherein at least one of CBD and (E)-BCP is an enriched active ingredient.

Embodiment 4

The pharmaceutical composition of Embodiment 3, wherein CBD and (E)-BCP are enriched active ingredients.

Embodiment 5

The pharmaceutical composition of Embodiment 1, wherein at least one of CBD and (E)-BCP is a substantially pure active ingredient.

Embodiment 6

The pharmaceutical composition of Embodiment 5, wherein CBD and (E)-BCP are substantially pure active ingredients.

Embodiment 7

The pharmaceutical composition of any one of Embodiments 1 to 6, wherein the weight ratio of CBD to (E)-BCP is from about 1:1 to about 1:50.

Embodiment 8

The pharmaceutical composition of any one of Embodiments 1 to 7, wherein the weight ratio of CBD to (E)-BCP is selected from the group consisting of about 1:1 to about 1:50; about 1:5 to about 1:50; about 1:10 to about 1:50; about 1:15 to about 1:50; about 1:20 to about 1:50; about 1:25 to about 1:50; about 1:30 to about 1:50; about 1:35 to about 1:50; about 1:40 to about 1:50; and about 1:45 to about 1:50.

Embodiment 9

The pharmaceutical composition of any one of Embodiments 1 to 8, wherein the weight ratio of CBD to (E)-BCP is selected from the group consisting of about 1:1 to about 1:45; about 1:5 to about 1:45; about 1:10 to about 1:45; about 1:15 to about 1:45; about 1:20 to about 1:45; about 1:25 to about 1:45; about 1:30 to about 1:45; about 1:35 to about 1:45; and about 1:40 to about 1:45.

Embodiment 10

The pharmaceutical composition of any one of Embodiments 1 to 9, wherein the weight ratio of CBD to (E)-BCP is selected from the group consisting of about 1:1 to about 1:40; about 1:5 to about 1:40; about 1:10 to about 1:40; about 1:15 to about 1:40; about 1:20 to about 1:40; about 1:25 to about 1:40; about 1:30 to about 1:40; and about 1:35 to about 1:40.

Embodiment 11

The pharmaceutical composition of any one of Embodiments 1 to 10, wherein the weight ratio of CBD to (E)-BCP is selected from the group consisting of about 1:1 to about 1:35; about 1:5 to about 1:35; about 1:10 to about 1:35; about 1:15 to about 1:35; about 1:20 to about 1:35; about 1:25 to about 1:35; and about 1:30 to about 1:35.

Embodiment 12

The pharmaceutical composition of any one of Embodiments 1 to 11, wherein the weight ratio of CBD to (E)-BCP is selected from the group consisting of about 1:1 to about 1:30; about 1:5 to about 1:30; about 1:10 to about 1:30; about 1:15 to about 1:30; about 1:20 to about 1:30; and about 1:25 to about 1:30.

Embodiment 13

The pharmaceutical composition of any one of Embodiments 1 to 12, wherein the weight ratio of CBD to (E)-BCP is selected from the group consisting of about 1:1 to about 1:25; about 1:5 to about 1:25; about 1:10 to about 1:25; about 1:15 to about 1:25; and about 1:20 to about 1:25.

Embodiment 14

The pharmaceutical composition of any one of Embodiments 1 to 13, wherein the weight ratio of CBD to (E)-BCP is selected from the group consisting of about 1:1 to about 1:20; about 1:5 to about 1:20; about 1:10 to about 1:20; and about 1:15 to about 1:20.

Embodiment 15

The pharmaceutical composition of any one of Embodiments 1 to 14, wherein the weight ratio of CBD to (E)-BCP is selected from the group consisting of about 1:1 to about 1:15; about 1:5 to about 1:15; and about 1:10 to about 1:15.

Embodiment 16

The pharmaceutical composition of any one of Embodiments 1 to 15, wherein the weight ratio of CBD to (E)-BCP is selected from the group consisting of about 1:1 to about 1:10; and about 1:5 to about 1:10.

Embodiment 17

The pharmaceutical composition of Embodiment 7, wherein the weight ratio of CBD to (E)-BCP is from about 1:1 to about 1:30.

Embodiment 18

The pharmaceutical composition of any one of Embodiments 1 to 8, wherein the wherein the weight ratio of CBD to (E)-BCP is selected from the group consisting of about 1:1, about 1:2, about 1:3, about 1:4, about 1:5, about 1:6, about 1:7, about 1:8, about 1:9, about 1:10, about 1:11, about 1:12, about 1:13, about 1:14, about 1:15, about 1:16, about 1:17, about 1:18, about 1:19, about 1:20, about 1:21, about 1:22, about 1:23, about 1:24, about 1:25, about 1:26, about 1:27, about 1:28, about 1:29, about 1:30, about 1:35, about 1:40, about 1:45, and about 1:50, Embodiment 19: The pharmaceutical composition of any one of Embodiments 1 to 18, wherein the active ingredient portion contains about 1-10% CBD and about 90-99% (E)-BCP by weight.

Embodiment 20

The pharmaceutical composition of any of Embodiments 1 to 6, wherein the weight ratio of CBD to (E)-BCP is from about 50:1 to about 1:1.

Embodiment 21

The pharmaceutical composition of any one of Embodiments 1 to 6 and 20, wherein the weight ratio of CBD to (E)-BCP is selected from the group consisting of about 50:1 to about 1:1; about 45:1 to about 1:1; about 40:1 to about 1:1; about 35:1 to about 1:1; about 30:1 to about 1:1; about 25:1 to about 1:1; about 20:1 to about 1:1; about 15:1 to about 1:1; about 10:1 to about 1:1 and about 5:1 to about 1:1.

Embodiment 22

The pharmaceutical composition of any one of Embodiments 1 to 6, 20 and 21, wherein the weight ratio of CBD to (E)-BCP is selected from the group consisting of about 45:1 to about 1:1; about 40:1 to about 1:1; about 35:1 to about 1:1; about 30:1 to about 1:1; about 25:1 to about 1:1; about 20:1 to about 1:1; about 15:1 to about 1:1; about 10:1 to about 1:1 and about 5:1 to about 1:1.

Embodiment 23

The pharmaceutical composition of any one of Embodiments 1 to 6, and 20 to 22, wherein the weight ratio of CBD to (E)-BCP is selected from the group consisting of about 40:1 to about 1:1; about 35:1 to about 1:1; about 30:1 to about 1:1; about 25:1 to about 1:1; about 20:1 to about 1:1; about 15:1 to about 1:1; about 10:1 to about 1:1 and about 5:1 to about 1:1.

Embodiment 24

The pharmaceutical composition of any one of Embodiments 1 to 6, and 20 to 23, wherein the weight ratio of CBD to (E)-BCP is selected from the group consisting of about 35:1 to about 1:1; about 30:1 to about 1:1; about 25:1 to about 1:1; about 20:1 to about 1:1; about 15:1 to about 1:1; about 10:1 to about 1:1 and about 5:1 to about 1:1.

Embodiment 25

The pharmaceutical composition of any one of Embodiments 1 to 6, and 20 to 24, wherein the weight ratio of CBD to (E)-BCP is selected from the group consisting of about 30:1 to about 1:1; about 25:1 to about 1:1; about 20:1 to about 1:1; about 15:1 to about 1:1; about 10:1 to about 1:1 and about 5:1 to about 1:1.

Embodiment 26

The pharmaceutical composition of any one of Embodiments 1 to 6, and 20 to 25, wherein the weight ratio of CBD to (E)-BCP is selected from the group consisting of about 25:1 to about 1:1; about 20:1 to about 1:1; about 15:1 to about 1:1; about 10:1 to about 1:1 and about 5:1 to about 1:1.

Embodiment 27

The pharmaceutical composition of any one of Embodiments 1 to 6, and 20 to 26, wherein the weight ratio of CBD to (E)-BCP is selected from the group consisting of about 20:1 to about 1:1; about 15:1 to about 1:1; about 10:1 to about 1:1 and about 5:1 to about 1:1.

Embodiment 28

The pharmaceutical composition of any one of Embodiments 1 to 6, and 20 to 27, wherein the weight ratio of CBD to (E)-BCP is selected from the group consisting of about 15:1 to about 1:1; about 10:1 to about 1:1 and about 5:1 to about 1:1

Embodiment 29

The pharmaceutical composition of any one of Embodiments 1 to 6, and 20 to 28, wherein the weight ratio of CBD to (E)-BCP is selected from the group consisting of about 15:1 to about 1:1; about 10:1 to about 1:1 and about 5:1 to about 1:1.

Embodiment 30

The pharmaceutical composition of Embodiment 20, wherein the weight ratio of CBD to (E)-BCP is from about 30:1 to about 1:1.

Embodiment 31

The pharmaceutical composition of any one of Embodiments 1 to 6, and 20, wherein the wherein the weight ratio of CBD to (E)-BCP is selected from the group consisting of about 50:1; about 45:1; about 40:1; about 35:1; about 30:1; about 29:1; about 28:1; about 27:1; about 26:1; about 25:1; about 24:1; about 23:1; about 22:1; about 21:1; about 20:1; about 19:1; about 18:1; about 17:1; about 16:1; about 15:1; about 14:1; about 13:1; about 12:1; about 11:1; about 10:1; about 9:1; about 8:1; about 7:1; about 6:1; about 5:1; about 4:1; about 3:1; about 2:1 and about 1:1.

Embodiment 32

The pharmaceutical composition of any one of Embodiments 1 to 6, and 20 to 31, wherein the active ingredient portion contains about 90-99% CBD and about 1-10% (E)-BCP by weight.

Embodiment 33

The pharmaceutical composition of any one of Embodiments 1 to 32, wherein a single dose comprises a combined active ingredient content of 300-500 milligrams.

Embodiment 34

The pharmaceutical composition of any one of Embodiments 1 to 33, wherein the pharmaceutical composition comprises from about 300 mg to about 1000 mg of CBD.

Embodiment 35

The pharmaceutical composition of any one of Embodiments 1 to 34, wherein the pharmaceutical composition comprises from about 10 mg to about 100 mg of (E)-BCP.

Embodiment 36

The pharmaceutical composition of any one of Embodiments 1 to 35, wherein the composition is an oral dose.

Embodiment 37

The pharmaceutical composition of any one of Embodiments 1 to 35, wherein the composition is a parenteral injection.

Embodiment 38

The pharmaceutical composition of any one of Embodiments 1 to 35, wherein the composition is a transdermal patch, cream or ointment.

Embodiment 39

The pharmaceutical composition of any one of Embodiments 1 to 35, wherein the composition is an oral mucosal absorption spray.

Embodiment 40

A method of treating pain, said method comprising administering to a patient in need thereof a therapeutically effective amount of the pharmaceutical composition of any one of Embodiments 1 to 39.

Embodiment 41

The method of Embodiment 40, wherein the pain is selected from the group consisting of neuropathic pain including peripheral neuropathy, diabetic neuropathy, post herpetic neuralgia, trigeminal neuralgia, back pain, neuropathy associated with cancer, neuropathy associated with HIV/AIDS, phantom limb pain, carpal tunnel syndrome, central post-stroke pain, pain associated with chronic alcoholism, hypothyroidism, uremia, pain associated with multiple sclerosis, pain associated with spinal cord injury, pain associated with Parkinson's disease, epilepsy, osteoarthritic pain, rheumatoid arthritic pain, visceral pain, and pain associated with vitamin deficiency; and nociceptive pain including pain associated with central nervous system trauma, strains/sprains, and burns; myocardial infarction, acute pancreatitis, post-operative pain, posttraumatic pain, renal colic, pain associated with cancer, pain associated with fibromyalgia, pain associated with carpal tunnel syndrome, and back pain.

Embodiment 42

The method of Embodiment 41, wherein the pain is selected from the group consisting of pain associated with multiple sclerosis, pain associated with cancer, osteoarthritic pain, and rheumatoid arthritic pain.

Embodiment 43

The method of Embodiment 42, wherein the pain is chronic pain.

Embodiment 44

A method of treating epilepsy, said method comprising administering to a patient in need thereof a therapeutically effective amount of the pharmaceutical composition of any one of Embodiments 1 to 39.

Embodiment 45

A method of treating a neurological disease or disorder selected from the group consisting of anxiety, depression, memory loss, dementia, sleep apnea, stroke, urinary incontinence, narcolepsy, essential tremor, epilepsy, movement disorder, atrial fibrillation, cancer (e.g., brain tumors), Parkinson's disease, or Alzheimer's disease, said method comprising administering to a patient in need thereof a therapeutically effective amount of the pharmaceutical composition of any one of Embodiments 1 to 39.

Embodiment 46

The method of Embodiment 45, wherein the neurological disease or disorder is selected from the group consisting of epilepsy, anxiety, and depression.

Embodiment 47

A method of treating an inflammatory skin disease or condition, said method comprising administering to a patient in need thereof a therapeutically effective amount of the pharmaceutical composition of any one of Embodiments 1 to 39.

Embodiment 48

The method of Embodiment 47, wherein the inflammatory skin disease or condition is selected from the group consisting of atopic dermatitis, contact dermatitis, allergic dermatitis, pruritic dermatitis, solar (UVB-induced) dermatitis, chemical-induced dermatitis, bacterial and viral skin inflammation, acne and psoriasis.

Embodiment 49

The method of Embodiment 48, wherein the inflammatory skin disease or condition is selected from the group consisting of atopic dermatitis, acne and psoriasis.

Embodiment 50

The method of Embodiment 49, wherein the inflammatory skin disease or condition is atopic dermatitis.

Embodiment 51

A method of treating inflammation, said method comprising administering to a patient in need thereof a therapeutically effective amount of the pharmaceutical composition of any one of Embodiments 1 to 39.

Embodiment 52

A method of treating substance addiction, said method comprising administering to a patient in need thereof a therapeutically effective amount of the pharmaceutical composition of any one of Embodiments 1 to 39.

Embodiment 53

The method of Embodiment 52, wherein the treatment produces a cravings decrease of at least 10% as measured by a 10 point cravings test.

Embodiment 54

A method of treating substance addiction, said method comprising administering to a patient in need thereof a composition comprising active ingredients, said active ingredients comprising a therapeutically effective amount of tetrahydrocannabinol (THC), cannabidiol (CBD), and (E)-beta-caryophyllene ((E)-BCP).

Embodiment 55

The method of Embodiment 54, wherein the treatment produces a cravings decrease of at least 10% as measured by a 10 point cravings test.

Embodiment 56

A method of treating an inflammatory skin disease or condition, said method comprising administering to a patient in need thereof a therapeutically effective amount of the pharmaceutical composition comprising one or more F-CBDs to the subject in need thereof.

Embodiment 57

The method of Embodiment 56, wherein the F-CBD is a compound selected from a compound of Formula (I), a compound of Formula (Ia), a compound of Formula (II), a compound of Formula (IIa), a compound of Formula (III), a compound of Formula (Ma), a compound of Formula (IV), a compound of Formula (IVa), a compound of Formula (V) or a compound of Formula (VI), described herein.

Embodiment 58

The method of Embodiment 57, wherein the F-CBD is a compound selected from the group consisting of:

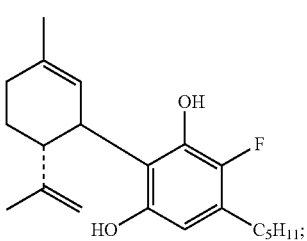

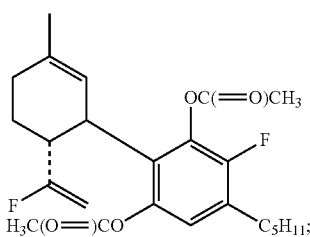

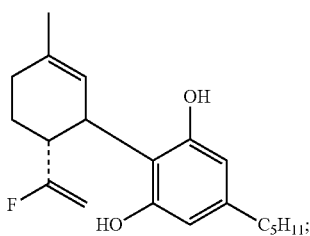

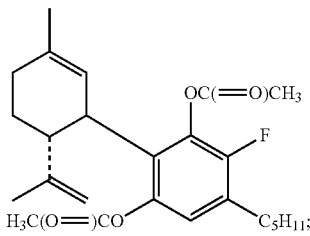

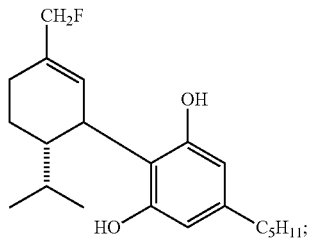

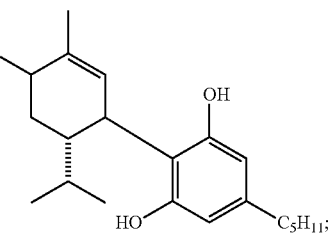

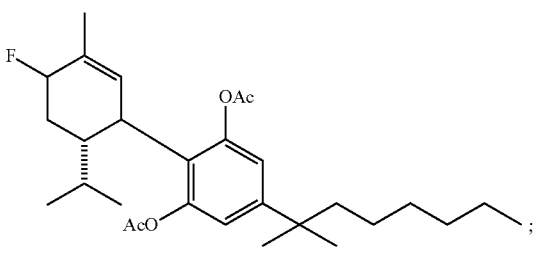

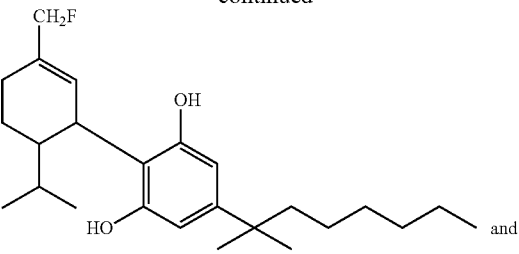

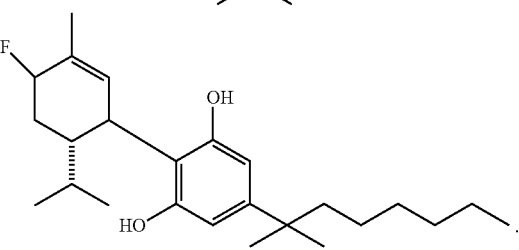

Embodiment 59

The method of Embodiment 58, wherein the F-CBD is a compound of formula

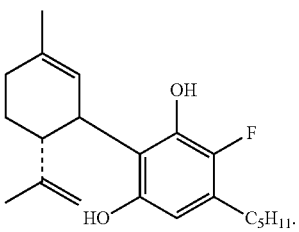

Embodiment 60

The method of any one of Embodiments 56 to 59, wherein the inflammatory skin disease or condition is selected from the group consisting of atopic dermatitis, contact dermatitis, allergic dermatitis, pruritic dermatitis, solar (UVB-induced) dermatitis, chemical-induced dermatitis, bacterial and viral skin inflammation, acne and psoriasis.

Embodiment 61

The method of Embodiment 60, wherein the inflammatory skin disease or condition is selected from the group consisting of atopic dermatitis, acne and psoriasis.

Embodiment 62

The method of Embodiment 61, wherein the inflammatory skin disease or condition is atopic dermatitis.

Embodiment 63

A pharmaceutical composition comprising one or more active ingredients, wherein the active ingredients consist essentially of a therapeutically effective amount of tetrahydrocannabinol (THC), cannabidiol (CBD), and (E)-beta-caryophyllene ((E)-BCP).

Embodiment 64

The pharmaceutical composition of Embodiment 63, wherein at least one of the active ingredients is an enriched active ingredient.

Embodiment 65

The pharmaceutical composition of Embodiment 64, wherein all of the active ingredients are enriched active ingredients.

Embodiment 66

The pharmaceutical composition of Embodiment 63, wherein at least one of the active ingredients is a substantially pure active ingredient.

Embodiment 67

The pharmaceutical composition of Embodiment 66, wherein all of the active ingredients are substantially pure active ingredients.

Embodiment 68

The pharmaceutical composition of Embodiment 63, wherein the ratio of CBD to THC is from about 30:1 to about 10:1.

Embodiment 69

The pharmaceutical composition of Embodiment 63, wherein the ratio of CBD to (E)-BCP is from 30:1 to about 10:1.

Embodiment 70

The pharmaceutical composition of Embodiment 63, wherein the active ingredients exist at a ratio of 1-10 parts THC: 20-40 parts CBD: and 1-10 parts (E)-BCP).

Embodiment 71

The pharmaceutical composition of Embodiment 63, wherein the pharmaceutical composition comprises 1-10% THC, 80-90% CBD, and 1-10% (E)-BCP.

Embodiment 72

The pharmaceutical composition of Embodiment 63, wherein a single dose comprises a combined active ingredient content of 300-500 milligrams.

Embodiment 73

The pharmaceutical composition of Embodiment 63, wherein the pharmaceutical composition comprises from about 1 mg to about 20 mg of THC.

Embodiment 74

The pharmaceutical composition of Embodiment 63, wherein the pharmaceutical composition comprises from about 300 mg to about 1000 mg of CBD.

Embodiment 75

The pharmaceutical composition of Embodiment 63, wherein the pharmaceutical composition comprises from about 10 mg to about 100 mg of (E)-BCP.

Embodiment 76

The pharmaceutical composition of Embodiment 63, wherein the composition is an oral dose.

Embodiment 77

The pharmaceutical composition of Embodiment 63, wherein the composition is a parenteral injection.

Embodiment 78

The pharmaceutical composition of Embodiment 63, wherein the composition is a transdermal patch, cream or ointment.

Embodiment 79

The pharmaceutical composition of Embodiment 63, wherein the composition is an oral mucosal absorption spray.

Embodiment 80

A method of treating pain, said method comprising administering to a patient in need thereof a therapeutically effective amount of the pharmaceutical composition of any one of Embodiments 63 to 79.

Embodiment 81

The method of Embodiment 80, wherein the pain is selected from the group consisting of neuropathic pain including peripheral neuropathy, diabetic neuropathy, post herpetic neuralgia, trigeminal neuralgia, back pain, neuropathy associated with cancer, neuropathy associated with HIV/AIDS, phantom limb pain, carpal tunnel syndrome, central post-stroke pain, pain associated with chronic alcoholism, hypothyroidism, uremia, pain associated with multiple sclerosis, pain associated with spinal cord injury, pain associated with Parkinson's disease, epilepsy, osteoarthritic pain, rheumatoid arthritic pain, visceral pain, and pain associated with vitamin deficiency; and nociceptive pain including pain associated with central nervous system trauma, strains/sprains, and burns; myocardial infarction, acute pancreatitis, post-operative pain, posttraumatic pain, renal colic, pain associated with cancer, pain associated with fibromyalgia, pain associated with carpal tunnel syndrome, and back pain.

Embodiment 82

The method of Embodiment 81, wherein the pain is selected from the group consisting of pain associated with multiple sclerosis, pain associated with cancer, osteoarthritic pain, and rheumatoid arthritic pain.

Embodiment 83

The method of Embodiment 82, wherein the pain is chronic pain.

Embodiment 84

A method of treating epilepsy, said method comprising administering to a patient in need thereof a therapeutically effective amount of the pharmaceutical composition of any one of Embodiments 163 to 79.

Embodiment 85

A method of treating a neurological disease or disorder selected from the group consisting of anxiety, depression, memory loss, dementia, sleep apnea, stroke, urinary incontinence, narcolepsy, essential tremor, epilepsy, movement disorder, atrial fibrillation, cancer (e.g., brain tumors), Parkinson's disease, or Alzheimer's disease, said method comprising administering to a patient in need thereof a therapeutically effective amount of the pharmaceutical composition of any one of Embodiments 63 to 79.

Embodiment 86

The method of Embodiment 85, wherein the neurological disease or disorder is selected from the group consisting of epilepsy, anxiety, and depression.

Embodiment 87

A method of treating an inflammatory skin disease or condition, said method comprising administering to a patient in need thereof a therapeutically effective amount of the pharmaceutical composition of any one of Embodiments 63 to 79.

Embodiment 88

The method of Embodiment 87, wherein the inflammatory skin disease or condition is selected from the group consisting of atopic dermatitis, contact dermatitis, allergic dermatitis, pruritic dermatitis, solar (UVB-induced) dermatitis, chemical-induced dermatitis, bacterial and viral skin inflammation, acne and psoriasis.

Embodiment 89

The method of Embodiment 88, wherein the inflammatory skin disease or condition is selected from the group consisting of atopic dermatitis, acne and psoriasis.

Embodiment 90

The method of Embodiment 89, wherein the inflammatory skin disease or condition is atopic dermatitis.

Embodiment 91

A method of treating inflammation, said method comprising administering to a patient in need thereof a therapeutically effective amount of the pharmaceutical composition of any one of Embodiments 63 to 79.

Embodiment 92

A method of treating substance addiction, said method comprising administering to a patient in need thereof a therapeutically effective amount of the pharmaceutical composition of any one of Embodiments 63 to 79.

Embodiment 93

The method of Embodiment 92, wherein the treatment produces a cravings decrease of at least 10% as measured by a 10 point cravings test.

Embodiment 94

A method of treating an inflammatory skin disease or condition, said method comprising administering to a patient in need thereof a therapeutically effective amount of the pharmaceutical composition of any one of Embodiments 63 to 79 to the subject in need thereof.

Embodiment 95

The method of Embodiment 94, wherein the inflammatory skin disease or condition is selected from the group consisting of atopic dermatitis, contact dermatitis, allergic dermatitis, pruritic dermatitis, solar (UVB-induced) dermatitis, chemical-induced dermatitis, bacterial and viral skin inflammation, acne and psoriasis.

Embodiment 96

The method of Embodiment 95, wherein the inflammatory skin disease or condition is selected from the group consisting of atopic dermatitis, acne and psoriasis.

Embodiment 97

The method of Embodiment 96, wherein the inflammatory skin disease or condition is atopic dermatitis.

INCORPORATION BY REFERENCE

All references, articles, publications, patents, patent publications, and patent applications cited herein are incorporated by reference in their entireties for all purposes. However, mention of any reference, article, publication, patent, patent publication, and patent application cited herein is not, and should not, be taken as an acknowledgment or any form of suggestion that they constitute valid prior art or form part of the common general knowledge in any country in the world.

The invention claimed is:

1. A pharmaceutical composition for reducing inflammation, comprising a therapeutically effective amount of Cannabidiol (CBD) and (E)-Beta Caryophyllene ((E)-BCP), wherein the molar ratio of CBD to (E)-BCP is from about 1:2 to about 1:33.3.

2. The pharmaceutical composition of claim 1, wherein the pharmaceutical composition consists essentially of CBD and (E)-BCP.

3. The pharmaceutical composition of claim 1, wherein at least one of CBD and (E)-BCP is an enriched active ingredient.

4. The pharmaceutical composition of claim 3, wherein CBD and (E)-BCP are enriched active ingredients.

5. The pharmaceutical composition of claim 1, wherein at least one of CBD and (E)-BCP is a substantially pure active ingredient.

6. The pharmaceutical composition of claim 5, wherein CBD and (E)-BCP are substantially pure active ingredients.

7. The pharmaceutical composition of claim 1, wherein the molar ratio of CBD to (E)-BCP is from about 1:2 to about 1:30.

8. The pharmaceutical composition of claim 1, wherein a single dose comprises a combined CBD and (E)-BCP content of 300-500 milligrams.

9. The pharmaceutical composition of claim 1, wherein the composition is an oral dose.

10. The pharmaceutical composition of claim 1, wherein the composition is a parenteral injection.

11. The pharmaceutical composition of claim 1, wherein the composition is a transdermal patch, cream or ointment.

12. The pharmaceutical composition of claim 1, wherein the composition is an oral mucosal absorption spray.

13. The pharmaceutical composition of claim 1, wherein the composition is substantially THC-free.

14. The pharmaceutical composition of claim 1, wherein a single dose comprises a combined CBD and (E)-BCP content of 300-500 milligrams.

15. The pharmaceutical composition of claim 1, wherein the composition is an oral dose.

16. The pharmaceutical composition of claim 1, wherein the composition is a parenteral injection.

17. The pharmaceutical composition of claim 1, wherein the composition is a transdermal patch, cream or ointment.

18. The pharmaceutical composition of claim 1, wherein the composition is an oral mucosal absorption spray.

19. The composition of claim 1, wherein the composition is substantially THC-free.

20. A pharmaceutical composition for treatment of inflammatory conditions, comprising a therapeutically effective a mount of Cannabidiol (CBD) and (E)-Beta Caryophyllene ((E)-BCP), wherein the molar ratio of CBD to (E)-BCP is from about 1:2 to about 1:33.3.

21. A pharmaceutical composition comprising a therapeutically effective amount of Cannabidiol (CBD) and (E)-Beta Caryophyllene ((E)-BCP), wherein the molar ratio of CBD to (E)-BCP is from about 1:2 to about 1:33.3; wherein the composition has anti-inflammatory activity.

* * * * *

UNITED STATES PATENT AND TRADEMARK OFFICE
CERTIFICATE OF CORRECTION

PATENT NO. : 11,154,515 B2  
APPLICATION NO. : 16/698070  
DATED : October 26, 2021  
INVENTOR(S) : Biro et al.

It is certified that error appears in the above-identified patent and that said Letters Patent is hereby corrected as shown below:

In the Claims

Column 90, Claim 20, Line 11 replace "a mount" with --amount--.

Signed and Sealed this  
Fourteenth Day of December, 2021

Drew Hirshfeld  
*Performing the Functions and Duties of the*  
*Under Secretary of Commerce for Intellectual Property and*  
*Director of the United States Patent and Trademark Office*